United States Patent
Panicker et al.

(10) Patent No.: US 11,851,482 B2
(45) Date of Patent: Dec. 26, 2023

(54) ANTI-COMPLEMENT FACTOR BB ANTIBODIES AND USES THEREOF

(71) Applicant: Bioverativ USA Inc., Waltham, MA (US)

(72) Inventors: Sandip Panicker, South San Francisco, CA (US); Graham Parry, Cambridge, MA (US); Karen Sue Christopherson, San Mateo, CA (US); Tony SangYoung Byun, Brisbane, CA (US)

(73) Assignee: Genzyme Corporation, Cambridge, MA (US)

( * ) Notice: Subject to any disclaimer, the term of this patent is extended or adjusted under 35 U.S.C. 154(b) by 354 days.

(21) Appl. No.: 17/151,860

(22) Filed: Jan. 19, 2021

(65) Prior Publication Data

US 2021/0221877 A1 Jul. 22, 2021

Related U.S. Application Data

(63) Continuation of application No. 16/091,447, filed as application No. PCT/US2017/025784 on Apr. 3, 2017, now Pat. No. 10,934,347.

(60) Provisional application No. 62/317,897, filed on Apr. 4, 2016.

(51) Int. Cl.
- *C07K 16/18* (2006.01)
- *C07K 16/40* (2006.01)
- *A61K 39/00* (2006.01)

(52) U.S. Cl.
CPC .............. *C07K 16/18* (2013.01); *C07K 16/40* (2013.01); *A61K 2039/505* (2013.01); *C07K 2317/24* (2013.01); *C07K 2317/33* (2013.01); *C07K 2317/76* (2013.01); *C07K 2317/92* (2013.01); *C07K 2317/94* (2013.01)

(58) Field of Classification Search
CPC ................................ C07K 16/18; C12N 15/00
See application file for complete search history.

(56) References Cited

U.S. PATENT DOCUMENTS

| | | |
|---|---|---|
| 6,737,056 B1 | 5/2004 | Presta |
| 10,934,347 B2 | 3/2021 | Panicker et al. |
| 11,192,944 B2 | 12/2021 | Panicker et al. |
| 11,242,382 B2 | 2/2022 | Parry et al. |
| 2009/0214538 A1 | 8/2009 | Fung et al. |
| 2009/0280128 A1 | 11/2009 | Kamogawa et al. |
| 2013/0136735 A1 | 5/2013 | Truneh et al. |
| 2014/0286936 A1 | 9/2014 | Chambers et al. |
| 2015/0239987 A1 | 8/2015 | Liang et al. |
| 2016/0015828 A1 | 1/2016 | Torgov et al. |
| 2017/0044259 A1 | 2/2017 | Tipton et al. |
| 2019/0153079 A1 | 5/2019 | Panicker et al. |
| 2020/0239556 A1 | 7/2020 | Panicker et al. |
| 2022/0213179 A1 | 7/2022 | Graham et al. |

FOREIGN PATENT DOCUMENTS

| | | |
|---|---|---|
| CN | 101918444 A | 12/2010 |
| CN | 104220454 A | 12/2014 |
| CN | 104884088 A | 9/2015 |
| CN | 106232624 A | 12/2016 |
| CN | 109563158 A | 4/2019 |
| JP | 2015/514111 A | 5/2015 |
| JP | 2015-514111 A | 5/2015 |
| JP | 2020078304 A | 5/2020 |
| WO | WO 97/34631 A1 | 9/1997 |
| WO | WO 98/23289 A1 | 6/1998 |
| WO | WO 02/060919 A2 | 8/2002 |
| WO | WO 2005/077417 A1 | 8/2005 |
| WO | WO 2009/029669 A1 | 3/2009 |
| WO | WO 2009/082624 A2 | 7/2009 |
| WO | WO 2011/041391 A1 | 4/2011 |
| WO | WO 2013/126746 A2 | 8/2013 |
| WO | WO 2013/152020 A1 | 10/2013 |
| WO | WO 2014/044793 A2 | 3/2014 |
| WO | WO 2015/051159 A1 | 4/2015 |
| WO | WO 2015/130826 A1 | 9/2015 |
| WO | WO 2017/176651 A1 | 10/2017 |
| WO | WO 2019/075220 A1 | 4/2019 |

OTHER PUBLICATIONS

International Search Report and Written Opinion, dated Aug. 25, 2021 for Application No. PCT/US2021/027981.
International Preliminary Report on Patentability, dated Nov. 3, 2022 for Application No. PCT/US2021/027981.
Bryson et al., Prediction of immunogenicity of therapeutic proteins: validity of computational tools. BioDrugs. Feb. 1, 2010;24(1):1-8.
Cao et al., Human neutrophil peptides and complement factor Bb in pathogenesis of acquired thrombotic thrombocytopenia purpura. Haematologica. Nov. 2016;101(11):1319-1326. Epub Aug. 4, 2016.
Chen et al., Enhancement and destruction of antibody function by somatic mutation: unequal occurrence is controlled by V gene combinatorial associations. EMBO J. Jun. 15, 1995;14(12):2784-94.
Chothia et al., Canonical structures for the hypervariable regions of immunoglobulins. J Mol Biol. Aug. 20, 1987;196(4):901-17.
Daha et al., Stabilization of the amplification convertase of complement by monoclonal antibodies directed against human factor B. J Immunol. May 1984;132(5):2538-42.
Dall'Acqua et al., Properties of human IgG1s engineered for enhanced binding to the neonatal Fc receptor (FcRn). J Biol Chem. Aug. 18, 2006;281(33):23514-24. Epub Jun. 21, 2006.
De Vriese et al., Kidney Disease Caused by Dysregulation of the Complement Alternative Pathway: An Etiologic Approach. J Am Soc Nephrol. Dec. 2015;26(12):2917-29. Epub Jul. 16, 2015.

(Continued)

*Primary Examiner* — Prema M Mertz
(74) *Attorney, Agent, or Firm* — Wolf, Greenfield & Sacks, P.C.

(57) ABSTRACT

The present disclosure provides anti-complement factor Bb antibodies, and compositions comprising the antibodies. The anti-Bb antibodies are useful for treating complement-mediated disorders. The present disclosure provides methods of treating complement-mediated disorders.

20 Claims, 28 Drawing Sheets

Specification includes a Sequence Listing.

(56) References Cited

OTHER PUBLICATIONS

Gold et al., Variation in factor B (BF) and complement component 2 (C2) genes is associated with age-related macular degeneration. Nat Genet. Apr. 2006;38(4):458-62. Epub Mar. 5, 2006. Author manuscript.

Holers, The spectrum of complement alternative pathway-mediated diseases. Immunol Rev. Jun. 2008;223:300-16.

Holt et al., Domain antibodies: proteins for therapy. Trends Biotechnol. Nov. 2003;21(11):484-90.

Kabat et al., Unusual distributions of amino acids in complementarity-determining (hypervariable) segments of heavy and light chains of immunoglobulins and their possible roles in specificity of antibody-combining sites. J Biol Chem. Oct. 10, 1977;252(19):6609-16.

Kussie et al., A single engineered amino acid substitution changes antibody fine specificity. J Immunol. Jan. 1, 1994;152(1):146-52.

Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.

Lefranc et al., IMGT unique numbering for immunoglobulin and T cell receptor variable domains and Ig superfamily V-like domains. Dev Comp Immunol. Jan. 2003;27(1):55-77.

Maccallum et al., Antibody-antigen interactions: contact analysis and binding site topography. J Mol Biol. Oct. 11, 1996;262(5):732-45.

Perry et al., New approaches to prediction of immune responses to therapeutic proteins during preclinical development. Drugs R D. 2008;9(6):385-96.

Pio et al., The Role of Complement in Tumor Growth. Adv Exp Med Biol. 2014;772: 229-262. Author manuscript.

Schubart et al., Small-molecule factor B inhibitor for the treatment of complement-mediated diseases. Proc Natl Acad Sci U S A. Apr. 16, 2019;116(16):7926-7931. Epub Mar. 29, 2019.

Shaner et al., A guide to choosing fluorescent proteins. Nat Methods. Dec. 2005;2(12):905-9.

Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. Epub Nov. 28, 2000.

Smith et al., Mouse model recapitulating human Fcγ receptor structural and functional diversity. Proc Natl Acad Sci U S A. Apr. 17, 2012;109(16):6181-6. Epub Apr. 2, 2012.

Thurman, Complement in kidney disease: core curriculum 2015. Am J Kidney Dis. Jan. 2015;65(1):156-68. Epub Oct. 18, 2014. Author manuscript.

Thurman et al., Complement Therapeutics in Autoimmune Disease. Front Immunol. Apr. 3, 2019;10:672. 9 pages.

U.S. Appl. No. 16/091,447, filed Oct. 4, 2018, Granted, U.S. Pat. No. 10,934,347.

U.S. Appl. No. 16/755,461, filed Apr. 10, 2020, Published, 2020-0239556.

EP 17779607.5, Dec. 17, 2019, Extended European Search Report.

PCT/US2017/025784, Jul. 11, 2017, Invitation to Pay Additional Fees.

PCT/US2017/025784, Sep. 7, 2017, International Search Report and Written Opinion.

PCT/US2017/025784, Oct. 18, 2018, International Preliminary Report on Patentability.

PCT/US2018/055444, Jan. 3, 2019, International Search Report and Written Opinion.

PCT/US2018/055444, Apr. 23, 2020, International Preliminary Report on Patentability.

Extended European Search Report dated Dec. 17, 2019 in connection with Application No. EP 17779607.5.

Invitation to Pay Additional Fees for Application No. PCT/US2017/025784 dated Jul. 11, 2017.

International Search Report and Written Opinion for Application No. PCT/US2017/025784 dated Sep. 7, 2017.

International Preliminary Report on Patentability for Application No. PCT/US2017/025784 dated Oct. 18, 2018.

International Search Report and Written Opinion for Application No. PCT/US2018/055444 dated Jan. 3, 2019.

International Preliminary Report on Patentability dated Apr. 23, 2020 in connection with Application No. PCT/US2018/055444.

U.S. Appl. No. 17/234,618, filed Apr. 19, 2021, Granted, U.S. Pat. No. 11,242,382.

U.S. Appl. No. 17/557,318, filed Dec. 21, 2021, Published, 2022-0213179.

PCT/US2021/027981, Aug. 25, 2021, International Search Report and Written Opinion.

PCT/US2021/027981, Nov. 3, 2022, International Preliminary Report on Patentability.

Binding of anti - Factor Bb mAbs

| Clone | Binding to Factor Bb (EC$_{50}$, M) |
|---|---|
| M4 | 8.735e-010 |
| M10 | 3.345e-010 |
| M12 | 7.612e-010 |
| M17 | 3.140e-009 |
| M18 | 3.360e-010 |
| M20 | 5.461e-010 |

FIG. 2

Specificity of Binding to Factor B versus Factor Bb

| Anti-Factor Bb Clone | Ratio OD fBb/fB (ELISA) | Binding to Factor B in Solution (SEC) |
|---|---|---|
| M4  | 00.59 | + |
| M10 | 05.49 | − |
| M12 | 00.82 | + |
| M17 | 70.66 | − |
| M18 | 08.40 | − |
| M20 | 00.50 | + |

FIG. 4

Binding of anti-Factor Bb mAbs to Cyno Factor B and Factor Bb

| | M10 | M12 | M14 | M17 | M18 | M20 |
|---|---|---|---|---|---|---|
| | | | Binding Affinity (M) | | | |
| Factor B | 3.493E-09 | 5.563E-09 | 7.813E-09 | Not detected | 4.985E-09 | 2.551E-08 |
| Factor Bb | 4.88E-10 | 2.554E-09 | 2.503E-09 | ~2.639e-009 | 4.488E-10 | 7.163E-08 |

FIG. 5

Inhibition of Complement AP Activity by anti-Factor Bb Monoclonal Antibodies

| Clone | Wieslab AP (IC$_{50}$, M) | AP Hemolysis (IC$_{50}$, M) | C3b Deposition (IC$_{50}$, M) |
|---|---|---|---|
| M4 | 6.090E-008 | 1.32E-08 | 1.4E-08 |
| M10 | 2.287E-007 | 3.84E-08 | 7.78E-08 |
| M12 | 5.550E-008 | 1.17E-08 | 1.22E-08 |
| M17 | ~7.706E-007 | 4.34E-08 | 1.2E-07 |
| M18 | 2.258E-007 | 3.96E-08 | 7.68E-08 |
| M20 | 1.417E-007 | 3.19E-08 | 5.41E-08 |

FIG. 9

Table 1: Anti-Factor Bb Antibody Sequences

| Antibody | CDR-1 | CDR-2 | CDR-3 | V Region |
|---|---|---|---|---|
| M10 VL | SEQ ID NO: 1<br>QDVGTA | SEQ ID NO: 2<br>WAS | SEQ ID NO: 3<br>HQHSSNPLT | SEQ ID NO: 7<br>DIVMTQSHKFMSTSVGDRVSITCKA<br>SQDVGTAVAWYQQKPGQSPKLLIYW<br>ASTRHTGVPDRFTGSGSGTDFTLTI<br>TNVQSEDLAVYFCHQHSSNPLTFGA<br>GTKLELK |
| M10 VH | SEQ ID NO: 4<br>GFTFSNYA | SEQ ID NO: 5<br>ISNRGSYT | SEQ ID NO: 6<br>ARERPMDY | SEQ ID NO: 8<br>EVQLVESGGALVKPGGSLKLSCAAS<br>GFTFSNYAMSWVRQTPEKRLEWVAT<br>ISNRGSYTYYPDSVKGRFTISRDNA<br>KNTLYLQMSSLRSEDTALYYCARER<br>PMDYWGQGTSVTVSS |

FIG. 12A

Table 1, continued

| Antibody | | CDR-1 | CDR-2 | CDR-3 | V Region |
|---|---|---|---|---|---|
| M4 VL | | SEQ ID NO: 9<br><br>ESLLHSNGITY | SEQ ID NO: 10<br><br>RMS | SEQ ID NO: 11<br><br>AQMLERPWT | SEQ ID NO: 15<br><br>DIVMTQAAFSNPVTLGTSASISCSS<br>SKSLLHSNGITYLYWYLQRPGQSPQ<br>LLIYRMSNLASGVPDRFSGSGSGTD<br>FTLRISRVEAEDVGVYYCAQMLERP<br>WTFGGGTKLEIK |
| M4 VH | | SEQ ID NO: 12<br><br>GYSFTDYL | SEQ ID NO: 13<br><br>INPYNGDA | SEQ ID NO: 14<br><br>ARLENDYGFTY | SEQ ID NO: 16<br><br>EVQLQQSGPELVKPGASVKMSCKAS<br>GYSFTDYLMNWVKQSHGKSLEWIGR<br>INPYNGDAFYNQRFKGKATLTVDKS<br>SSTAHMELRSLTSEDSALYYCARLE<br>NDYGFTYWGQGTLVTVSA |

FIG. 12B

Table 1, continued

| Antibody | CDR-1 | CDR-2 | CDR-3 | V Region |
|---|---|---|---|---|
| M20 VL | SEQ ID NO: 17<br><br>QGINNY | SEQ ID NO: 18<br><br>YTS | SEQ ID NO: 19<br><br>QQHSKLPWT | SEQ ID NO: 23<br><br>TEYRASSGINARYMGGDRVTISCSA<br>SQGINNYLNWYQQKPDGTVKLLIYY<br>TSSLHSGVPSRFSGSGSGTDYSLTI<br>SNLEPEDVATYYCQQHSKLPWTFGG<br>GTKLEIK |
| M20 VH | SEQ ID NO: 20<br><br>GFSLSTFGLG | SEQ ID NO: 21<br><br>IWWNDDK | SEQ ID NO: 22<br><br>VQIPYGSRNGFDY | SEQ ID NO: 24<br><br>QVTLKESGPGILQPSQTLSLTCSFS<br>GFSLSTFGLGVGWIRQPSGKGLEWL<br>ASIWWNDDKYNSDLKRRPTISRDT<br>SNSQVFLKISSVDTADTATYFCVQI<br>PYGSRNGFDYWGQGTSLTVSS |

FIG. 12C

Table 1, continued

| Antibody | CDR-1 | CDR-2 | CDR-3 | V Region |
|---|---|---|---|---|
| M17 VL | SEQ ID NO: 25<br>QDVGSA | SEQ ID NO: 2<br>WAS | SEQ ID NO: 26<br>QQYSSYPYT | SEQ ID NO: 30<br>DIVMTPSHKEMSTSVGDRVSITCKA<br>SQDVGSAVAWYQQKPGHSPKLLIFW<br>ASTRHTGVPDRFTGSGSGTDFTLTI<br>SNVQSEDLADYFCQQYSSYPYTFGG<br>GTRLEIK |
| M17 VH | SEQ ID NO: 27<br>GFTFSNFA | SEQ ID NO: 28<br>ISNGGGYT | SEQ ID NO: 29<br>ARIYYGSSYEDWFAY | SEQ ID NO: 31<br>EVQLVESGGVLVKPGGSLKLSCAAS<br>GFTFSNFAMSWVRQTPAKRLEWVAT<br>ISNGGGYTYYPDSVQGRFTISRDNA<br>NNTLYLQMSSLRSEDTALYYCARIY<br>YGSSYEDWFAYWGQGTLVTVSA |

FIG. 12D

Table 1, continued

| Antibody | CDR-1 | CDR-2 | CDR-3 | V Region |
|---|---|---|---|---|
| M18 VL (has the same sequence as M10 VL) | SEQ ID NO: 1<br><br>QDVGTA | SEQ ID NO: 2<br><br>WAS | SEQ ID NO: 3<br><br>HQHSSNPLT | SEQ ID NO: 7<br><br>DIVMTQSHKFMSTSVGDRVSITCKA<br><br>SQDVGTAVAWYQQKPGQSPKLLIYW<br><br>ASTRHTGVPDRFTGSGSGTDFTLTI<br><br>TNVQSEDLAVYFCHQHSSNPLTFGA<br><br>GTKLELK |
| M18 VH (has the same sequence as M10 VH) | SEQ ID NO: 4<br><br>GFTFSNYA | SEQ ID NO: 5<br><br>ISNRGSYT | SEQ ID NO: 6<br><br>ARERPMDY | SEQ ID NO: 8<br><br>EVQLVESGGGALVKPGGSLKLSCAAS<br><br>GFTFSNYAMSWVRQTPEKRLEWVAT<br><br>ISNRGSYTYYPDSVKGRFTISRDNA<br><br>KNTLYLQMSSLRSEDTALYYCARER<br><br>PMDYWGQGTSVTVSS |

FIG. 12E

Table 1, continued

| Antibody | CDR-1 | CDR-2 | CDR-3 | V Region |
|---|---|---|---|---|
| M12 VL (has the same sequence as M4 VL) | SEQ ID NO: 9<br>KSLLHSNGITY | SEQ ID NO: 10<br>RMS | SEQ ID NO: 11<br>AQMLERPWT | SEQ ID NO: 15<br>DIVMTQAAFSNPVTLGTSASISCSS<br>SKSLLHSNGITYLYWYLQRPGQSPQ<br>LLIYRMSNLASGVPDRFSGSGSGTD<br>FTLRISRVEAEDVGVYYCAQMLERP<br>WTFGGGTKLEIK |
| M12 VH (has the same sequence as M4 VL) | SEQ ID NO: 12<br>GYSFTDYL | SEQ ID NO: 13<br>INPYNGDA | SEQ ID NO: 14<br>ARLENDYGFTY | SEQ ID NO: 16<br>EVQLQQSGPELVKPGASVKMSCKAS<br>GYSFTDYLMWVKQSHGKSLEWIGR<br>INPYNGDAFYNQRFKGKATLTVDKS<br>SSTAHMELRSLTSEDSALYYCARLE<br>NDYGFTYWGQGTLVTVSA |

IMGT numbering system was used to identify the CDR's (ref. Lefranc, M.-P. et al., Dev. Comp. Immunol. 27, 55-77 (2003)).

Factor Bb

```
  1 mgsnlspqlc lmpfilglls ggvttpwsl arpggsscsle gveikggsfr llqeggaley
 61 vcpsgfypyp vqtrtcrstg swstlktqdg ktvrkaecra ihcprphdfe ngeywprspy
121 ynvsdeisfh cydgytlrgs anrtcqvngr wsgqtaicdn gagycsnpgi pigtr FIG. 21
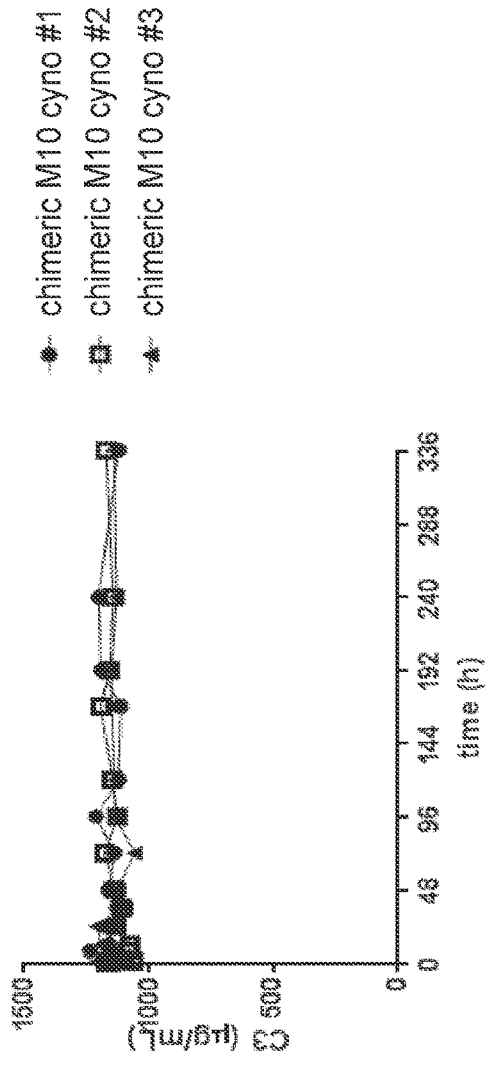
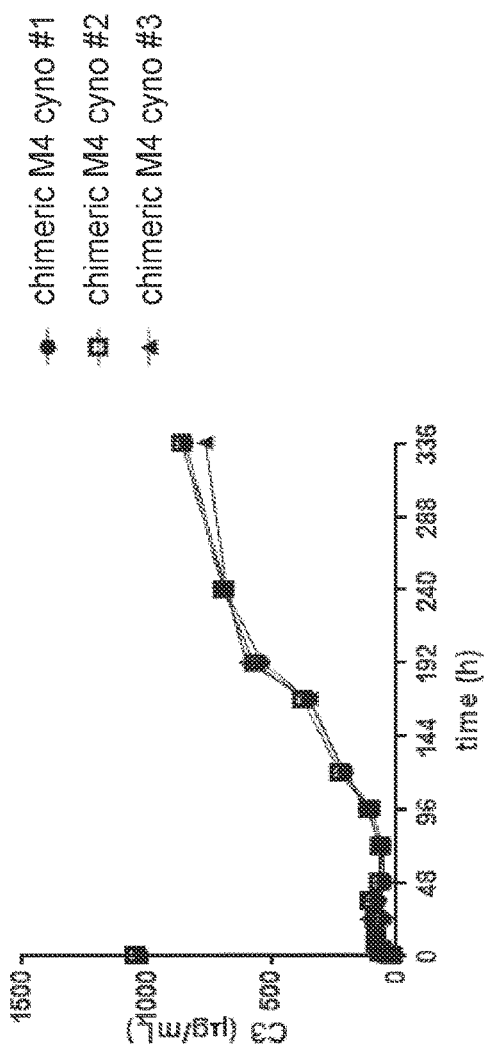

… # ANTI-COMPLEMENT FACTOR BB ANTIBODIES AND USES THEREOF

RELATED APPLICATIONS

This application is a continuation of U.S. application Ser. No. 16/091,447, filed Oct. 4, 2018, which is a national stage filing under 35 U.S.C. § 371 of international application number PCT/US17/25784, filed Apr. 3, 2017, which was published under PCT Article 21(2) in English and claims the benefit under 35 U.S.C. § 119(e) of U.S. provisional application Ser. No. 62/317,897, filed Apr. 4, 2016, each of which is incorporated by reference herein in its entirety.

GOVERNMENT LICENSE RIGHTS

This invention was made with government support under R43HL134531 awarded by National Institutes of Health. The government has certain rights in the invention.

INTRODUCTION

The complement system is part of the innate immune system. Its primary role is to "complement" the ability of antibodies and phagocytic cells to clear harmful pathogens from an organism. However, aberrant activation of the complement system does occur and causes damage to host tissue in a wide variety of pathological settings, ranging from autoimmune disease to organ transplantation. A number of anti-complement therapies are in clinical development to prevent damage caused by aberrant activation of the complement system.

The complement system includes three separate upstream activation pathways, all converging on a common terminal pathway. Two of the pathways are induced by specific and distinct mechanisms: the classical pathway (CP) is engaged when antibodies bind to antigens, and the lectin pathway (LP) is activated by carbohydrate residues on the surface of pathogens. The alternative pathway (AP) is unique in that it is continuously active at a basal level, referred to as "AP tick-over"; its activity can be greatly increased by a variety of signals on foreign surfaces and damaged cells via a positive-feedback amplification loop. The primary driver of the AP amplification loop is the AP convertase (C3bBb). This enzyme is formed when the zymogen factor B is cleaved to generate the split product fBb, which rapidly associates with surface-bound C3b to form active enzyme C3bBb. C3bBb then continues to cleave additional molecules of the central C3 protein, leading to the generation of opsonins (C3b, iC3b), anaphylatoxins (C3a and C5a) and the terminal lytic complex (MAC; C5b-9).

SUMMARY

The present disclosure provides anti-complement factor Bb antibodies, and compositions comprising the antibodies. The anti-Bb antibodies are useful for treating complement-mediated disorders. The present disclosure provides methods of treating complement-mediated disorders.

The present disclosure provides a humanized antibody specific for complement factor Bb, wherein the antibody is selected from the group consisting of: a) an antibody comprising light chain complementarity determining regions (CDRs) of an antibody light chain variable (VL) region comprising amino acid sequence SEQ ID NO:7; b) an antibody comprising light chain CDRs of an antibody heavy chain variable (VH) region comprising amino acid sequence SEQ ID NO:8; c) an antibody comprising light chain CDRs of an antibody VL region comprising amino acid sequence SEQ ID NO:15; d) an antibody comprising heavy chain CDRs of an antibody VH region comprising amino acid sequence SEQ ID NO:16; e) an antibody comprising light chain CDRs of an antibody VL region comprising amino acid sequence SEQ ID NO:23; f) an antibody comprising heavy chain CDRs of an antibody VH region comprising amino acid sequence SEQ ID NO:24; g) an antibody comprising light chain CDRs of an antibody VL region comprising amino acid sequence SEQ ID NO:31; h) an antibody comprising heavy chain CDRs of an antibody VH region comprising amino acid sequence SEQ ID NO:32; i) an antibody comprising light chain CDRs of an antibody VL region comprising amino acid sequence SEQ ID NO: 39; j) an antibody comprising heavy chain CDRs of an antibody VH region comprising amino acid sequence SEQ ID NO:40; k) an antibody comprising light chain CDRs of an antibody VL region comprising amino acid sequence SEQ ID NO:47; and 1) an antibody comprising heavy chain CDRs of an antibody VH region comprising amino acid sequence SEQ ID NO:48. In some cases, the antibody is selected from the group consisting of: a) an antibody comprising light chain CDRs of an antibody VL region comprising amino acid sequence SEQ ID NO:7 and heavy chain CDRs of an antibody VH region comprising amino acid sequence SEQ ID NO:8; b) an antibody comprising light chain CDRs of an antibody VL region comprising amino acid sequence SEQ ID NO:15 and heavy chain CDRs of an antibody VH region comprising amino acid sequence SEQ ID NO:16; c) an antibody comprising light chain CDRs of an antibody VL region comprising amino acid sequence SEQ ID NO:23 and heavy chain CDRs of an antibody VH region comprising amino acid sequence SEQ ID NO:24; d) an antibody comprising light chain CDRs of an antibody VL region comprising amino acid sequence SEQ ID NO:31 and heavy chain CDRs of an antibody VH region comprising amino acid sequence SEQ ID NO:32; c) an antibody comprising light chain CDRs of an antibody VL region comprising amino acid sequence SEQ ID NO:39 and heavy chain CDRs of an antibody VH region comprising amino acid sequence SEQ ID NO:40; and f) an antibody comprising light chain CDRs of an antibody VL region comprising amino acid sequence SEQ ID NO:47 and heavy chain CDRs of an antibody VH region comprising amino acid sequence SEQ ID NO:48. The present disclosure provides a humanized antibody specific for complement factor Bb, wherein the antibody is selected from the group consisting of: a) an antibody comprising a light chain variable region comprising amino acid sequences SEQ ID NO:1, SEQ ID NO:2, and SEQ ID NO:3; b) an antibody comprising a heavy chain variable region comprising amino acid sequences SEQ ID NO:4, SEQ ID NO:5, and SEQ ID NO:6; c) an antibody comprising a light chain variable region comprising amino acid sequences SEQ ID NO:9, SEQ ID NO:10, and SEQ ID NO:11; d) an antibody comprising a heavy chain variable region comprising amino acid sequences SEQ ID NO:12, SEQ ID NO:13, and SEQ ID NO:14; e) an antibody comprising a light chain variable region comprising amino acid sequences SEQ ID NO:17, SEQ ID NO:18, and SEQ ID NO:19; f) an antibody comprising a heavy chain variable region comprising amino acid sequences SEQ ID NO:20, SEQ ID NO:21, and SEQ ID NO:22; g) an antibody comprising a light chain variable region comprising amino acid sequences SEQ ID NO:25, SEQ ID NO:26, and SEQ ID NO:27; h) an antibody comprising a heavy chain variable region comprising amino acid sequences SEQ ID NO:28, SEQ ID NO:29, and SEQ ID NO:30; i) an antibody comprising a light chain variable region comprising amino acid sequences SEQ ID NO:33, SEQ ID NO:34, and SEQ ID NO:35; j) an antibody comprising a heavy chain variable region comprising amino acid sequences SEQ ID NO:36, SEQ ID NO:37, and SEQ ID NO:38; k) an antibody comprising a light chain variable region comprising amino acid sequences SEQ ID NO:41, SEQ ID NO:42, and SEQ ID NO:43; and 1) an antibody comprising a heavy chain variable region comprising amino acid sequences SEQ ID NO:44, SEQ ID NO:45, and SEQ ID NO:46. In some cases, the antibody is selected from the group consisting of: a) an antibody comprising a CDR-L1 having amino acid sequence SEQ ID NO:1, a CDR-L2 having amino acid sequence SEQ ID NO:2, a CDR-L3 having amino acid sequence SEQ ID NO:3, a CDR-H1 having amino acid sequence SEQ ID NO:4, a CDR-H2 having amino acid sequence SEQ ID NO:5, and a CDR-H3 having amino acid sequence SEQ ID NO:6; b) an antibody comprising a CDR-L1 having amino acid sequence SEQ ID NO:9, a CDR-L2 having amino acid sequence SEQ ID NO:10, a CDR-L3 having amino acid sequence SEQ ID NO:11, a CDR-H1 having amino acid sequence SEQ ID NO:12, a CDR-H2 having amino acid sequence SEQ ID NO:13, and a CDR-H3 having amino acid sequence SEQ ID NO:14; c) an antibody comprising a CDR-L1 having amino acid sequence SEQ ID NO:17, a CDR-L2 having amino acid sequence SEQ ID NO:18, a CDR-L3 having amino acid sequence SEQ ID NO:19, a CDR-H1 having amino acid sequence SEQ ID NO:20, a CDR-H2 having amino acid sequence SEQ ID NO:21, and a CDR-H3 having amino acid sequence SEQ ID NO:22; d) an antibody comprising a CDR-L1 having amino acid sequence SEQ ID NO:25, a CDR-L2 having amino acid sequence SEQ ID NO:26, a CDR-L3 having amino acid sequence SEQ ID NO:27, a CDR-H1 having amino acid sequence SEQ ID NO:28, a CDR-H2 having amino acid sequence SEQ ID NO:29, and a CDR-H3 having amino acid sequence SEQ ID NO:30; e) an antibody comprising a CDR-L1 having amino acid sequence SEQ ID NO:33, a CDR-L2 having amino acid sequence SEQ ID NO:34, a CDR-L3 having amino acid sequence SEQ ID NO:35, a CDR-H1 having amino acid sequence SEQ ID NO:36, a CDR-H2 having amino acid sequence SEQ ID NO:37, and a CDR-H3 having amino acid sequence SEQ ID NO:38; and f) an antibody comprising a CDR-L1 having amino acid sequence SEQ ID NO:41, a CDR-L2 having amino acid sequence SEQ ID NO:42, a CDR-L3 having amino acid sequence SEQ ID NO:43, a CDR-H1 having amino acid sequence SEQ ID NO:44, a CDR-H2 having amino acid sequence SEQ ID NO:45, and a CDR-H3 having amino acid sequence SEQ ID NO:46. In some cases, the antibody binds a human complement Bb protein with an affinity of at least $10^8$ M. In some cases, the antibody inhibits C3b/Bb-mediated cleavage of C3. In some cases, the antibody comprises a humanized light chain framework region. In some cases, the antibody comprises a humanized heavy chain framework region. In some cases, the antibody comprises a humanized light chain framework region and a humanized heavy chain framework region. In some cases, the antibody is selected from the group consisting of an Ig monomer, a Fab fragment, a F(ab')$_2$ fragment, a Fd fragment, a scFv, a scAb, a dAb, a Fv, a single domain heavy chain antibody, and a single domain light chain antibody. In some cases, the antibody comprises a light chain region and a heavy chain region that are present in separate polypeptides. In some cases, the antibody comprises a light chain region and a heavy chain region that are present in a single polypeptide.

The present disclosure provides a pharmaceutical composition comprising an antibody as described in the preceding paragraph, or elsewhere herein; and a pharmaceutically acceptable excipient. The present disclosure provides a sterile container comprising the pharmaceutical composition.

The present disclosure provides a method of inhibiting C3b/Bb-mediated cleavage of C3 in an individual in need thereof, the method comprising administering to the individual an effective amount of an antibody as described above, or elsewhere herein, or an effective amount of a pharmaceutical composition as described above, or elsewhere herein. In some cases, said administering is intravenous. In some cases, said administering is subcutaneous. In some cases, said administering is intramuscular. The present disclosure provides a method to treat an individual having a complement-mediated disease or disorder, the method comprising administering to the individual an effective amount of an antibody an antibody as described above, or elsewhere herein, or an effective amount of a pharmaceutical composition as described above, or elsewhere herein. In some cases, said administering is intravenous. In some cases, said administering is subcutaneous. In some cases, said administering is intramuscular. In some cases, the administering results in an outcome selected from the group consisting of: a) inhibition of complement alternative pathway (AP) activity; b) inhibition of formation of membrane attack complex; c) inhibition of C3b/Bb-mediated cleavage of C3; d) reduction of the level of C3a and/or C3b in a fluid or tissue; e) inhibition of cleavage of factor B; f) inhibition of AP-mediated cell lysis; g) inhibition of AP-mediated hemolysis; b) inhibition of AP-mediated deposition of C3b, C3d, or other C3 split product on a cell or tissue; i) inhibition of AP-mediated deposition of C3b on red blood cells; j) reduction of the amount of factor Bb in circulation in the individual; k) reduction of the amount of factor Bb in plasma in the individual; and 1) inhibition of production of an anaphylatoxin.

BRIEF DESCRIPTION OF THE DRAWINGS

FIG. 2 depicts EC50 of binding of anti-factor Bb mAbs to factor Bb.

FIG. 4 depicts the ratio of binding of anti-factor Bb mAbs to soluble factor Bb versus soluble factor B; and binding of anti-factor Bb mAbs to factor B by size exclusion chromatography.

FIG. 5 depicts binding affinity of anti-factor Bb mAbs to cynomolgus monkey factor B and factor Bb.

FIG. 9 depicts inhibition of complement AP activity by anti-factor Bb mAbs.

FIG. 12A-12F provide Table 1, which provides amino acid sequences of VH and VL regions, as well as complementarity determining regions (CDRs) of examples of anti-Bb mAbs of the present disclosure.

FIG. 13 provides an amino acid sequence of human factor Bb (SEQ ID NO:49).

FIG. 21 depicts chimeric anti-factor Bb chimeric M10-induced (upper panel) and chimeric anti-factor Bb chimeric M4-induced (lower panel) C3 degradation in cynomolgus monkeys in vivo.

DEFINITIONS

Figure 1:
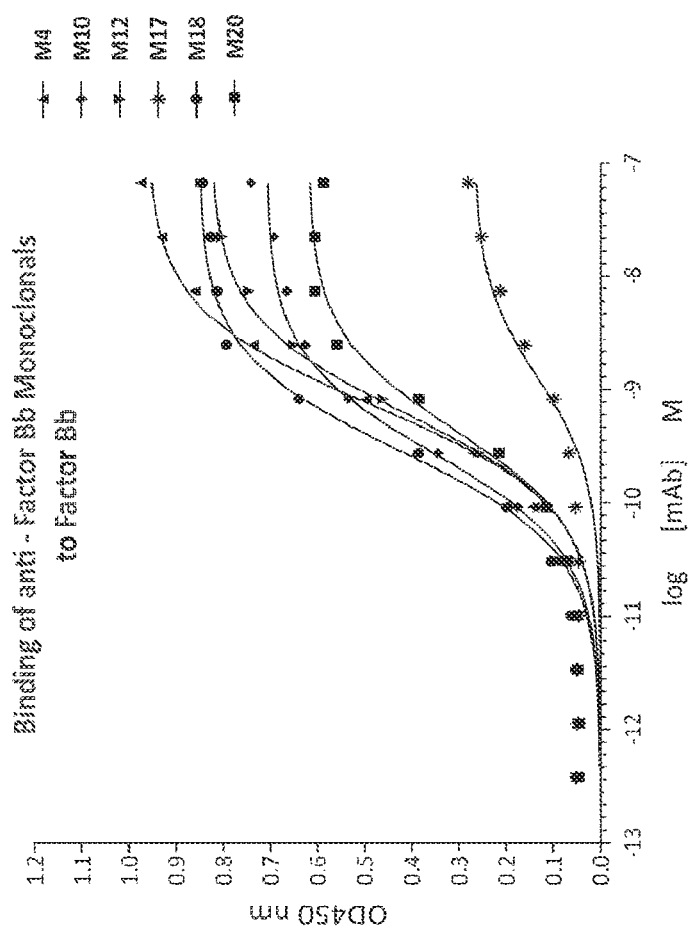
FIG. 1 depicts binding of anti-factor Bb monoclonal antibodies (mAbs) to human factor Bb by enzyme-linked immunosorbent assay (ELISA).

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519, 596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA. IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some cases, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Nat. Acad. Sci. USA* 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. An anti-Bb antibody of the present disclosure binds specifically to an epitope within a complement Bb protein. "Specific binding" refers to binding with an affinity of at least about $10^7$ M or greater, e.g., $5 \times 10^7$ M, $10^8$ M, $5 \times 10^8$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Lefranc et al. (2003) *Developmental and Comparative Immunology* 27:55 (also referred to herein as "Lefranc 2003"); Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., *J. Mol. Biol.* 196:901-917 (1987) (also referred to herein as Chothia 1987); and MacCallum et al., *J. Mol. Biol.* 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth below in Table 2 as a comparison. The CDRs listed in Table 1 (provided in FIG. 12A-12F) were defined in accordance with Lefranc 2003.

TABLE 2

CDR Definitions

| | Kabat[1] | Chothia[2] | MacCallum[3] |
|---|---|---|---|
| $V_H$ CDR-1 | 31-35 | 26-32 | 30-35 |
| $V_H$ CDR-2 | 50-65 | 53-55 | 47-58 |
| $V_H$ CDR-3 | 95-102 | 96-101 | 93-101 |
| $V_L$ CDR-1 | 24-34 | 26-32 | 30-36 |
| $V_L$ CDR-2 | 50-56 | 50-52 | 46-55 |
| $V_L$ CDR-3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In some cases, the antibody is purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. Also encompassed by these terms are any animal that has a complement system, such as mammals, fish, and some invertebrates. As such these terms include complement system-containing mammal, fish, and invertebrate companion animals, agricultural animals, work animals, zoo animals, and lab animals.

A "therapeutically effective amount" or "efficacious amount" refers to the amount of an anti-complement Bb antibody that, when administered to a mammal or other subject for treating a disease, is sufficient to effect such treatment for the disease. The "therapeutically effective amount" will vary depending on the anti-complement Bb antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an anti-Bb antibody" includes a plurality of such antibodies and reference to "the composition" includes reference to one or more compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides anti-complement factor Bb antibodies, and compositions comprising the antibodies. The anti-Bb antibodies are useful for treating complement-mediated disorders. The present disclosure provides methods of treating complement-mediated disorders.

Anti-Complement Bb Antibodies

The present disclosure provides anti-complement Bb antibodies and pharmaceutical compositions comprising such antibodies. An anti-complement Bb antibody of the present disclosure is also referred to herein as an "anti-Bb" antibody or an "anti-factor Bb" antibody. In some cases, an anti-complement Bb antibody of the present disclosure is humanized. In some cases, an anti-complement Bb antibody of the present disclosure comprises at least one humanized light chain variable region (VL) framework region. In some cases, an anti-complement Bb antibody of the present disclosure comprises at least one humanized heavy chain variable region (VH) framework region. In some cases, an anti-complement Bb antibody of the present disclosure comprises at least one humanized VL framework region, and at least one humanized VH framework region.

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIACORE) and/or solid-phase enzyme-linked immunosorbent assay (ELISA) analysis. In many cases, a humanized anti-Bb antibody of the present disclosure does not substantially elicit a HAMA response in a human subject.

Certain amino acids from the human variable region framework residues are selected for substitution based on their possible influence on CDR conformation and/or binding antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, e.g., those sharing at least 60%, at least 70%, at least 80%, at least 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Lefranc et al. (2003) *Developmental and Comparative Immunology* 27:55 (also referred to herein as "Lefranc 2003"); Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody can be selected for substitution into the humanized antibody. Residues that are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids can interact directly with the antigen (Amit et al., Science, 233:747 (1986)) and selecting these amino acids from the donor can be desirable to keep all the antigen contacts that provide affinity in the original antibody.

In some cases, an anti-Bb antibody of the present disclosure comprises a light chain variable region comprising one, two, or three VL CDRs of a M10 antibody, where the CDRs are as defined by Lefranc 2003. In some cases, an anti-Bb antibody of the present disclosure comprises a heavy chain variable region comprising one, two, or three VH CDRs of a M10 antibody, where the CDRs are as defined by Lefranc 2003. In some cases, an anti-Bb antibody of the present disclosure comprises a light chain variable region comprising one, two, or three VL CDRs of a M10 antibody; and a heavy chain variable region comprising one, two, or three VH CDRs of a M10 antibody, where the CDRs are as defined by Lefranc 2003. In some of these embodiments, the anti-Bb antibody includes a humanized $V_H$ and/or a $V_L$ framework region (FR).

In some cases, an anti-Bb antibody of the present disclosure comprises a light chain variable region comprising one, two, or three VL CDRs of a M10 antibody, where the CDRs are as defined by Kabat 1991. In some cases, an anti-Bb antibody of the present disclosure comprises a heavy chain variable region comprising one, two, or three VH CDRs of a M10 antibody, where the CDRs are as defined by Kabat 1991. In some cases, an anti-Bb antibody of the present disclosure comprises a light chain variable region comprising one, two, or three VL CDRs of a M10 antibody; and a heavy chain variable region comprising one, two, or three VH CDRs of a M10 antibody, where the CDRs are as defined by Kabat 1991. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M10 antibody, where the CDRs are as defined by Chothia 1987. In some cases, an anti-Bb antibody of the present disclosure comprises a heavy chain variable region comprising one, two, or three VH CDRs of a M10 antibody, where the CDRs are as defined by Chothia 1987. In some cases, an anti-Bb antibody of the present disclosure comprises a light chain variable region comprising one, two, or three VL CDRs of a M10 antibody; and a heavy chain variable region comprising one, two, or three VH CDRs of a M10 antibody, where the CDRs are as defined by Chothia 1987. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M4 antibody, where the CDRs are as defined by Lefranc 2003. In some cases, an anti-Bb antibody of the present disclosure comprises a heavy chain variable region comprising one, two, or three VH CDRs of a M4 antibody, where the CDRs are as defined by Lefranc 2003. In some cases, an anti-Bb antibody of the present disclosure comprises a light chain variable region comprising one, two, or three VL CDRs of a M4 antibody; and a heavy chain variable region comprising one, two, or three VH CDRs of a M4 antibody, where the CDRs are as defined by Lefranc 2003. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M4 antibody, where the CDRs are as defined by Kabat 1991. In some cases, an anti-Bb antibody of the present disclosure comprises a heavy chain variable region comprising one, two, or three VH CDRs of a M4 antibody, where the CDRs are as defined by Kabat 1991. In some cases, an anti-Bb antibody of the present disclosure comprises a light chain variable region comprising one, two, or three VL CDRs of a M4 antibody; and a heavy chain variable region comprising one, two, or three VH CDRs of a M4 antibody, where the CDRs are as defined by Kabat 1991. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M4 antibody, where the CDRs are as defined by Chothia 1987. In some cases, an anti-Bb antibody of the present disclosure comprises a heavy chain variable region comprising one, two, or three VH CDRs of a M4 antibody, where the CDRs are as defined by Chothia 1987. In some cases, an anti-Bb antibody of the present disclosure comprises a light chain variable region comprising one, two, or three VL CDRs of a M4 antibody; and a heavy chain variable region comprising one, two, or three VH CDRs of a M4 antibody, where the CDRs are as defined by Chothia 1987. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M20 antibody, where the CDRs are as defined by Lefranc 2003. In some cases, an anti-Bb antibody of the present disclosure comprises a heavy chain variable region comprising one, two, or three VH CDRs of a M20 antibody, where the CDRs are as defined by Lefranc 2003. In some cases, an anti-Bb antibody of the present disclosure comprises a light chain variable region comprising one, two, or three VL CDRs of a M20 antibody; and a heavy chain variable region comprising one, two, or three VH CDRs of a M20 antibody, where the CDRs are as defined by Lefranc 2003. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M20 antibody, where the CDRs are as defined by Kabat 1991. In some cases, an anti-Bb antibody of the present disclosure comprises a heavy chain variable region comprising one, two, or three VH CDRs of a M20 antibody, where the CDRs are as defined by Kabat 1991. In some cases, an anti-Bb antibody of the present disclosure comprises a light chain variable region comprising one, two, or three VL CDRs of a M20 antibody; and a heavy chain variable region comprising one, two, or three VH CDRs of a M20 antibody, where the CDRs are as defined by Kabat 1991. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M20 antibody, where the CDRs are as defined by Chothia 1987. In some cases, an anti-Bb antibody of the present disclosure comprises a heavy chain variable region comprising one, two, or three VH CDRs of a M20 antibody, where the CDRs are as defined by Chothia 1987. In some cases, an anti-Bb antibody of the present disclosure comprises a light chain variable region comprising one, two, or three VL CDRs of a M20 antibody; and a heavy chain variable region comprising one, two, or three VH CDRs of a M20 antibody, where the CDRs are as defined by Chothia 1987. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M17 antibody, where the CDRs are as defined by Lefranc 2003. In some cases, an anti-Bb antibody of the present disclosure comprises a heavy chain variable region comprising one, two, or three VH CDRs of a M17 antibody, where the CDRs are as defined by Lefranc 2003. In some cases, an anti-Bb antibody of the present disclosure comprises a light chain variable region comprising one, two, or three VL CDRs of a M17 antibody; and a heavy chain variable region comprising one, two, or three VH CDRs of a M17 antibody, where the CDRs are as defined by Lefranc 2003. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M17 antibody, where the CDRs are as defined by Kabat 1991. In some cases, an anti-Bb antibody of the present disclosure comprises a heavy chain variable region comprising one, two, or three VH CDRs of a M17 antibody, where the CDRs are as defined by Kabat 1991. In some cases, an anti-Bb antibody of the present disclosure comprises a light chain variable region comprising one, two, or three VL CDRs of a M17 antibody; and a heavy chain variable region comprising one, two, or three VH CDRs of a M17 antibody, where the CDRs are as defined by Kabat 1991. In some of these embodiments, the anti-Bb antibody includes a humanized $V_H$ and/or a $V_L$ framework region.

In some cases, an anti-Bb antibody of the present disclosure comprises a light chain variable region comprising one, two, or three VL CDRs of a M17 antibody, where the CDR % are as defined by Chothia 1987. In some cases, an anti-Bb antibody of the present disclosure comprises a heavy chain variable region comprising one, two, or three VH CDRs of a M17 antibody, where the CDRs are as defined by Chothia 1987. In some cases, an anti-Bb antibody of the present disclosure comprises a light chain variable region comprising one, two, or three VL CDRs of a M17 antibody; and a heavy chain variable region comprising one, two, or three VH CDRs of a M17 antibody, where the CDRs are as defined by Chothia 1987. In some of these embodiments, the anti-Bb antibody includes a humanized $V_H$ and/or a $V_L$ framework region.

In some cases, an anti-Bb antibody of the present disclosure comprises a light chain region comprising one, two, or three CDRs selected from SEQ ID NO:1, SEQ ID NO:2, and SEQ ID NO:3. In some cases, an anti-Bb antibody of the present disclosure comprises a heavy chain region comprising one, two, or three CDRs selected from SEQ ID NO:4, SEQ ID NO:5, and SEQ ID NO: 6. In some cases, an anti-Bb antibody of the present disclosure comprises: a) a light chain region comprising one, two, or three CDRs selected from SEQ ID NO:1, SEQ ID NO:2, and SEQ ID NO:3; and b) a heavy chain region comprising one, two, or three CDRs selected from SEQ ID NO:4, SEQ ID NO:5, and SEQ ID NO: 6. In some of these embodiments, the anti-Bb antibody includes a humanized $V_H$ and/or a $V_L$ framework region.

In some cases, an anti-Bb antibody of the present disclosure comprises a light chain region comprising one, two, or three CDRs selected from SEQ ID NO:9, SEQ ID NO:10, and SEQ ID NO:11. In some cases, an anti-Bb antibody of the present disclosure comprises a heavy chain region comprising one, two, or three CDRs selected from SEQ ID NO:12, SEQ ID NO:13, and SEQ ID NO: 14. In some cases, an anti-Bb antibody of the present disclosure comprises: a) a light chain region comprising one, two, or three CDRs selected from SEQ ID NO:9, SEQ ID NO:10, and SEQ ID NO: 11; and b) a heavy chain region comprising one, two, or three CDRs selected from SEQ ID NO:12, SEQ ID NO:13, and SEQ ID NO: 14. In some of these embodiments, the anti-Bb antibody includes a humanized $V_H$ and/or a $V_L$ framework region.

In some cases, an anti-Bb antibody of the present disclosure comprises a light chain region comprising one, two, or three CDRs selected from SEQ ID NO:17, SEQ ID NO:18, and SEQ ID NO:19. In some cases, an anti-Bb antibody of the present disclosure comprises a heavy chain region comprising one, two, or three CDRs selected from SEQ ID NO:20, SEQ ID NO:21, and SEQ ID NO:22. In some cases, an anti-Bb antibody of the present disclosure comprises: a) a light chain region comprising one, two, or three CDRs selected from SEQ ID NO:17, SEQ ID NO:18, and SEQ ID NO:19; and b) a heavy chain region comprising one, two, or three CDRs selected from SEQ ID NO:20, SEQ ID NO:21, and SEQ ID NO:22. In some of these embodiments, the anti-Bb antibody includes a humanized $V_H$ and/or a $V_1$ framework region.

In some cases, an anti-Bb antibody of the present disclosure comprises a light chain region comprising one, two, or three CDRs selected from SEQ ID NO:25, SEQ ID NO:2, and SEQ ID NO:26. In some cases, an anti-Bb antibody of the present disclosure comprises a heavy chain region comprising one, two, or three CDRs selected from SEQ ID NO:27. SEQ ID NO:28, and SEQ ID NO:29. In some cases, an anti-Bb antibody of the present disclosure comprises: a)

a light chain region comprising one, two, or three CDRs selected from SEQ ID NO:25, SEQ ID NO:2, and SEQ ID NO:26; and h) a heavy chain region comprising one, two, or three CDRs selected from SEQ ID NO:27, SEQ ID NO:28, and SEQ ID NO:29. In some of these embodiments, the anti-Bb antibody includes a humanized $V_H$ and/or a $V_L$ framework region.

In some cases, a humanized $V_H$ framework or $V_L$ framework is a consensus human framework. A consensus humanized framework can represent the most commonly occurring amino acid residue in a selection of human immunoglobulin $V_L$ or $V_H$ framework sequences.

Non-limiting examples of consensus human $V_H$ framework regions suitable for use with $V_H$ CDRs as described herein include (subgroup III consensus):
  a) $V_H$ FR1: EVQLVESGGOLVQPGGSLRLSCAAS (SEQ ID NO:50);
  b) $V_H$ FR2: WVRQAPGKGLEWV (SEQ ID NO:51);
  c) $V_H$ FR3: RFTISRDNSKNTLYLQMNSLRAEDTAVYYC (SEQ ID NO:52); and
  d) $V_H$ FR4: WGQGTLVTVSS (SEQ ID NO:54).

In some cases, $V_H$ FR3 comprises an amino acid substitution at position 71, 73, and/or 78; e.g., where the underlined and bolded R in RFTISRDNSKNTLYLQMNSLRAEDTAVYYC (SEQ ID NO:52) is amino acid 71 (Kabat numbering); the underlined and bolded N in RFTISRDNSKNTLYLQMNSLRAEDTAVYYC (SEQ ID NO:52) is amino acid 73 (Kabat numbering); and the underlined and bolded L in RFTISRDNSKNTLYLOMNSLRAEDTAVYYC (SEQ ID NO:52) is amino acid 78 (Kabat numbering). For example, in some cases, amino acid 71 is A; and/or amino acid 73 is T; and/or amino acid 78 is A. As an example, in some cases, a suitable consensus humanized $V_H$ FR3 comprises the amino acid sequence: RFTISADTSKNTAYLQMNSLRAEDTAVYYC (SEQ ID NO:54).

Non-limiting examples of consensus human $V_H$ framework regions suitable for use with $V_H$ CDRs as described herein include (subgroup I consensus):
  a) $V_H$ FR1: QVQLVQSGAEVKKPGASVKVSCKAS (SEQ ID NO:55);
  b) $V_H$ FR2: WVRQAPGQGLEWM (SEQ ID NO:56);
  c) $V_H$ FR3: RVTITADTSTSTAYMELSSLRSEDTAVYYC (SEQ ID NO:57); and
  d) $V_H$ FR4: WGQGTLVTVSS (SEQ ID NO:58).

Non-limiting examples of the consensus human $V_H$ framework regions suitable for use with $V_H$ CDRs as described herein include (subgroup II consensus):
  a) $V_H$ FR1: QVQLQESGPGLVKPSQTLSLTCTVS (SEQ ID NO:59);
  b) $V_H$ FR2: WIRQPPGKGLEWI (SEQ ID NO:60);
  c) $V_H$ FR3: RVTISVDTSKNQFSLKLSSVTAADTAVYYC (SEQ ID NO:61); and
  d) $V_H$ FR4: WGQGTLVTVSS (SEQ ID NO:62).

Non-limiting examples of consensus human $V_L$ framework regions suitable for use with $V_L$ CDRs as described herein include (subgroup I consensus):
  a) $V_L$ FR1: DIQMTQSPSSLSASVGDRVTITC (SEQ ID NO:63);
  b) $V_L$ FR2: WYQQKPGKAPKLLIY (SEQ ID NO:64);
  c) $V_L$ FR3: GVPSRFSGSGSGTDFTLTISSLQPEDFATYYC (SEQ ID NO:65); and
  d) $V_L$ FR4: FGQGTKVEIK (SEQ ID NO:66).

Non-limiting examples of consensus human $V_L$ framework regions suitable for use with $V_L$ CDRs as described herein include (subgroup II consensus):
  a) $V_L$ FR1: DIVMTQSPLSLPVTPGEPASISC (SEQ ID NO:67);
  b) $V_L$ FR2: WYLQKPGQSPQLLIY (SEQ ID NO:68);
  c) $V_L$ FR3: GVPDRFSGSGSGTDFTLKISRVEAEDVGVYYC (SEQ ID NO:69); and
  d) $V_L$ FR4: FGQGTKVEIK (SEQ ID NO:70).

Non-limiting examples of consensus human $V_L$ framework regions suitable for use with $V_L$ CDRs as described herein include (subgroup III consensus):
  a) $V_L$ FR1: DIVMTQSPDSLAVSLGERATINC (SEQ ID NO:71);
  b) $V_L$ FR2: WYQQKPGQPPKLLIY (SEQ ID NO:72);
  c) $V_L$ FR3: GVPDRFSGSGSGTDFTLTISSLQAEDFAVYYC (SEQ ID NO:73): and
  d) $V_L$ FR4: FGQGTKVEIK (SEQ ID NO:74).

Non-limiting examples of consensus human $V_L$ framework regions suitable for use with $V_L$ CDRs as described herein include (subgroup IV consensus):
  a) $V_L$ FR1: DIVMTQSPDSLAVSLGERATINC (SEQ ID NO:71);
  b) $V_L$ FR2: WYQQKPGQPPKLLIY (SEQ ID NO:72);
  c) $V_L$ FR3: GVPDRFSGSGSGTDFTLTISSLQAEDFAVYYC (SEQ ID NO:73); and
  d) $V_L$ FR4: FGQGTKVEIK (SEQ ID NO:74).

In some cases, an anti-Bb antibody of the present disclosure comprises alight chain variable region comprising amino acid sequences SEQ ID NO: 1, SEQ ID NO:2, and SEQ ID NO:3.

In some cases, an anti-Bb antibody of the present disclosure comprises a heavy chain variable region comprising amino acid sequences SEQ ID NO:4, SEQ ID NO:5, and SEQ ID NO:6.

In some cases, an anti-Bb antibody of the present disclosure comprises alight chain variable region comprising amino acid sequences SEQ ID NO:9, SEQ ID NO: 10, and SEQ ID NO: 11.

In some cases, an anti-Bb antibody of the present disclosure comprises a heavy chain variable region comprising amino acid sequences SEQ ID NO: 12, SEQ ID NO: 13, and SEQ ID NO: 14.

In some cases, an anti-Bb antibody of the present disclosure comprises a light chain variable region comprising amino acid sequences SEQ ID NO:17, SEQ ID NO:18, and SEQ ID NO:19.

In some cases, an anti-Bb antibody of the present disclosure comprises a heavy chain variable region comprising amino acid sequences SEQ ID NO:20, SEQ ID NO:21, and SEQ ID NO:22.

In some cases, an anti-Bb antibody of the present disclosure comprises a light chain variable region comprising amino acid sequences SEQ ID NO:25, SEQ ID NO:2, and SEQ ID NO:26.

In some cases, an anti-Bb antibody of the present disclosure comprises a heavy chain variable region comprising amino acid sequences SEQ ID NO:27, SEQ ID NO:28, and SEQ ID NO:29.

In some cases, an anti-Bb antibody of the present disclosure comprises a CDR-L1 having amino acid sequence SEQ ID NO:1, a CDR-L2 having amino acid sequence SEQ ID NO:2, a CDR-L3 having amino acid sequence SEQ ID NO:3, a CDR-H1 having amino acid sequence SEQ ID NO:4, a CDR-H2 having amino acid sequence SEQ ID NO:5, and a CDR-H3 having amino acid sequence SEQ ID NO:6.

In some cases, an anti-Bb antibody of the present disclosure comprises a CDR-L1 having amino acid sequence SEQ ID NO:9, a CDR-L2 having amino acid sequence SEQ ID NO:10, a CDR-L3 having amino acid sequence SEQ ID NO: 11, a CDR-H1 having amino acid sequence SEQ ID NO:12, a CDR-H2 having amino acid sequence SEQ ID NO:13, and a CDR-H3 having amino acid sequence SEQ ID NO:14.

In some cases, an anti-Bb antibody of the present disclosure comprises a CDR-L1 having amino acid sequence SEQ ID NO:17, a CDR-L2 having amino acid sequence SEQ ID NO:18, a CDR-L3 having amino acid sequence SEQ ID NO:19, a CDR-H1 having amino acid sequence SEQ ID NO:20, a CDR-H2 having amino acid sequence SEQ ID NO:21, and a CDR-H3 having amino acid sequence SEQ ID NO:22.

In some cases, an anti-Bb antibody of the present disclosure comprises a CDR-L1 having amino acid sequence SEQ ID NO:25, a CDR-L2 having amino acid sequence SEQ ID NO:2, a CDR-L3 having amino acid sequence SEQ ID NO:26, a CDR-H1 having amino acid sequence SEQ ID NO:27, a CDR-H2 having amino acid sequence SEQ ID NO:28, and a CDR-H3 having amino acid sequence SEQ ID NO:29.

In some cases, an anti-Bb antibody of the present disclosure comprises a light chain variable region comprising an amino acid sequence that is 85%, 86%, 87%, 88%, 89%, 90%, 91%, 92%, 93%, 94%, 95%, 96%, 97%, 98% or 99% identical to an amino acid sequence selected from the group consisting of SEQ ID NO:7, SEQ ID NO:15, SEQ ID NO:23, and SEQ ID NO:30.

In some cases, an anti-Bb antibody of the present disclosure comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:7.

In some cases, an anti-Bb antibody of the present disclosure comprises a light chain variable region comprising an amino acid sequence that is 85%, 86%, 87%, 88%, 89%, 90%91%, 92%, 93%, 94%, 95%, 96%, 97%, 98% or 99% identical to the amino acid sequence set forth in SEQ ID NO:15.

In some cases, an anti-Bb antibody of the present disclosure comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:23.

In some cases, an anti-Bb antibody of the present disclosure comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:30.

In some cases, an anti-Bb antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to an amino acid sequence selected from the group consisting of SEQ ID NO:8, SEQ ID NO:16, SEQ ID NO:24, and SEQ ID NO:31.

In some cases, an anti-Bb antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:8.

In some cases, an anti-Bb antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:16.

In some cases, an anti-Bb antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:24.

In some cases, an anti-Bb antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:31.

In some cases, an anti-Bb antibody of the present disclosure comprises a light chain variable region comprising an amino acid sequence that is 90% identical to amino acid sequence SEQ ID NO:7.

In some cases, an anti-Bb antibody of the present disclosure comprises a light chain variable region comprising an amino acid sequence that is 90% identical to amino acid sequence SEQ ID NO:15.

In some cases, an anti-Bb antibody of the present disclosure comprises a light chain variable region comprising an amino acid sequence that is 90% identical to amino acid sequence SEQ ID NO:23.

In some cases, an anti-Bb antibody of the present disclosure comprises a light chain variable region comprising an amino acid sequence that is 90% identical to amino acid sequence SEQ ID NO:30.

In some cases, an anti-Bb antibody of the present disclosure comprises a heavy chain variable region comprising an amino acid sequence that is 90% identical to amino acid sequence SEQ ID NO:8.

In some cases, an anti-Bb antibody of the present disclosure comprises a heavy chain variable region comprising an amino acid sequence that is 90% identical to amino acid sequence SEQ ID NO:16.

In some cases, an anti-Bb antibody of the present disclosure comprises a heavy chain variable region comprising an amino acid sequence that is 90% identical to amino acid sequence SEQ ID NO:24.

In some cases, an anti-Bb antibody of the present disclosure comprises a heavy chain variable region comprising an amino acid sequence that is 90% identical to amino acid sequence SEQ ID NO:31.

In some cases, an anti-Bb antibody of the present disclosure comprises a light chain variable region comprising an amino acid sequence that is 95% identical to amino acid sequence SEQ ID NO:7.

In some cases, an anti-Bb antibody of the present disclosure comprises a light chain variable region comprising an amino acid sequence that is 95% identical to amino acid sequence SEQ ID NO:15.

In some cases, an anti-Bb antibody of the present disclosure comprises a light chain variable region comprising an amino acid sequence that is 95% identical to amino acid sequence SEQ ID NO:23.

In some cases, an anti-Bb antibody of the present disclosure comprises a light chain variable region comprising an amino acid sequence that is 95% identical to amino acid sequence SEQ ID NO:30.

In some cases, an anti-Bb antibody of the present disclosure comprises a heavy chain variable region comprising an amino acid sequence that is 95% identical to amino acid sequence SEQ ID NO:8.

In some cases, an anti-Bb antibody of the present disclosure comprises a heavy chain variable region comprising an amino acid sequence that is 95% identical to amino acid sequence SEQ ID NO:16.

In some cases, an anti-Bb antibody of the present disclosure comprises a heavy chain variable region comprising an amino acid sequence that is 95% identical to amino acid sequence SEQ ID NO:24.

In some cases, an anti-Bb antibody of the present disclosure comprises a heavy chain variable region comprising an amino acid sequence that is 95% identical to amino acid sequence SEQ ID NO:31.

In some cases, an anti-Bb antibody of the present disclosure comprises a light chain variable region comprising amino acid sequence SEQ ID NO:7.

In some cases, an anti-Bb antibody of the present disclosure comprises a heavy chain variable region comprising amino acid sequence SEQ ID NO:8.

In some cases, an anti-Bb antibody of the present disclosure comprises a light chain variable region comprising amino acid sequence SEQ ID NO:15.

In some cases, an anti-Bb antibody of the present disclosure comprises a heavy chain variable region comprising amino acid sequence SEQ ID NO:16.

In some cases, an anti-Bb antibody of the present disclosure comprises a light chain variable region comprising amino acid sequence SEQ ID NO:23.

In some cases, an anti-Bb antibody of the present disclosure comprises a heavy chain variable region comprising amino acid sequence SEQ ID NO:24.

In some cases, an anti-Bb antibody of the present disclosure comprises a light chain variable region comprising amino acid sequence SEQ ID NO:30.

In some cases, an anti-Bb antibody of the present disclosure comprises a heavy chain variable region comprising amino acid sequence SEQ ID NO:31.

In some cases, an anti-Bb antibody of the present disclosure comprises a light chain variable region comprising an amino acid sequence that is 90% identical to amino acid sequence SEQ ID NO:7 and a heavy chain variable region comprising an amino acid sequence that is 90% identical to amino acid sequence SEQ ID NO:8.

In some cases, an anti-Bb antibody of the present disclosure comprises a light chain variable region comprising an amino acid sequence that is 90% identical to amino acid sequence SEQ ID NO:15 and a heavy chain variable region comprising an amino acid sequence that is 90% identical to amino acid sequence SEQ ID NO:16.

In some cases, an anti-Bb antibody of the present disclosure comprises a light chain variable region comprising an amino acid sequence that is 90% identical to amino acid sequence SEQ ID NO:23 and a heavy chain variable region comprising an amino acid sequence that is 90% identical to amino acid sequence SEQ ID NO:24.

In some cases, an anti-Bb antibody of the present disclosure comprises a light chain variable region comprising an amino acid sequence that is 90% identical to amino acid sequence SEQ ID NO:30 and a heavy chain variable region comprising an amino acid sequence that is 90% identical to amino acid sequence SEQ ID NO:31.

In some cases, an anti-Bb antibody of the present disclosure comprises a light chain variable region comprising an amino acid sequence that is 95% identical to amino acid sequence SEQ ID NO:7 and a heavy chain variable region comprising an amino acid sequence that is 95% identical to amino acid sequence SEQ ID NO:8.

In some cases, an anti-Bb antibody of the present disclosure comprises a light chain variable region comprising an amino acid sequence that is 95% identical to amino acid sequence SEQ ID NO:15 and a heavy chain variable region comprising an amino acid sequence that is 95% identical to amino acid sequence SEQ ID NO:16.

In some cases, an anti-Bb antibody of the present disclosure comprises a light chain variable region comprising an amino acid sequence that is 95% identical to amino acid sequence SEQ ID NO:23 and a heavy chain variable region comprising an amino acid sequence that is 95% identical to amino acid sequence SEQ ID NO:24.

In some cases, an anti-Bb antibody of the present disclosure comprises a light chain variable region comprising an amino acid sequence that is 95% identical to amino acid sequence SEQ ID NO:30 and a heavy chain variable region comprising an amino acid sequence that is 95% identical to amino acid sequence SEQ ID NO:31.

In some cases, an anti-Bb antibody of the present disclosure comprises a light chain variable region comprising amino acid sequence SEQ ID NO:7 and a heavy chain variable region comprising amino acid sequence SEQ ID NO:8.

In some cases, an anti-Bb antibody of the present disclosure comprises a light chain variable region comprising amino acid sequence SEQ ID NO:15 and a heavy chain variable region comprising amino acid sequence SEQ ID NO:16.

In some cases, an anti-Bb antibody of the present disclosure comprises a light chain variable region comprising amino acid sequence SEQ ID NO:23 and a heavy chain variable region comprising amino acid sequence SEQ ID NO:24.

In some cases, an anti-Bb antibody of the present disclosure comprises a light chain variable region comprising amino acid sequence SEQ ID NO:30 and a heavy chain variable region comprising amino acid sequence SEQ ID NO:31.

In some cases, an anti-Bb antibody of the present disclosure specifically binds an epitope within a complement Bb protein, wherein the antibody competes for binding the epitope with an antibody that comprises light chain CDRs of an antibody light chain variable region comprising amino acid sequence SEQ ID NO:7 and heavy chain CDRs of an antibody heavy chain variable region comprising amino acid sequence SEQ ID NO:8.

In some cases, an anti-Bb antibody of the present disclosure specifically binds an epitope within a complement Bb protein, wherein the antibody competes for binding the epitope with an antibody that comprises light chain CDRs of an antibody light chain variable region comprising amino acid sequence SEQ ID NO:15 and heavy chain CDRs of an antibody heavy chain variable region comprising amino acid sequence SEQ ID NO:16.

In some cases, an anti-Bb antibody of the present disclosure specifically binds an epitope within a complement Bb protein, wherein the antibody competes for binding the epitope with an antibody that comprises light chain CDRs of an antibody light chain variable region comprising amino acid sequence SEQ ID NO:23 and heavy chain CDRs of an antibody heavy chain variable region comprising amino acid sequence SEQ ID NO:24.

In some cases, an anti-Bb antibody of the present disclosure specifically binds an epitope within a complement Bb protein, wherein the antibody competes for binding the epitope with an antibody that comprises light chain CDRs of an antibody light chain variable region comprising amino acid sequence SEQ ID NO:30 and heavy chain CDRs of an antibody heavy chain variable region comprising amino acid sequence SEQ ID NO:31.

In some cases, an anti-Bb antibody of the present disclosure comprises light chain CDRs of an antibody light chain variable region comprising amino acid sequence SEQ ID NO:7 and heavy chain CDRs of an antibody heavy chain variable region comprising amino acid sequence SEQ ID NO:8.

In some cases, an anti-Bb antibody of the present disclosure comprises light chain CDRs of an antibody light chain variable region comprising amino acid sequence SEQ ID NO:15 and heavy chain CDRs of an antibody heavy chain variable region comprising amino acid sequence SEQ ID NO:16.

In some cases, an anti-Bb antibody of the present disclosure comprises light chain CDRs of an antibody light chain variable region comprising amino acid sequence SEQ ID NO:23 and heavy chain CDRs of an antibody heavy chain variable region comprising amino acid sequence SEQ ID NO:24.

In some cases, an anti-Bb antibody of the present disclosure comprises light chain CDRs of an antibody light chain variable region comprising amino acid sequence SEQ ID NO:30 and heavy chain CDRs of an antibody heavy chain variable region comprising amino acid sequence SEQ ID NO:31.

In some cases, an anti-Bb antibody of the present disclosure binds a complement Bb protein from an individual that has a complement system. In some embodiments, an anti-Bb antibody of the present disclosure binds a complement Bb protein from a mammal, fish, or invertebrate that has a complement system. In some embodiments, an anti-Bb antibody of the present disclosure binds a mammalian complement Bb protein. In some embodiments, an anti-Bb antibody of the present disclosure binds a human complement Bb protein. In some embodiments, an anti-Bb antibody of the present disclosure binds a complement Bb protein having amino acids 26-259 of the amino acid sequence depicted in FIG. 13. FIG. 13 provides an amino acid sequence of a *Homo sapiens* complement Bb protein; amino acids 26-259 are the mature protein.

In some cases, an anti-Bb antibody of the present disclosure binds a complement Bb protein with an affinity of from $10^{-8}$ M to $10^{-9}$ M, from $10^{-9}$ M to $10^{-10}$ M, or from $10^{-10}$ M to $10^{-11}$ M.

In some cases, an anti-Bb antibody of the present disclosure exhibits preferential binding for factor Bb, compared with binding of the anti-Bb antibody for factor B. In some cases, an anti-Bb antibody of the present disclosure binds to factor Bb, but does not substantially bind to soluble Factor B. In some cases, an anti-Bb antibody of the present disclosure binds to factor Bb with an affinity that is at least 2-fold, at least 2.5-fold, at least 3-fold, at least 4-fold, at least 5-fold, at least 7.5-fold, at least 10-fold, at least 15-fold, at least 20-fold, at least 25-fold, at least 50-fold, at least 75-fold, or at least 100-fold, higher than the affinity of the antibody for factor B. In some cases, an anti-Bb antibody of the present disclosure binds to factor Bb with an affinity that is from 2-fold to 2.5-fold, from 2.5-fold to 5-fold, from 5-fold to 10-fold, from 10-fold to 15-fold, from 15-fold to 20-fold, from 20-fold to 25-fold, from 25-fold to 50-fold, from 50-fold to 75-fold, or from 75-fold to 100-fold, higher than the affinity of the antibody for factor B. In some cases, the ratio of i) binding of an anti-Bb antibody of the present disclosure to factor Bb to ii) the binding of an anti-Bb antibody of the present disclosure to factor B is at least 2:1, at least 5:1, at least 10:1, at least 25:1, at least 50:1, at least 75:1, or at least 100:1. In some cases, the ratio of i) binding of an anti-Bb antibody of the present disclosure to factor Bb to ii) the binding of an anti-Bb antibody of the present disclosure to factor B is from 2:1 to 5:1, from 5:1 to 10:1, from 10:1 to 25:1, from 25:1 to 50:1, from 50:1 to 75:1, or from 75:1 to 100:1.

In some cases, an anti-Bb antibody of the present disclosure binds both factor B and factor Bb.

In some cases, an anti-Bb antibody of the present disclosure inhibits alternative pathway (AP) activity by at least 10%, at least 20%, at least 30%, at least 40%, at least 50%, at least 60%, at least 65%, at least 70%, at least 75%, at least 80%, at least 85%, at least 90%, at least 95%, or 100%, compared to the level of AP activity in the absence of the anti-Bb antibody. In some cases, an anti-Bb antibody of the present disclosure inhibits AP activity with an $IC_{50}$ of from $10^{-7}$ M to $10^{-9}$ M, e.g., an $IC_{50}$ of from $10^{-7}$ M to $5\times10^{-7}$ M, from $5\times10^{-7}$ M to $10^{-8}$ M, from $10^{-10}$ M to $5\times10^{-8}$ M, or from $5\times10^{-8}$ M to $10^{-9}$ M.

In some cases, an anti-Bb antibody of the present disclosure inhibits formation of membrane attack complex (MAC) by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of MAC formed in the absence of the anti-Bb antibody.

In some cases, an anti-Bb antibody of the present disclosure inhibits C3b/Bb-mediated cleavage of C3. C3b/Bb is also known as "C3 convertase." In some cases, an anti-Bb antibody of the present disclosure inhibits C3b/Bb-mediated cleavage of C3 by at least 10%, at least 20%, at least 30%, at least 40%, at least 50%, at least 60%, at least 65%, at least 70%, at least 75%, at least 80%, at least 85%, at least 90%, at least 95%, or 100%, compared to the cleavage of C3 in the absence of the anti-Bb antibody. In some cases, an anti-Bb antibody of the present disclosure inhibits C3b/Bb-mediated cleavage of C3 with an $IC_{50}$ of from $10^7$ M to $10^9$ M, e.g., an $IC_{50}$ of from $10^{-7}$ M to $5\times10^{-7}$ M, from $5\times10^{-7}$ M to $10^{-8}$ M, from $10^{-8}$ M to $5\times10^{-8}$ M, or from $5\times10^{-8}$ M to $10^{-9}$ M.

In some cases, an anti-Bb antibody of the present disclosure inhibits C3b/Bb-mediated cleavage of C3, thereby reducing production of a C3 cleavage product. For example, in some cases, an anti-Bb antibody of the present disclosure inhibits C3b/Bb-mediated cleavage of C3, thereby reducing production of a C3 cleavage product (e.g., C3a and/or C3b) by at least 10%, at least 20%, at least 30%, at least 40%, at least 50%, at least 60%, at least 65%, at least 70%, at least 75%, at least 80%, at least 85%, at least 90%, at least 95%, or 100%, compared to the production of the C3 cleavage product in the absence of the anti-Bb antibody. In some cases, an anti-Bb antibody of the present disclosure that inhibits C3b/Bb-mediated cleavage of C3 comprises VH and VL CDRs present in M17 VH and VL, respectively. In some cases, an anti-Bb antibody of the present disclosure that inhibits C3b/Bb-mediated cleavage of C3 comprises VH and VL CDRs present in M10 VH and VL, respectively.

In some cases, an anti-Bb antibody of the present disclosure binds factor B and inhibits cleavage of factor B. For example, in some cases, an anti-Bb antibody of the present disclosure inhibits factor B cleavage by at least 10%, at least 20%, at least 30%, at least 40%, at least 50%, at least 60%, at least 65%, at least 70%, at least 75%, at least 80%, at least 85%, at least 90%, at least 95%, or more than 95%, compared to factor B cleavage in the absence of the anti-Bb antibody. In some cases, an anti-Bb antibody of the present disclosure inhibits C3b/Bb formation.

In some cases, an anti-Bb antibody of the present disclosure inhibits complement AP-mediated cell lysis by at least 10%, at least 20%, at least 30%, at least 40%, at least 50%, at least 60%, at least 65%, at least 70%, at least 75%, at least 80%, at least 85%, at least 90%, at least 95%, or 100%, compared to the degree of cell lysis in the absence of the anti-Bb antibody. A cell lysis assay can be used to determine the degree of inhibition of AP-mediated cell lysis. In some cases, an anti-Bb antibody of the present disclosure inhibits AP-mediated cell lysis with an IC of from $10^{-7}$ M to $10^{-9}$ M, e.g., an ICs of from $10^{-7}$ M to $5 \times 10^{-7}$ M, from $5 \times 10^{-8}$ M to $10^{-8}$ M, from $10^9$ M to $5 \times 10^{-8}$ M, or from $5 \times 10^{-8}$ M to $10^9$ M.

In some cases, an anti-Bb antibody of the present disclosure inhibits complement AP-mediated hemolysis by at least 10%, at least 20%, at least 30%, at least 40%, at least 50%, at least 60%, at least 65%, at least 70%, at least 75%, at least 80%, at least 85%, at least 90%, at least 95%, or 100%, compared to the degree of hemolysis in the absence of the anti-Bb antibody. A rabbit red blood cell (RBC) hemolysis assay can be used to determine the degree of inhibition of AP-mediated hemolysis. In some cases, an anti-Bb antibody of the present disclosure inhibits AP-mediated hemolysis with an $IC_{50}$ of from $10^{-7}$ M to $10^{-9}$ M, e.g., an $IC_{50}$ of from $10^{-7}$ M to $5 \times 10^7$ M, from $5 \times 10^{-7}$ M to $10^{-8}$ M, from $10^{-8}$ M to $5 \times 10^{-8}$ M, or from $5 \times 10^{-8}$ M to $10^{-9}$ M.

In some cases, an anti-Bb antibody of the present disclosure inhibits AP-mediated deposition of C3b, C3d, or other C3 split product on a cell or tissue. For example, in some cases, an anti-Bb antibody of the present disclosure inhibits AP-mediated deposition of C3b, C3d, or other C3 split product on a cell or tissue by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of deposition of C3b, C3d, or other C3 split product on the cell or tissue in the absence of administration of the anti-Bb antibody, or before administration of the anti-Bb antibody. In some cases, an anti-Bb antibody of the present disclosure inhibits AP-mediated deposition of C3b, C3d, or other C3 split product on a cell or tissue with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^{-8}$ M to $5 \times 10^{-8}$ M, or from $5 \times 10^{-8}$ M to $10^{-9}$ M.

In some cases, an anti-Bb antibody of the present disclosure inhibits AP-mediated C3b deposition on a cell or tissue by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C3b deposition on the cell or tissue in the absence of the anti-Bb antibody. In some cases, an anti-Bb antibody of the present disclosure inhibits AP-mediated C3b deposition on a cell or tissue with an $IC_{50}$ of from $10^{-7}$ M to $10^{-9}$ M, e.g., an $IC_{50}$ of from $10^{-7}$ M to $5 \times 10^7$ M, from $5 \times 10^{-7}$ M to $10^{-8}$ M, from $10^{-8}$ M to $5 \times 10^{-9}$ M, or from $5 \times 10^8$ M to $10^9$ M.

In some cases, an anti-Bb antibody of the present disclosure inhibits AP-mediated C3b deposition on red blood cells (RBCs) by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C3b deposition on RBCs in the absence of the anti-Bb antibody. In some cases, an anti-Bb antibody of the present disclosure inhibits AP-mediated C3b deposition on RBCs with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^{-8}$ M to $5 \times 10^{-8}$ M, or from $5 \times 10^8$ M to $10^9$ M.

In some cases, an anti-Bb antibody of the present disclosure, when administered in one or more doses to an individual in need thereof, reduces the amount of factor Bb in circulation in the individual. For example, in some cases, an anti-Bb antibody of the present disclosure, when administered in one or more doses to an individual in need thereof, reduces the amount of factor Bb in circulation in the individual by at least 10%, at least 20%, at least 30%, at least 40%, at least 50%, at least 60%, at least 65%, at least 70%, at least 75%, at least 80%, at least 85%, at least 90%, or at least 95%, compared to the amount of factor Bb in circulation in the individual in the absence of administering the anti-Bb antibody, or compared to the amount of factor Bb in circulation in the individual before administration of the anti-Bb antibody.

In some cases, an anti-Bb antibody of the present disclosure inhibits factor H (fH) interaction with C3bBb (complement alternative pathway C3 convertase). In some cases, an anti-Bb antibody of the present disclosure inhibits fH interaction with C3bBb by at least 10%, at least 20%, at least 30%, at least 40%, at least 50%, at least 60%, at least 65%, at least 70%, at least 75%, at least 80%, at least 85%, at least 90%, or at least 95%, compared to the interaction of fH to C3bBb in the absence of the anti-Bb antibody. In some cases, an anti-Bb antibody of the present disclosure that inhibits fH interaction with C3bBb comprises VH and VL CDRs present in M4 VH and VL, respectively.

In some cases, an anti-Bb antibody of the present disclosure inhibits factor H (fH) binding to C3bBb (complement alternative pathway C3 convertase). In some cases, an anti-Bb antibody of the present disclosure inhibits fH binding to C3bBb by at least 10%, at least 20%, at least 30%, at least 40%, at least 50%, at least 60%, at least 65%, at least 70%, at least 75%, at least 80%, at least 85%, at least 90%, or at least 95%, compared to the binding of fH to C3bBb in the absence of the anti-Bb antibody. In some cases, an anti-Bb antibody of the present disclosure that inhibits fH binding to C3bBb comprises VH and VL CDRs present in M4 VH and VL, respectively.

In some cases, an anti-Bb antibody of the present disclosure that inhibits fH interaction with C3bBb induces degradation of C3. In some cases, an anti-Bb antibody of the present disclosure that inhibits fH interaction with C3bBb, when such antibody is administered in one or more doses to an individual in need thereof, reduces the amount of C3 in a body fluid or tissue of the individual by at least 10%, at least 20%, at least 30%, at least 40%, at least 50%, at least 60%, at least 65%, at least 70%, at least 75%, at least 80%, at least 85%, at least 90%, or at least 95%, compared to the amount of C3 in the body fluid or tissue in the absence of administering the anti-Bb antibody, or compared to the amount of factor Bb in circulation in the individual before administration of the anti-Bb antibody. Body fluids include, e.g., serum, plasma, lymph, extracellular fluids, blood, and the like.

In some cases, an anti-Bb antibody of the present disclosure that inhibits fH binding to C3bBb induces degradation of C3. In some cases, an anti-Bb antibody of the present disclosure that inhibits fH binding to C3bBb, when such antibody is administered in one or more doses to an individual in need thereof, reduces the amount of C3 in a body fluid or tissue of the individual by at least 10%, at least 20%, at least 30%, at least 40%, at least 50%, at least 60%, at least 65%, at least 70%, at least 75%, at least 80%, at least 85%, at least 90%, or at least 95%, compared to the amount of C3 in the body fluid or tissue in the absence of administering the anti-Bb antibody, or compared to the amount of factor Bb in circulation in the individual before administration of the anti-Bb antibody. Body fluids include, e.g., serum, plasma, lymph, extracellular fluids, blood, and the like.

In some cases, an anti-Bb antibody of the present disclosure that inhibits fH interaction with C3bBb, when such antibody is administered in one or more doses to an individual who has catastrophic anti-phospholipid syndrome, reduces the amount of C3 in a body fluid or tissue of the individual by at least 10%, at least 20%, at least 30%, at least 40%, at least 50%, at least 60%, at least 65%, at least 70%, at least 75%, at least 80%, at least 85%, at least 90%, or at least 95%, compared to the amount of C3 in the body fluid or tissue in the absence of administering the anti-Bb antibody, or compared to the amount of factor Bb in circulation in the individual before administration of the anti-Bb antibody.

In some cases, an anti-Bb antibody of the present disclosure that inhibits fH binding to C3bBb, when such antibody is administered in one or more doses to an individual who has catastrophic anti-phospholipid syndrome, reduces the amount of C3 in a body fluid or tissue of the individual by at least 10%, at least 20%, at least 30%, at least 40%, at least 50%, at least 60%, at least 65%, at least 70%, at least 75%, at least 80%, at least 85%, at least 90%, or at least 95%, compared to the amount of C3 in the body fluid or tissue in the absence of administering the anti-Bb antibody, or compared to the amount of factor Bb in circulation in the individual before administration of the anti-Bb antibody.

The present disclosure provides for any anti-Bb antibody of the embodiments to be humanized. In some cases, an anti-Bb antibody of the present disclosure comprises a humanized framework region. In some cases, an anti-Bb antibody of the present disclosure comprises a humanized light chain framework region. In some cases, an anti-Bb antibody of the present disclosure comprises a humanized heavy chain framework region. In some cases, an anti-Bb antibody of the present disclosure comprises a humanized light chain framework region and a humanized heavy chain framework region.

In some cases, a subject anti-Bb antibody comprises one or more humanized framework regions (FRs). In some cases, a subject anti-Bb antibody comprises a light chain variable region comprising one, two, three, or four light chain FRs that have been humanized. In some embodiments, a subject anti-Bb antibody comprises a light chain variable region comprising, in order from N-terminus to C-terminus: a humanized light chain FR1; a CDR-L1 as set forth herein; a humanized light chain FR2; a CDR-L2 as set forth herein; a humanized light chain FR3; a CDR-L3 as set forth herein; and a humanized light chain FR4. In some cases, the respective amino acid sequences of CDR-L1, CDR-L2, and CDR-L3 are one of the following combinations: SEQ ID NO:1, SEQ ID NO:2, and SEQ ID NO:3; SEQ ID NO:9, SEQ ID NO:10, and SEQ ID NO:11; SEQ ID NO:17, SEQ ID NO:18, and SEQ ID NO:19; and SEQ ID NO:25, SEQ ID NO:2, and SEQ ID NO:26.

For example, an anti-Bb antibody of the present disclosure can comprise a light chain variable region that comprises, in order from N-terminus to C-terminus: a humanized light chain FR1; a CDR-L1 comprising amino acid sequence SEQ ID NO:1; a humanized light chain FR2; a CDR-L2 comprising amino acid sequence SEQ ID NO:2; a humanized light chain FR3; a CDR-L3 comprising amino acid sequence SEQ ID NO:3; and a humanized light chain FR4.

In some cases, an anti-Bb antibody of the present disclosure comprises a heavy chain variable region comprising one, two, three, or four heavy chain FRs that have been humanized. In some cases, a subject antibody comprises a heavy chain variable region comprising, in order from N-terminus to C-terminus: a humanized heavy chain FR1; a CDR-H1 as set forth herein; a humanized heavy chain FR2; a CDR-H2 as set forth herein; a humanized heavy chain FR3; a CDR-H3 as set forth herein; and a humanized heavy chain FR4. For example, a subject antibody can comprise a heavy chain variable region that comprises, in order from N-terminus to C-terminus: a humanized heavy chain FR1; a CDR-H1 comprising amino acid sequence SEQ ID NO:4; a humanized heavy chain FR2; a CDR-H2 comprising amino acid sequence SEQ ID NO:5; a humanized heavy chain FR3; a CDR-H3 comprising amino acid sequence SEQ ID NO:6; and a humanized heavy chain FR4. In some embodiments, the respective amino acid sequences of CDR-H1, CDR-H2, and CDR-H3 are one of the following combinations: SEQ ID NO:4, SEQ ID NO:5, and SEQ ID NO:6; SEQ ID NO:12, SEQ ID NO:13, and SEQ ID NO:14; SEQ ID NO:20, SEQ ID NO:21, and SEQ ID NO:22; and SEQ ID NO:27, SEQ ID NO:28, and SEQ ID NO:29.

For example, an anti-Bb antibody of the present disclosure can comprise a heavy chain variable region that comprises, in order from N-terminus to C-terminus: a humanized heavy chain FR1; a CDR-L1 comprising amino acid sequence SEQ ID NO:4; a humanized heavy chain FR2; a CDR-L2 comprising amino acid sequence SEQ ID NO:5; a humanized heavy chain FR3; a CDR-L3 comprising amino acid sequence SEQ ID NO:6; and a humanized heavy chain FR4.

In some embodiments, an anti-Bb antibody of the present disclosure that binds human complement Bb protein also binds a complement Bb protein of another species. In some embodiments, an anti-Bb antibody of the present disclosure that binds human complement Bb protein also binds a non-human primate complement Bb protein. In some embodiments, an anti-Bb antibody of the present disclosure that binds human complement Bb protein also binds a rodent complement Bb protein. Examples of rodent complement Bb proteins include, but are not limited to, guinea pig Bb proteins, hamster Bb proteins, mouse Bb proteins, and rat Bb proteins. In some embodiments, such a cross-reactive antibody binds the complement Bb protein of another species with a $K_D$ of a similar order of magnitude as the antibody binds a human complement Bb protein.

In some cases, an anti-Bb antibody of the present disclosure is an Ig monomer or an antigen-binding fragment thereof that binds a complement Bb protein. In some cases, an anti-Bb antibody of the present disclosure is an Ig monomer. In some cases, an anti-Bb antibody of the present disclosure is an antigen-binding fragment of an Ig monomer that binds a complement Bb protein.

In some cases, an anti-Bb antibody of the present disclosure is selected from the group consisting of an Ig monomer, a Fab fragment, a F(ab')$_2$ fragment, a Fd fragment, a scFv, a scAb, a dAb, a Fv, a single domain heavy chain antibody, and a single domain light chain antibody. In some cases, an anti-Bb antibody of the present disclosure is a single-chain Fv (scFv) antibody.

In some cases, an anti-Bb antibody of the present disclosure comprises a light chain region and a heavy chain region that are present in separate polypeptides.

In some cases, an anti-Bb antibody of the present disclosure comprises a light chain region and a heavy chain region that are present in a single polypeptide.

In some embodiments, an anti-Bb antibody of the present disclosure comprises anti-Bb heavy chain CDRs and anti-Bb light chain CDRs in a single polypeptide chain, e.g., in some embodiments, a subject antibody is a scFv. In some embodiments, an anti-Bb antibody of the present disclosure comprises, in order from N-terminus to C-terminus: a first amino acid sequence of from about 5 amino acids to about 25 amino acids in length; a CDR-L1; a second amino acid sequence of from about 5 amino acids to about 25 amino acids in length; a CDR-L2; a third amino acid sequence of from about 5 amino acids to about 25 amino acids in length; a CDR-L3; a fourth amino acid sequence of from about 5 amino acids to about 25 amino acids in length; a CDR-H1; a fifth amino acid sequence of from about 5 amino acids to about 25 amino acids in length; a CDR-H2; a sixth amino acid sequence of from about 5 amino acids to about 25 amino acids in length; a CDR-H3; and a seventh amino acid sequence of from about 5 amino acids to about 25 amino acids in length. In some cases, the respective amino acid sequences of CDR-L1, CDR-L2, CDR-L3, CDR-H1, CDR-H2, and CDR-H3 are one of the following combinations: SEQ ID NO:1, SEQ ID NO:2, SEQ ID NO:3, SEQ ID NO:4, SEQ ID NO:5, and SEQ ID NO:6; SEQ ID NO:9, SEQ ID NO:10, SEQ ID NO:11, SEQ ID NO:12, SEQ ID NO:13, and SEQ ID NO:14; SEQ ID NO:17, SEQ ID NO:18, SEQ ID NO:19, SEQ ID NO:20, SEQ ID NO:21, and SEQ ID NO:22; and SEQ ID NO:25, SEQ ID NO:2, SEQ ID NO:26, SEQ ID NO:27, SEQ ID NO:28, and SEQ ID NO:29. For example, in some cases, an anti-Bb antibody of the present disclosure comprises, in order from N-terminus to C-terminus: a first amino acid sequence of from about 5 amino acids to about 25 amino acids in length; a CDR-L1 comprising the amino acid sequence set forth in SEQ ID NO:1; a second amino acid sequence of from about 5 amino acids to about 25 amino acids in length; a CDR-L2 comprising the amino acid sequence set forth in SEQ ID NO:2; a third amino acid sequence of from about 5 amino acids to about 25 amino acids in length; a CDR-L3 comprising the amino acid sequence set forth in SEQ ID NO:3; a fourth amino acid sequence of from about 5 amino acids to about 25 amino acids in length; a CDR-H1 comprising the amino acid sequence set forth in SEQ ID NO:4; a fifth amino acid sequence of from about 5 amino acids to about 25 amino acids in length; a CDR-H2 comprising the amino acid sequence set forth in SEQ ID NO:5; a sixth amino acid sequence of from about 5 amino acids to about 25 amino acids in length; a CDR-H3 comprising the amino acid sequence set forth in SEQ ID NO:6; and a seventh amino acid sequence of from about 5 amino acids to about 25 amino acids in length.

In some embodiments, an anti-Bb antibody of the present disclosure comprises, in order from N-terminus to C-terminus: a light chain FR1 region; a CDR-L1; a light chain FR2 region; a CDR-L2; a light chain FR3 region; a CDR-L3; optionally a light chain FR4 region; a linker region; optionally a heavy chain FR1 region; a CDR-H1; a heavy chain FR2 region; a CDR-H2; a heavy chain FR3 region; a CDR-H3; and a heavy chain FR4 region. In some embodiments, the respective amino acid sequences of CDR-L1, CDR-L2, CDR-L3, CDR-H1, CDR-H2, and CDR-H3 are one of the following combinations: SEQ ID NO:1, SEQ ID NO:2, SEQ ID NO:3, SEQ ID NO:4, SEQ ID NO:5, and SEQ ID NO:6; SEQ ID NO:9, SEQ ID NO:10, SEQ ID NO:11, SEQ ID NO:12, SEQ ID NO:13, and SEQ ID NO:14; SEQ ID NO:17, SEQ ID NO:18, SEQ ID NO:19, SEQ ID NO:20, SEQ ID NO:21, and SEQ ID NO:22; and SEQ ID NO:25, SEQ ID NO:2, SEQ ID NO:26, SEQ ID NO:27, SEQ ID NO:28, and SEQ ID NO:29. In some of these embodiments, one or more of the FR regions is a humanized FR region. In some of these embodiments, each of the FR regions is a humanized FR region. The linker region can be from about 5 amino acids (aa) to about 50 amino acids in length, e.g., from about 5 aa to about 10 aa, from about 10 aa to about 15 aa, from about 15 an to about 20 aa, from about 20 aa to about 25 aa, from about 25 an to about 30 aa, from about 30 an to about 35 aa, from about 35 aa to about 40 aa, from about 40 an to about 45 aa, or from about 45 aa to about 50 aa in length.

In some cases, an anti-Bb antibody of the present disclosure comprises, in order from N-terminus to C-terminus: a heavy chain FR1 region; a CDR-H1; a heavy chain FR2 region; a CDR-H2; a heavy chain FR3 region; a CDR-H3; optionally a heavy chain FR4 region; a linker; optionally a light chain FR1 region; a CDR-L1; a light chain FR2 region; a CDR-L2; a light chain FR3 region; a CDR-L3; and a light chain FR4 region. In some embodiments, the respective amino acid sequences of CDR-L1, CDR-L2, CDR-L3, CDR-H1, CDR-H2, and CDR-H3 are one of the following combinations: SEQ ID NO:1, SEQ ID NO:2, SEQ ID NO:3, SEQ ID NO:4, SEQ ID NO:5, and SEQ ID NO:6; SEQ ID NO:9, SEQ ID NO:10, SEQ ID NO:11, SEQ ID NO:12, SEQ ID NO:13, and SEQ ID NO:14; SEQ ID NO:17, SEQ ID NO:18, SEQ ID NO:19, SEQ ID NO:20, SEQ ID NO:21, and SEQ ID NO:22; and SEQ ID NO:25, SEQ ID NO:2, SEQ ID NO:26, SEQ ID NO:27, SEQ ID NO:28, and SEQ ID NO:29. In some of these embodiments, one or more of the FR regions is a humanized FR region. In some of these embodiments, each of the FR regions is a humanized FR region. The linker region can be from about 5 amino acids to about 50 amino acids in length, e.g., from about 5 an to about 10 aa, from about 10 aa to about 15 aa, from about 15 an to about 20 aa, from about 20 an to about 25 aa from about 25 aa to about 30 an, from about 30 aa to about 35 aa, from about 35 an to about 40 aa, from about 40 aa to about 45 aa, or from about 45 an to about 50 aa in length.

Linkers suitable for use a subject antibody include "flexible linkers". If present, the linker molecules are generally of sufficient length to permit some flexible movement between linked regions. In some embodiments, the linker molecules are generally about 6-50 atoms long. The linker molecules can also be, for example, aryl acetylene, ethylene glycol oligomers containing 2-10 monomer units, diamines, diacids, amino acids, or combinations thereof. Other linker molecules that can bind polypeptides can be used in light of this disclosure.

Suitable linkers can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO:75) and $(GGGS)_n$ (SEQ ID NO:76), where n is an integer of at least one), glycine-alanine polymers, alanine-serine polymers, and other flexible linkers known in the art. Glycine and glycine-serine polymers are of interest since both of these amino acids are relatively unstructured, and therefor can serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGSG (SEQ ID NO:77). GGSGG (SEQ ID NO:78), GSGSG (SEQ ID NO:79), GSGGG (SEQ ID NO:80), GGGSG (SEQ ID NO:81). GSSSG (SEQ ID NO:82), and the like. The ordinarily skilled artisan will recognize that design of a peptide conjugated to any elements described above can include linkers that are all or partially flexible, such that the linker can include a flexible linker as well as one or more portions that confer less flexible structure.

In some embodiments, an anti-Bb antibody of the present disclosure comprises scFv multimers. For example, in some embodiments, an anti-Bb antibody of the present disclosure is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids (aa) in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFv multimer is humanized, as described above.

In some cases, an anti-Bb antibody of the present disclosure comprises a constant region of an immunoglobulin (e.g., an Fc region). The Fc region, if present, can be a human Fc region or an Fc region from any animal that has a complement system. In some embodiments, the Fc region, if present, is a human Fc region. In some cases, the Fc region comprises one or more mutations (e.g., amino acid substitutions) that increase the affinity of the Fc to neonatal Fc receptor (FcRn); see, e.g., Monnet et al. (2015) *Front. Immunol.* 6:39. Examples of amino acid substitutions that increase affinity of an Fc polypeptide for FcRn include, e.g., a combination of M428L and N434S; a combination of M252Y. S254T, and T256E. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Another example of a suitable heavy chain Fc region is a human isotype IgG2a Fc. Yet another example of a suitable heavy chain Fc region is a human isotype IgG2b Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')$_2$, and Fv, or as single chain antibodies in which heavy and light chain variable domains are linked through a spacer.

In some cases, the heavy chain region is of the isotype IgG4. In some of these embodiments, the hinge region comprises an S241P substitution. See, e.g., Angal et al. (1993) *Mol. Immunol.* 30:105. In some of these embodiments, the hinge region comprises an L236E substitution. See, e.g., Reddy et al. (2000) *J. Immunol.* 164:1925; and Klechevsky et al. (2010) *Blood* 116:1685. In some of these embodiments, the hinge region comprises an S241P substitution and an L236E substitution.

A subject antibody can comprise a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazid group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to the antibody, where the antibody comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some cases, the azide or alkyne group is linked to the PEG molecule through an amide linkage. A "non-naturally encoded amino acid" refers to an amino acid that is not one of the 20 common amino acids or pyrolysine or selenocysteine. Other terms that can be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly (ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50,000 Da, e.g., from 5,000 Da to 40,000 Da, or from 25.000 to 40,000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a non-peptide synthetic polymer. In some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and can be found in, e.g., U.S. Pat. No. 5,849,860. PEG suitable for conjugation to a protein is generally soluble in water at room temperature, and has the general formula R(O—CH$_2$—CH$_2$)$_n$O—R, where R is hydrogen or a protective group such as an alkyl or an alkanol group, and where n is an integer from 1 to 1,000. Where R is a protective group, it generally has from 1 to 8 carbons.

In some embodiments, the PEG conjugated to the subject antibody is linear. In some embodiments, the PEG conjugated to the subject antibody is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., a subject antibody can comprise a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the aspargine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine can also be used.

Addition of glycosylation sites to an antibody is conveniently accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers include bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123131}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-diphenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawbery, mCherry, mGrape1, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) Nature Biotechnol. 17:969-973, is suitable for use.

In some embodiments, a subject antibody is conjugated to a therapeutic agent. Any of the subject antibodies disclosed herein can be used to forma an antibody-agent conjugate. The agent can be attached to the N terminus of the light chain, the C terminus of the light chain, the N terminus of the heavy chain, or the C terminus of the heavy chain. In some embodiments, the agent is attached to the hinge of the antibody or to one or more other sites on the antibody. For a single chain antibody, the agent can be attached to the N or C terminus of the single chain antibody. The agent can be conjugated to the antibody directly or via a linker using techniques known to those skilled in the art. The linker can be cleavable or non-cleavable. Examples of such therapeutic agents (e.g., for use in therapy) are known to those skilled in the art.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., YPYDVPDYA; SEQ ID NO:83), FLAG (e.g., DYKDDDDK; SEQ ID NO:84), c-myc (e.g., EQKLISEEDL; SEQ ID NO:85), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion can also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:86), HisX6 (HHHHHH) (SEQ ID NO:87), C-myc (EQKLISEEDL) (SEQ ID NO:88), Flag (DYKDDDDK) (SEQ ID NO:85), StrepTag (WSHPQFEK) (SEQ ID NO:89), hemagglutinin, e.g., HA Tag (YPYDVPDYA; SEQ ID NO:90), glutathinone-S-transferase (GST), thioredoxin, cellulose binding domain, RYIRS (SEQ ID NO:91), Phe-His-His-Thr (SEQ ID NO:92), chitin binding domain, S-peptide, T7 peptide, SH2 domain, C-end RNA tag, WEAAAREACCRECCARA (SEQ ID NO:93), metal binding domains, e.g., zinc binding domains or calcium binding domains such as those from calcium-binding proteins, e.g., calmodulin, troponin C, calcineurin B, myosin light chain, recoverin, S-modulin, visinin, VILP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

In some embodiments, an anti-Bb antibody of the present disclosure is formulated with an agent that facilitates crossing the blood-brain barrier (BBB). In some embodiments, the antibody is fused, directly or through a linker, to a compound that promotes the crossing of the BBB. Examples of such a compound include, but are not limited to, a carrier molecule, a peptide, or a protein. An anti-Bb antibody of the present disclosure will in some embodiments be fused to a polypeptide that binds an endogenous BBB receptor. Linking an anti-Bb antibody of the present disclosure to a polypeptide that binds an endogenous BBB receptor facilitates crossing the BBB, e.g., in a subject treatment method (see below) involving administration of an anti-Bb antibody of the present disclosure to an individual in need thereof. Suitable polypeptides that bind an endogenous BBB receptor include antibodies, e.g., monoclonal antibodies, or antigen-binding fragments thereof, that specifically bind an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

As an example, a subject anti-Bb antibody can be a bi-specific antibody comprising a first antigen-binding portion that specifically binds an epitope in a complement Bb protein; and a second antigen-binding portion that binds an endogenous BBB receptor. For example, in some instances, a subject anti-Bb antibody is a bi-specific antibody comprising a first antigen-binding portion that specifically binds an epitope in a Bb protein; and a second antigen-binding portion that binds a transferrin receptor.

For example, an anti-Bb antibody of the present disclosure can be fused to a peptide that facilitates crossing the BBB, the peptide having a length of from about 15 amino acids to about 25 amino acids, and comprising an amino acid sequence that is at least about 85% amino acid sequence identical to one of the following peptides: Angiopep-1 (TFFYGGCRGKRNNFKTEEY) (SEQ ID NO:93); Angiopep-2 (TFFYGGSRGKRNNFKTEEY) (SEQ ID NO:94); cys-Angiopep-2 (CTFFYGGSRGKRNNFKTEEY) (SEQ ID NO:95); Angiopep-2-cys (TFFYGGSRGKRNNFK-TEEYC) (SEQ ID NO:96); and an aprotinin fragment (TFVYGGCRAKRNNFKS) (SEQ ID NO:97). See, e.g., U.S. Patent Publication Nos. 2011/0288011; and 2009/0016959. A peptide that facilitates crossing the BBB can be fused to the N-terminus of an anti-Bb light chain region, to the C-terminus of an anti-Bb light chain region, to the N-terminus of an anti-Bb heavy chain region, to the C-terminus of an anti-Bb heavy chain region, to the N-terminus of a subject anti-Bb single-chain antibody, to the C-terminus of a subject anti-Bb single-chain antibody, etc.

In some embodiments, a subject antibody comprises a polyamine modification. Polyamine modification of a subject antibody enhances permeability of the modified antibody at the BBB. A subject antibody can be modified with polyamines that are either naturally occurring or synthetic. Sec, for example, U.S. Pat. No. 5,670,477. Useful naturally occurring polyamines include putrescine, spermidine, spermine, 1,3-diaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or $N(R)_2$ moieties, wherein R is H, ($C_1$-$C_4$) alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated (e.g., encapsulated) into a liposome.

Methods of Producing a Subject Antibody

A subject antibody (an anti-Bb antibody of the present disclosure) can be produced by any known method, e.g., conventional synthetic methods for protein synthesis; recombinant DNA methods; etc. In some embodiments, the subject antibody is produced by a method selected from the group consisting of recombinant production and chemical synthesis.

Where a subject antibody is a single chain polypeptide, it can be synthesized using standard chemical peptide synthesis techniques. Where a polypeptide is chemically synthesized, the synthesis can proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid can be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, repressor elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce an anti-Bb antibody of the present disclosure (e.g., polynucleotides encoding a subject anti-Bb antibody). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising an anti-Bb antibody of the present disclosure. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acid Molecules, Expression Vectors, and Host Cells

The present disclosure provides nucleic acid molecules comprising nucleotide sequences encoding an anti-Bb antibody of the present disclosure.

In some embodiments, a nucleic acid of the present disclosure comprises a nucleotide sequence that encodes a subject anti-Bb antibody comprising a light chain variable region that is at least 85%, 86%, 87%, 88%, 89%, 90%, 91%, 92%, 93%, 94%, 95%, 96%, 97%, 98% or 99% amino acid sequence identical to an amino acid sequence selected from the group consisting of SEQ ID NO:7. SEQ ID NO:15, SEQ ID NO:23, and SEQ ID NO:30. In some embodiments, a nucleic acid of the present disclosure comprises a nucleotide sequence that encodes a subject anti-Bb antibody comprising a light chain variable region comprising an amino acid sequence selected from the group consisting of SEQ ID NO:7, SEQ ID NO:15, SEQ ID NO:23, and SEQ ID NO:30.

In some embodiments, a nucleic acid of the present disclosure comprises a nucleotide sequence that encodes a subject anti-Bb antibody comprising a heavy chain variable region that is at least 85%, 86%, 87%, 88%, 89%, 90%, 91%, 92%, 93%, 94%, 95%, 96%, 97%, 98% or 99% amino acid sequence identical to an amino acid sequence selected from the group consisting of SEQ ID NO:8, SEQ ID NO:16, SEQ ID NO:24, and SEQ ID NO:31. In some embodiments, a nucleic acid of the present disclosure comprises a nucleotide sequence that encodes a subject anti-Bb antibody comprising a heavy chain variable region comprising an amino acid sequence selected from the group consisting of SEQ ID NO:8. SEQ ID NO:16, SEQ ID NO:24, and SEQ ID NO:31.

In some embodiments, a nucleic acid of the present disclosure comprises a nucleotide sequence that encodes a subject anti-Bb antibody comprising a light chain variable region comprising a CDR-L1, a CDR-L2, and a CDR-L3 in one of the following combinations: SEQ ID NO:1, SEQ ID NO:2, and SEQ ID NO:3; SEQ ID NO:9, SEQ ID NO:10, and SEQ ID NO:11; SEQ ID NO:17, SEQ ID NO:18, and SEQ ID NO:19; and SEQ ID NO:25, SEQ ID NO:2, and SEQ ID NO:26.

In some embodiments, a nucleic acid of the present disclosure comprises a nucleotide sequence that encodes a subject anti-Bb antibody comprising a heavy chain variable region comprising a CDR-H1, a CDR-H2, and a CDR-H3 in one of the following combinations: SEQ ID NO:4, SEQ ID NO:5, and SEQ ID NO:6; SEQ ID NO:12, SEQ ID NO:13, and SEQ ID NO:14; SEQ ID NO:20, SEQ ID NO:21, and SEQ ID NO:22; SEQ ID NO:27, SEQ ID NO:28, and SEQ ID NO:29.

In some embodiments, a nucleic acid of the present disclosure comprises a nucleotide sequence that encodes a subject anti-Bb antibody comprising a light chain variable region and a heavy chain variable region.

A nucleic acid comprising a nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. Suitable promoters for use in prokaryotic host cells include, but are not limited to, a bacteriophage T7 RNA polymerase promoter; a T3 promoter; a T5 promoter; a lambda P promoter; a trp promoter; a lac operon promoter; a hybrid promoter, e.g., a lac/tac hybrid promoter, a tac/t hybrid promoter, a trp/lac promoter, a T7/lac promoter; a trc promoter; a tac promoter, and the like; a gpt promoter; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96117951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the Lac repressor protein from binding the operator), a tryptophan promoter operator (when complexed with tryptophan, TrpR repressor protein has a conformation that binds the operator; in the absence of tryptophan, the TrpR repressor protein has a conformation that does not bind the operator), and a tac promoter operator (see, for example, deBoer et al. (1983) Proc. Nat. Acad. Sci. U.S.A. 80:21-25).

In some embodiments, e.g., for expression in a yeast cell, a suitable promoter is a constitutive promoter such as an ADH1 promoter, a PGK 1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*).

For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-1 promoter; and various art-known tissue specific promoters.

Selection of the appropriate vector and promoter is well within the level of ordinary skill in the art.

A nucleic acid comprising a nucleotide sequence encoding a subject antibody can be present in an expression vector and/or a cloning vector. The present disclosure provides a recombinant vector, which comprises a nucleic acid comprising a nucleotide sequence encoding a subject antibody in a cloning vector. The present disclosure also provides a recombinant molecule, which comprises a nucleic acid comprising a nucleotide sequence encoding a subject antibody operatively linked to appropriate regulatory sequence(s) in an expression vector to ensure expression of the encoded antibody. Where a subject antibody comprises two separate polypeptides, a nucleic acid comprising a nucleotide sequence(s) encoding the two polypeptides can be cloned in the same or separate vectors to form one or more recombinant vectors. A recombinant vector can include a selectable marker, an origin of replication, and other features that provide for replication and/or maintenance of the recombinant vector.

Large numbers of suitable vectors and promoters are known to those of skill in the art; many are commercially available for generating a subject recombinant molecule. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRITS (Pharmacia. Uppsala. Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host can be present. Suitable expression vectors include, but are not limited to, viral vectors. Examples of viral vectors include, but are not limited to, viral vectors based on: vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81

86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus (see. e.g., Miyoshi et al., PNAS 94:10319 23, 1997; Takahashi et al., J Virol 73:7812 7816, 1999), myeloproliferative sarcoma virus, and mammary tumor virus); and the like.

As noted above, a subject nucleic acid comprises a nucleotide sequence encoding an anti-Bb antibody of the present disclosure. In some embodiments, a subject nucleic acid comprises a nucleotide sequence encoding heavy- and light-chain CDRs of a subject antibody, where the CDR-encoding sequences are interspersed with FR-encoding nucleotide sequences. In some embodiments, the FR-encoding nucleotide sequences are human FR-encoding nucleotide sequences.

Host Cells

The present disclosure provides isolated genetically modified host cells (e.g., in vitro cells) that are genetically modified with a subject nucleic acid. The present disclosure provides isolated genetically modified host cells (e.g., in vitro cells) that are genetically modified with a subject recombinant expression vector(s) (comprising a nucleic acid comprising a nucleotide sequence(s) encoding an anti-Bb antibody of the present disclosure). In some embodiments, a subject isolated genetically modified host cell can produce a subject antibody. Such a cell is referred to as a recombinant cell or a genetically modified cell or a genetically modified host cell. A recombinant cell comprises a recombinant nucleic acid(s) (e.g., a recombinant expression vector) comprising a nucleotide sequence(s) encoding a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), Chinese hamster ovary (CHO) cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. In some cases, the cells are HEK cells. In some cases, the cells are CHO cells, e.g., CHO-K1 cells (ATCC No. CCL-61). CHO-M cells, CHO-DG44 cells (ATCC No. PTA-3356), and the like. In some embodiments, the host cell is a COS cell. In some embodiments, the host cell is a 293 cell. In some embodiments, the host cell is a CHO cell.

Suitable yeast cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichodema reesei*, *Chrysosporium lucknowense*, *Fusarium* sp., *Fusarium gramineum*, *Fusarium venenatum*, *Neurospora crassa*, *Chlamydomonas reinhardtii*, and the like. In some embodiments, the host cell is a *Saccharomyces*. In some embodiments, the host cell is a *Pichia*.

Suitable prokaryotic cells include, but are not limited to, any of a variety of laboratory strains of *Escherichia coli*, *Bacillus* (e.g., *B. subtilis*). *Lactobacillus* sp., and the like. See, e.g., Carrier et al. (1992) *J. Immunol.* 148:1176-1181; U.S. Pat. No. 6,447,784; and Sizemore et al. (1995) Science 270:299-302. Typically, the laboratory strain is one that is non-pathogenic. In some embodiments, the host cell is *Escherichia coli*. In some embodiments, the host cell is *Bacillus subtilis*.

Pharmaceutical Compositions

The present disclosure provides compositions, including pharmaceutical compositions comprising an anti-Bb antibody of the present disclosure. In general, a pharmaceutical composition, also referred to herein as a formulation, comprises an effective amount of a subject antibody. An "effective amount" means a dosage sufficient to produce a desired result, e.g., reduction in an adverse symptom associated with a complement-mediated disease or disorder, amelioration of a symptom of a complement-mediated disease or disorder, slowing progression of a complement-mediated disease or disorder, etc. Generally, the desired result is at least a reduction in a symptom of a complement-mediated disease or disorder, as compared to a control. In some embodiments, a subject antibody is formulated and/or modified to enable the antibody to cross the blood-brain barrier. In some embodiments, a subject antibody is delivered in such a manner as to avoid the blood-brain barrier. In some embodiments, an anti-Bb antibody of the present disclosure is formulated with an agent that facilitates crossing the blood-brain barrier. In some embodiments, the subject antibody is fused, directly or through a linker, to a compound that promotes the crossing of the blood-brain barrier.

In a method of the present disclosure, an anti-Bb antibody of the present disclosure can be administered to the host using any convenient means capable of resulting in the desired therapeutic effect or diagnostic effect. Thus, the anti-Bb antibody can be incorporated into a variety of formulations for therapeutic administration. More particularly, a subject antibody can be formulated into pharmaceutical compositions by combination with appropriate, pharmaceutically acceptable carriers, pharmaceutically acceptable diluents, or other pharmaceutically acceptable excipients and can be formulated into preparations in solid, semi-solid, liquid or gaseous forms, such as tablets, capsules, powders, granules, ointments, solutions, suppositories, injections, inhalants and aerosols. In some embodiments, a pharmaceutical composition comprises a subject antibody and a pharmaceutically acceptable excipient.

In pharmaceutical dosage forms, a subject antibody can be administered in the form of their pharmaceutically acceptable salts, or they can also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with hinders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying the antibody in an aqueous or nonaqueous solvent, such as vegetable or other similar oils, propylene glycol, synthetic aliphatic acid glycerides, injectable organic esters (e.g., ethyl oleate), esters of higher aliphatic acids or propylene glycol; and if desired, with conventional additives such as solubilizers, isotonic agents, suspending agents, emulsifying agents, stabilizers and preservatives. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Furthermore, the pharmaceutical composition of the present disclosure can comprise further agents such as dopamine or psychopharmacologic drugs, depending on the intended use of the pharmaceutical composition.

Pharmaceutical compositions comprising a subject antibody are prepared by mixing a subject antibody having the desired degree of purity with optional physiologically acceptable carriers, other excipients, stabilizers, surfactants, buffers and/or tonicity agents. Acceptable carriers, other excipients and/or stabilizers are nontoxic to recipients at the dosages and concentrations employed, and include buffers such as phosphate, citrate, and other organic acids; antioxidants including ascorbic acid, glutathione, cysteine, methionine and citric acid, preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition can be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents can be used for the production of pharmaceutical compositions for parenteral administration; see also Chen (1992) Drug Dev Ind Pharm 18, 1311-54.

Exemplary antibody concentrations in a subject pharmaceutical composition can range from about 1 mg/mL to about 200 mg/mL or from about 50 mg/mL to about 200 mg/mL, or from about 150 mg/mL to about 200 mg/mL.

An aqueous formulation of the antibody can be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent can be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions can be suitable. The term "isotonic" denotes a solution having the same tonicity as some other solution with which it is compared, such as a physiological salt solution or serum. Tonicity agents can be used in an amount of about 5 mM to about 350 mM, e.g., in an amount of 100 mM to 350 nM.

A surfactant can also be added to the antibody formulation to reduce aggregation of the formulated antibody and/or minimize the formation of particulates in the formulation and/or reduce adsorption. Exemplary surfactants include polyoxyethylenesorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant can range from about 0.001% to about 1% w/v.

A lyoprotectant can also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer;

optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM sucrose; and has a pH of 5.5; or 4) 75 mg/mL of a subject antibody; 0.04% Tween 20 w/v; 20 mM L-histidine; and 250 mM trehalose; and has a pH of 5.5; or 5) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.02% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like. Aerosol formulations such as nasal spray formulations include purified aqueous or other solutions of the active agent with preservative agents and isotonic agents. Such formulations are adjusted to a pH and isotonic state compatible with the nasal mucous membranes.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions can be provided wherein each dosage unit, for example, teaspoonful, tablespoonful, tablet or suppository, contains a predetermined amount of the composition. Similarly, unit dosage forms for injection or intravenous administration can comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an anti-Bb antibody of the present disclosure, calculated in an amount sufficient to produce the desired effect in association with a pharmaceutically acceptable diluent, carrier or vehicle. The specifications for a subject antibody can depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories can be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations can also contain preservatives such as, but not limited to, chlorobutanol and benzalkonium chloride. A surfactant can be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection can also be prepared. The preparation can also be emulsified or the antibody encapsulated in liposome vehicles.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some cases, a subject antibody is formulated in a controlled release formulation. Sustained-release preparations can be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations can be prevented by using appropriate additives, by controlling moisture content and by developing specific polymer matrix compositions.

Controlled release within the scope of the present disclosure can be taken to mean any one of a number of extended release dosage forms. The following terms can be considered to be substantially equivalent to controlled release, for the purposes of the present disclosure: continuous release, controlled release, delayed release, depot, extended release, gradual release, immediate release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, and sustained-action medications. Further discussions of these terms can be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release can be found in Agis F. Kydonieus, *Controlled Release Technologies: Methods. Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems can be found in Yie W. Chien, *Novel Drug Delivery Systems*, 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject anti-Bb antibody can be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. In some cases, an anti-Bb antibody of the present disclosure is administered in amounts of from 20 mg/kg body weight per dose to 100 mg/kg; for example, in some cases, an anti-Bb antibody of the present disclosure is administered in amounts of from 20 mg/kg to 25 mg/kg, from 25 mg/kg to 30 mg/kg, from 30 mg/kg to 35 mg/kg, from 35 mg/kg to 40 mg/kg, from 40 mg/kg to 45 mg/kg, from 45 mg/kg to 50 mg/kg, from 50 mg/kg to 55 mg/kg, from 55 mg/kg to 60 mg/kg, from 60 mg/kg to 65 mg/kg, from 65 mg/kg to 70 mg/kg, from 70 mg/kg to 75 mg/kg, from 75 mg/kg to 80 mg/kg, from 80 mg/kg to 85 mg/kg, from 85 mg/kg to 90 mg/kg, from 90 mg/kg to 95 mg/kg, or from 95 mg/kg to 100 mg/kg body weight per dose. In some cases, an anti-Bb antibody of the present disclosure is administered in an amount of from 20 mg/kg to 40 mg/kg body weight per dose. In some cases, an anti-Bb antibody of the present disclosure is administered in an amount of from 40 mg/kg to 60 mg/kg body weight per dose. If the regimen is a continuous infusion, it can also be in the range of 1 μg to 10 mg per kilogram of body weight per minute. In some cases, an anti-Bb antibody of the present disclosure is administered in amounts that are independent of weight. In some cases, an anti-Bb antibody of the present disclosure is administered in an amount of from 50 mg to 500 mg per dose, or per total daily dose; e.g., from 50 mg to 75 mg, from 75 mg to 100 mg, from 100 mg to 150 mg, from 150 mg to 200 mg, from 200 mg to 250 mg, from 250 mg to 300 mg, from 300 mg to 400 mg, or from 400 mg to 500 mg, per dose, or per total daily dose.

In some cases, a dose of an anti-Bb antibody of the present disclosure is in the range of 0.001 μg to 1000 μg; however, doses below or above this exemplary range are envisioned, especially considering the aforementioned factors. In some cases, the dosage can range, e.g., from about 0.0001 to 100 mg/kg, or from about 0.01 to 5 mg/kg (e.g., 0.02 mg/kg, 0.25 mg/kg, 0.5 mg/kg, 0.75 mg/kg, 1 mg/kg, 2 mg/kg, etc.) body weight. For example dosages can be 1 mg/kg body weight or 10 mg/kg body weight or within the range of 1-10 mg/kg, or at least 1 mg/kg. Doses intermediate in the above ranges are also intended to be within the scope of the invention.

Individuals can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment.

Those of skill will readily appreciate that dose levels and administration schedules can vary as a function of the specific antibody, the severity of the symptoms and the susceptibility of the subject to side effects. Preferred dosages and administration schedules for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intrathecal, intracranial, subcutaneous, intradermal, topical, intravenous, intraperitoneal, intraarterial (e.g., via the carotid artery), spinal or brain delivery, rectal, nasal, oral, and other enteral and parenteral routes of administration. Routes of administration can be combined, if desired, or adjusted depending upon the antibody and/or the desired effect. A subject antibody composition can be administered in a single dose or in multiple doses. In some cases, a subject antibody composition is administered orally. In some cases, a subject antibody composition is administered via an inhalational route. In some cases, a subject antibody composition is administered intranasally. In some cases, a subject antibody composition is administered locally. In some cases, a subject antibody composition is administered intracranially. In some cases, a subject antibody composition is administered intravenously. In some cases, a subject antibody composition is administered intrathecally. In some cases, a subject antibody composition is administered subcutaneously. In some cases, a subject antibody composition is administered intramuscularly.

An antibody of the present disclosure can be administered to a host using any available conventional methods and mutes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a complement-mediated disease or disorder. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some cases, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some cases, the host is an individual that has a complement system, such as a mammal, fish, or invertebrate. In some cases, the host is a complement system-containing mammal, fish, or invertebrate companion animal, agricultural animal, work animal, zoo animal, or lab animal. In some cases, the host is human.

The present disclosure provides a container suitable for containing a composition comprising a subject anti-Bb antibody for administration to an individual. For example, a subject antibody can be disposed within a container suitable for containing a pharmaceutical composition. The container can be, for example, a bottle (e.g., with a closure device, such as a cap), a blister pack (e.g., which can provide for enclosure of one or more doses per blister), a vial, flexible packaging (e.g., sealed Mylar or plastic bags), an ampule (for single doses in solution), a dropper, a syringe, thin film, a tube and the like. In some cases, a container, such as a sterile container, comprises a subject pharmaceutical composition. In some cases, the container is a bottle or a syringe. In some cases, the container is a bottle. In some cases, the container is a syringe.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Methods of Treating a Complement-Mediated Disease or Disorder

The present disclosure provides methods of treating a complement-mediated disease or disorder. The methods generally involve administering an effective amount of an anti-Bb antibody of the present disclosure to an individual in need thereof. In some cases, administration of a subject anti-Bb antibody modulates the activity of the AP in a cell, a tissue, or a fluid of an individual, and treats the complement-mediated disease or disorder.

In some cases, an effective amount of an anti-Bb antibody of the present disclosure is an amount that is effective to inhibit AP activity in a cell, tissue, or fluid of the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the level of AP activity in the cell, tissue, or fluid in the absence of administration of the anti-Bb antibody, or before administration of the anti-Bb antibody. In some cases, the anti-Bb antibody inhibits AP activity with an $IC_{50}$ of from $10^{-7}$ M to $10^{-9}$ M, e.g., an $IC_{50}$ of from $10^{-7}$ M to $5 \times 10^{-7}$ M, from $5 \times 10^{-7}$ M to $10^{-8}$ M, from $10^8$ M to $5 \times 10^{-8}$ M, or from $5 \times 10^{-8}$ M to $10^{-9}$ M.

In some cases, an effective amount of an anti-Bb antibody of the present disclosure is an amount that is effective to inhibit formation of MAC in a cell, tissue, or fluid of the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of MAC formed in the cell, tissue, or fluid in the absence of administration of the anti-Bb antibody, or before administration of the anti-Bb antibody.

In some cases, an effective amount of an anti-Bb antibody of the present disclosure is an amount that is effective to inhibit C3b/Bb-mediated cleavage of C3 in a cell, tissue, or fluid of the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the cleavage of C3 in the cell, tissue, or fluid in the absence of administration of the anti-Bb antibody, or before administration of the anti-Bb antibody. In some cases, an anti-Bb antibody of the present disclosure inhibits C3b/Bb-mediated cleavage of C3 with an $IC_{50}$ of from $10^{-7}$ M to $10^{-9}$ M, e.g., an $IC_{50}$ of from $10^{-7}$ M to $5\times10^{-7}$ M, from $5\times10^7$ M to $10^{-8}$ M, from $10^{-8}$ M to $5\times10^{-8}$ M, or from $5\times10^{-8}$ M to $10^{-9}$ M.

In some cases, an effective amount of an anti-Bb antibody of the present disclosure is an amount that is effective to inhibit C3b/Bb-mediated cleavage of C3, and thereby to reduce production of a C3 cleavage product. For example, in some cases, an effective amount of an anti-Bb antibody of the present disclosure is an amount that is effective to inhibit C3b/Bb-mediated cleavage of C3, thereby reducing production of a C3 cleavage product (e.g., C3a and/or C3b), in a cell, tissue, or fluid of the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the production of the C3 cleavage product in the cell, tissue, or fluid in the absence of administration of the anti-Bb antibody, or before administration of the anti-Bb antibody.

In some cases, an effective amount of an anti-Bb antibody of the present disclosure is an amount that is effective to inhibit complement AP-mediated lysis of a cell in the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the degree of lysis of the cell in the absence of administration of the anti-Bb antibody, or before administration of the anti-Bb antibody. In some cases, an anti-Bb antibody of the present disclosure inhibits AP-mediated lysis with an $IC_{50}$ of from $10^7$ M to $10^{-9}$ M, e.g., an $IC_{50}$ of from $10^7$ M to $5\times10^{-7}$ M, from $5\times10^{-7}$ M to $10^8$ M, from $10^8$ M to $5\times10^{-8}$ M, or from $5\times10^{-8}$ M to $10^{-9}$ M.

In some cases, an effective amount of an anti-Bb antibody of the present disclosure is an amount that is effective to inhibit complement AP-mediated hemolysis in a cell, tissue, or fluid (e.g., RBC-containing fluid) of the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the degree of hemolysis in the cell, tissue, or fluid in the absence of administration of the anti-Bb antibody, or before administration of the anti-Bb antibody. In some cases, an anti-Bb antibody of the present disclosure inhibits AP-mediated hemolysis with an $IC_{50}$ of from $10^7$ M to $10^9$ M, e.g., an $IC_{50}$ of from $10^7$ M to $5\times10^{-7}$ M, from $5\times10^{-7}$ M to $10^{-8}$ M, from $10^{-8}$ M to $5\times10^{-8}$ M, or from $5\times10^{-8}$ M to $10^{-9}$ M.

In some cases, an effective amount of an anti-Bb antibody of the present disclosure is an amount that is effective to inhibit production of an anaphylatoxin. For example, in some cases, an effective amount of an anti-Bb antibody of the present disclosure is an amount that is effective to inhibit production of C3a and C5a by least 10%, at least 20%, at least 30%, at least 40%, at least 50%, at least 60%, at least 65%, at least 70%, at least 75%, at least 80%, at least 85%, at least 90%, at least 95%, or more than 95%, compared to the amount of C3a and C5a produced in the absence of administration of the anti-Bb antibody, or before administration of the anti-Bb antibody.

In some cases, an effective amount of an anti-Bb antibody of the present disclosure is an amount that is effective to inhibit AP-mediated deposition of C3b, C3d, or other C3 split product on a cell or tissue in the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of deposition of C3b, C3d, or other C3 split product on the cell or tissue in the absence of administration of the anti-Bb antibody, or before administration of the anti-Bb antibody. In some cases, an anti-Bb antibody of the present disclosure inhibits AP-mediated deposition of C3b, C3d, or other C3 split product on a cell or tissue with an $IC_{50}$ of from $10^{-7}$ M to $10^{-9}$ M, e.g., an $IC_{50}$ of from $10^{-7}$ M to $5\times10^{-7}$ M, from $5\times10^{-7}$ M to $10^{-8}$ M, from $10^{-8}$ M to $5\times10^8$ M, or from $5\times10^8$ M to $10^9$ M.

In some cases, an effective amount of an anti-Bb antibody of the present disclosure is an amount that is effective to inhibit AP-mediated C3b deposition on a cell or tissue in the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C3b deposition on the cell or tissue in the absence of administration of the anti-Bb antibody, or before administration of the anti-Bb antibody. In some cases, an anti-Bb antibody of the present disclosure inhibits AP-mediated C3b deposition on a cell or tissue with an $IC_{50}$ of from $10^{-7}$ M to $10^{-9}$ M, e.g., an $IC_{50}$ of from $10^{-7}$ M to $5\times10^{-7}$ M, from $5\times10^{-7}$ M to $10^{-8}$ M, from $10^{-8}$ M to $5\times10^{-8}$ M, or from $5\times10^{-8}$ M to $10^{-9}$ M.

In some cases, an effective amount of an anti-Bb antibody of the present disclosure is an amount that is effective to inhibit AP-mediated deposition of C3b, C3d, or other C3 split product on RBCs in the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of deposition of C3b, C3d, or other C3 split product on RBCs in the individual in the absence of administration of the anti-Bb antibody, or before administration of the anti-Bb antibody. In some cases, an anti-Bb antibody of the present disclosure inhibits AP-mediated deposition of C3b, C3d, or other C3 split product on RBCs with an $IC_{50}$ of from $10^{-7}$ M to $10^{-9}$ M, e.g., an $IC_{50}$ of from $10^{-7}$ M to $5\times10^{-7}$ M, from $5\times10^{-7}$ M to $10^{-8}$ M, from $10^{-8}$ M to $5\times10^{-8}$ M, or from $5\times10^{-8}$ M to $10^{-9}$ M.

In some cases, an effective amount of an anti-Bb antibody of the present disclosure is an amount that is effective to inhibit AP-mediated C3b deposition on RBCs in the individual by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C3b deposition on RBCs in the individual in the absence of administration of the anti-Bb antibody, or before administration of the anti-Bb antibody. In some cases, an anti-Bb antibody of the present disclosure inhibits AP-mediated C3b deposition on RBCs with an $IC_{50}$ of from $10^{-7}$ M to $10^{-9}$ M, e.g., an $IC_{50}$ of from $10^{-7}$ M to $5\times10^{-7}$ M, from $5\times10^{-7}$ M to $10^{-8}$ M, from $10^{-8}$ M to $5\times10^{-8}$ M, or from $5\times10^{-8}$ M to $10^{-9}$ M.

In some cases, an anti-Bb antibody of the present disclosure, when administered in one or more doses to an individual in need thereof, reduces the amount of factor Bb in circulation in the individual. For example, in some cases, an anti-Bb antibody of the present disclosure, when administered in one or more doses to an individual in need thereof, reduces the amount of factor Bb in circulation in the individual by at least 10%, at least 20%, at least 30%, at least 40%, at least 50%, at least 60%, at least 65%, at least 70%, at least 75%, at least 80%, at least 85%, at least 90%, or at least 95%, compared to the amount of factor Bb in circulation in the individual in the absence of administering the anti-Bb antibody, or compared to the amount of factor Bb in circulation in the individual before administration of the anti-Bb antibody.

In some cases, an anti-Bb antibody of the present disclosure, when administered in one or more doses to an individual in need thereof, reduces the amount of factor Bb in plasma in the individual. For example, in some cases, an anti-Bb antibody of the present disclosure, when administered in one or more doses to an individual in need thereof, reduces the amount of factor Bb in plasma in the individual by at least 10%, at least 20%, at least 30%, at least 40%, at least 50%, at least 60%, at least 65%, at least 70%, at least 75%, at least 80%, at least 85%, at least 90%, or at least 95%, compared to the amount of factor Bb in plasma in the individual in the absence of administering the anti-Bb antibody, or compared to the amount of factor Bb in plasma in the individual before administration of the anti-Bb antibody.

In some cases, a method of the present disclosure to treat an individual having a complement-mediated disease or disorder comprises administering to the individual an anti-Bb antibody of the present disclosure or a pharmaceutical composition comprising: a) an anti-Bb antibody of the present disclosure; and b) a pharmaceutically acceptable excipient suitable for administration to such individual. In some cases, the individual is a mammal. In some cases, the individual is a human. Administering can be by any route known to those skilled in the art, including those disclosed herein. In some cases, administering is intravenous. In some cases, administering is intrathecal. In some cases, administering is intramuscular. In some cases, administering is subcutaneous. In some cases, the antibody is humanized.

Complement-mediated diseases and disorders that are suitable for treatment with an anti-Bb antibody of the present disclosure include diseases and disorders associated with the alternative complement pathway.

Complement-mediated diseases and disorders that are suitable for treatment with an anti-Bb antibody of the present disclosure include, but are not limited to, paroxysmal nocturnal hemoglobinuria (PNH), Idiopathic Thrombocytopenic Purpura (ITP), Thrombotic Thrombocytopenic Purpura (TTP), Hemolytic-Uremic Syndrome (HUS), Disseminated Intravascular Coagulation (DIC), Antiphospholipid Syndrome (APS), Post-Transfusion Purpura, and Neonatal Allo-Immune Thrombocytopenia (NAITP), ischemia/reperfusion injury, and age-related macular degeneration (AMD).

Complement-mediated diseases and disorders that are suitable for treatment with an anti-Bb antibody of the present disclosure include, but are not limited to, asthma, atypical Hemolytic Uremic Syndrome (aHUS), Catastrophic Anti-phospholipid Syndrome (Asherson's Syndrome; or CAPS), Dense Deposit Disease (DDD), C3 Glomerulonephritis (C3GN), age-related macular degeneration (AMD), dry AMD, wet AMD, Epidermolysis Bullosa Acquisita, Rheumatoid Arthritis, membrane proliferative glomerulonephritis type II, and Paroxysmal Nocturnal Hemoglobinuria (PNH).

In some cases, a complement-mediated disease or disorder is selected from the group consisting of ischemia-reperfusion injury, atypical hemolytic uremic syndrome, thrombotic thrombocytopenic purpura, paroxysmal nocturnal hemoglobinuria, dense deposit disease, age-related macular degeneration, spontaneous fetal loss, Pauci-immune vasculitis, epidermolysis bullosa, recurrent fetal loss, multiple sclerosis, traumatic brain injury, myasthenia gravis, cold agglutinin disease, dermatomyositis, Degos' disease, Graves' disease, Hashimoto's thyroiditis, type I diabetes, psoriasis, pemphigus, autoimmune hemolytic anemia, idiopathic thrombocytopenic purpura, Goodpasture syndrome, multifocal motor neuropathy, neuromyelitis optica, antiphospholipid syndrome, and catastrophic antiphospholipid syndrome.

AP-associated disorders and classical pathway (CP)-associated disorders include, e.g., ischemia-reperfusion injury, atypical hemolytic uremic syndrome, thrombotic thrombocytopenic purpura, paroxysmal nocturnal hemoglobinuria, dense deposit disease, age-related macular degeneration, spontaneous fetal loss, Pauci-immune vasculitis, epidermolysis bullosa, recurrent fetal loss, multiple sclerosis, traumatic brain injury, myasthenia gravis, cold agglutinin disease, dermatomyositis, Degos' disease, Graves' disease, Hashimoto's thyroiditis, type I diabetes, psoriasis, pemphigus, autoimmune hemolytic anemia, idiopathic thrombocytopenic purpura, Goodpasture syndrome, multifocal motor neuropathy, neuromyelitis optica, antiphospholipid syndrome, and catastrophic antiphospholipid syndrome.

Complement-associated disorders also include complement-associated pulmonary disorders such as, but not limited to, asthma, bronchitis, a chronic obstructive pulmonary disease (COPD), an interstitial lung disease, α-1 anti-trypsin deficiency, emphysema, bronchiectasis, bronchiolitis obliterans, alveolitis, sarcoidosis, pulmonary fibrosis, and collagen vascular disorders.

Complement-mediated diseases and disorders that are suitable for treatment with an anti-Bb antibody of the present disclosure include, but are not limited to, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases, Barraquer-Simons syndrome, Behçet's disease, British type amyloid angiopathy, bullous pemphigus, Buerger's disease, C1q nephropathy, cancer, catastrophic antiphoslpipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barré syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN), membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyclitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, lupus nephritis, bullous pemphigoid, *Epidermolysis bullosa acquisita*, delayed hemolytic transfusion reaction, and platelet refractoriness.

Combination Therapy

An anti-Bb antibody of the present disclosure can be administered to an individual in need thereof alone (e.g., as monotherapy); or in combination therapy with one or more additional therapeutic agents.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds that can be administered in the same or different formulations, by the same of different routes, and in the same or different dosage form type.

Individuals to be Treated

Individuals suitable for treatment with a subject anti-Bb antibody include individuals who have been diagnosed as having a complement-mediated disease or disorder; individuals at greater risk than the general population for developing a complement-mediated disease or disorder (e.g., individuals having a genetic predisposition to developing a complement-mediated disease or disorder); individuals with Parkinson's disease with dementia (PDD); individuals with Alzheimer's disease; individuals with paroxysmal nocturnal hemoglobinuria (PNH); individuals with Idiopathic Thrombocytopenic Purpura (ITP); individuals with Thrombotic Thrombocytopenic Purpura (TTP); individuals with Hemolytic-Uremic Syndrome (HUS); individuals with Disseminated Intravascular Coagulation (DIC); individuals with Antiphospholipid Syndrome (APS); individuals with Post-Transfusion Purpura; individuals with Neonatal Allo-Immune Thrombocytopenia (NAITP); individuals with ischemia/reperfusion injury; and individuals with age-related macular degeneration (AMD). Also included are individuals having any one of the complement-mediated diseases or disorders listed hereinabove.

In some cases, the individual is an adult human. In some cases, the adult human is 20 years or older, 30 years of age or older; 40 years of age or older, 50 years of age or older, 60 years of age or older, 70 years of age or older, or 80 years of age or older. For example, the adult human can be from 20 years old to 30 years old, from 30 years old to 40 years old, 40 years old to 50 years old, from 50 years old to 60 years old, from 60 years old to 70 years old, or older than 70 years. In some cases, the individual is a human child. In some cases, the human child is less than 20 years old, less than 10 years old, or less than 5 years old.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Production of Anti-Factor Bb Monoclonal Antibodies

Anti-factor Bb monoclonal antibodies ("factor Bb mAbs") M4, M10, M12, M17, M18, and M20 were produced as follows: Immunization of NZBW mice with purified human factor Bb protein generated a hybridoma library that was screened for binding to target using techniques known to those skilled in the art (Antibody Solutions; see, e.g., Galfre et al., Methods in Enzymology 73:346 (1981)). Flow cytometry was used to generate single cell clones, and supernatants from these individual clones were screened for preferential binding to factor Bb versus full-length Factor B by direct enzyme-linked immunosorbent assay (ELISA), such as that disclosed, e.g., in Nix et al., in Immunoassays, A Practical Approach, editor J. P. Gosling, pp. 239-261, Oxford University Press (2000). Twenty clones were selected that showed varying degrees of specific binding to factor Bb over factor B. These clones were expanded in culture, and monoclonal antibodies were purified from hybridoma supernatants. Purified mAbs were further screened for inhibition of alternative pathway (AP) activity using the Complement System Alternative Pathway WIE-SLAB kit (Euro Diagnostica, Sweden). From these results, 6 clones were chosen for further analysis.

Example 2: Binding of Anti-Factor Bb mAbs to Human Factor Bb

The relative $EC_{50}$ values for factor Bb mAbs were determined by ELISA. Unlabeled purified human Factor Bb (Complement Technologies; 1 g/mL) was coated onto a high binding ELISA plate, and incubated with increasing amounts of purified mAbs (3-fold serial dilutions starting at 10 μg/mL). Horse radish peroxidase (HRP)-conjugated goat anti-mouse secondary antibody (Southern Biotech) was used for detection, and reacted with 3,3',5,5'-Tetramethylbenzidine (TMB) 1-Step Ultra TMB-ELISA Substrate Solution (Thermo Scientific). Reactions were stopped with an equal volume of N sulfuric acid; and absorbance at $OD_{450nm}$ was measured. The data are shown in FIG. 1. The $EC_{50}$ for each monoclonal was calculated using PRISM software; the $EC_{50}$ values are listed in FIG. 2. All mAbs showed good affinity with most having an $EC_{50}$ in the subnanomolar range.

FIG. 1. Binding of purified anti-factor Bb mAbs to human factor Bb.

FIG. 2. Binding affinity of anti-factor Bb mAbs to human factor Bb

Example 3: Specificity of Anti-Factor Bb mAbs for Activated Factor Bb

Figure 3:
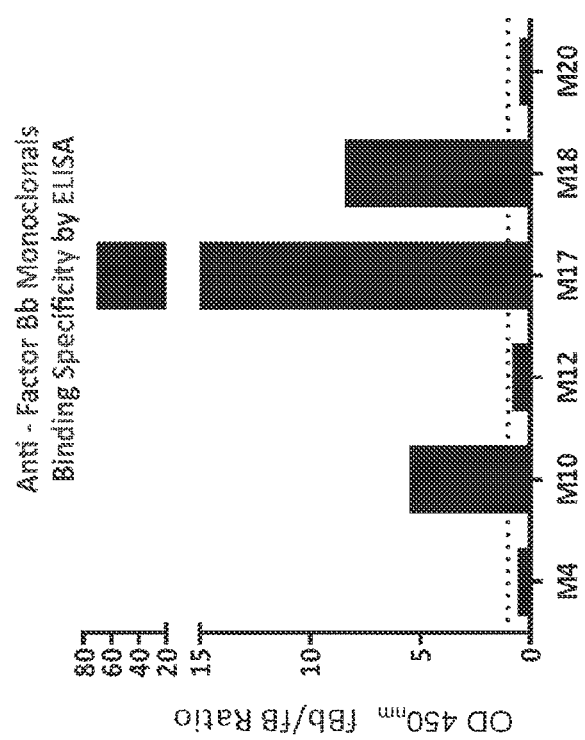
FIG. 3 depicts the ratio of binding of anti-factor Bb mAbs to soluble factor Bb versus soluble factor B.

Preferential binding of factor Bb antibodies to activated factor B versus full length Factor B zymogen was determined in an optimized antigen-capture ELISA format to evaluate binding to target soluble proteins. 1 μg/mL of antibody was bound to goat anti-mouse IgG coated plates (Pierce; Thermo Scientific), followed by incubation with 1 μg/mL biotinylated factor Bb or factor B (Complement Technologies). Bound factor Bb/B proteins were detected with streptavidin-HRP and reacted with TMB 1-Step Ultra TMB-ELISA Substrate Solution (Thermo Scientific). Reactions were stopped with an equal volume of IN sulfuric acid; and absorbance at $OD_{450nm}$ was measured. The ratio of absorbance of binding by Factor Bb versus Factor B (fBb/B ratio) was calculated and the results are shown in FIG. 3. M17 showed virtually complete specificity for factor Bb, with no detectable binding to factor B in this assay. M10 and M18 showed similar preferences in this assay (fBb/B ratio 5.5 and 8.4, respectively), while M4, M12 and M20 showed no preference (fBbB ratios ≥1).

Binding of factor Bb mAbs to full-length factor B in solution was evaluated by size exclusion chromatography (SEC). For SEC, 100 μg/mL of purified Factor B was incubated with up to 3-fold molar excess of purified mAbs. After incubation for 1 hour at room temperature (RT), samples were loaded onto a TSKgel G3000SW×1 gel filtration column. The presence of a new higher molecular weight peak in the chromatogram, and reduction of the free factor B and free antibody peaks, indicated formation of an antigen:antibody complex. Results of SEC correlate well with binding specificity determined in antigen-capture ELISA (FIG. 4). M10, M17 and M18, which showed specificity for factor Bb by ELISA, also did not bind to full-length factor B in SEC; M4, M12 and M20 showed no binding specificity by ELISA, and similarly all bind to full-length factor B in SEC.

FIG. 3. Binding of purified anti-factor Bb mAbs to soluble Factor B and Factor Bb.

FIG. 4. Specificity of binding of anti-factor Bb mAbs to factor Bb versus factor B determined by ELISA (FIG. 3) compared to results obtained by size exclusion chromatography (SEC).

Example 4: Binding of Anti-Factor Bb mAbs to Cynomolgus Monkey Proteins

Factor Bb mAbs were assayed for their ability to bind to cynomolgus monkey Factor B or Factor Bb by ELISA. 5 μg/mL of each purified protein (Innovative Research; purified in-house) was coated onto ELISA plates, incubated with purified factor Bb mAbs (3-fold serial dilutions starting at 10 μg/mL), and bound antibody was detected as in Example 2. EC values for Factor Bb versus Factor B were calculated using Prism software and are shown in FIG. 5.

FIG. 5. Binding of purified anti-factor Bb mAbs to purified cynomolgus monkey Factor B or Factor Bb.

Figure 6:
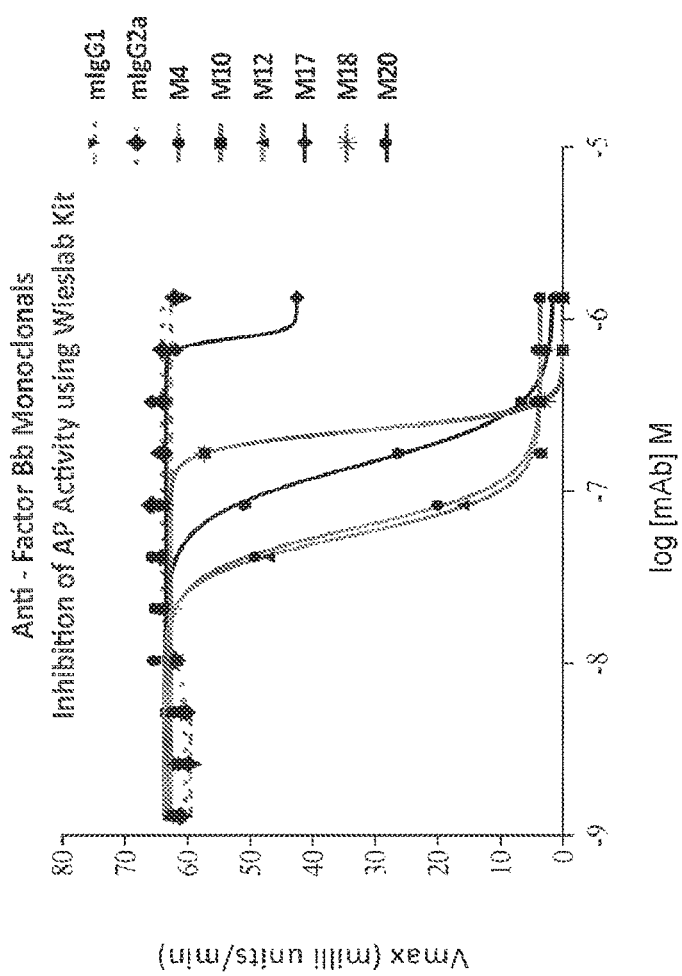
FIG. 6 depicts inhibition of complement alternative pathway (AP) activity (as determined using a Wieslab ELISA kit) by anti-factor Bb mAbs.

Example 5: Inhibition of Complement Alternative Pathway (AP) by Anti-Factor Bb mAbs Inhibition of complement AP activity by factor Bb mAbs was measured using the Complement System Alternative Pathway WIESLAB® kit. This is a plate based assay that uses lipopolysaccharide (LPS) to specifically activate the alternative pathway, and the readout is terminal membrane attack complex (MAC) deposition over time. 11% normal human serum (Complement Technologies) was incubated with 2-fold serial dilutions of mAbs or mouse isotype controls starting at 200 μg/mL. $V_{max}$ was determined for each concentration and the results are shown in FIG. 6. All anti-factor Bb monoclonal antibodies were able to inhibit AP-mediated MAC deposition, with M4/M12>M20>M10/M18>M17.

Figure 7:
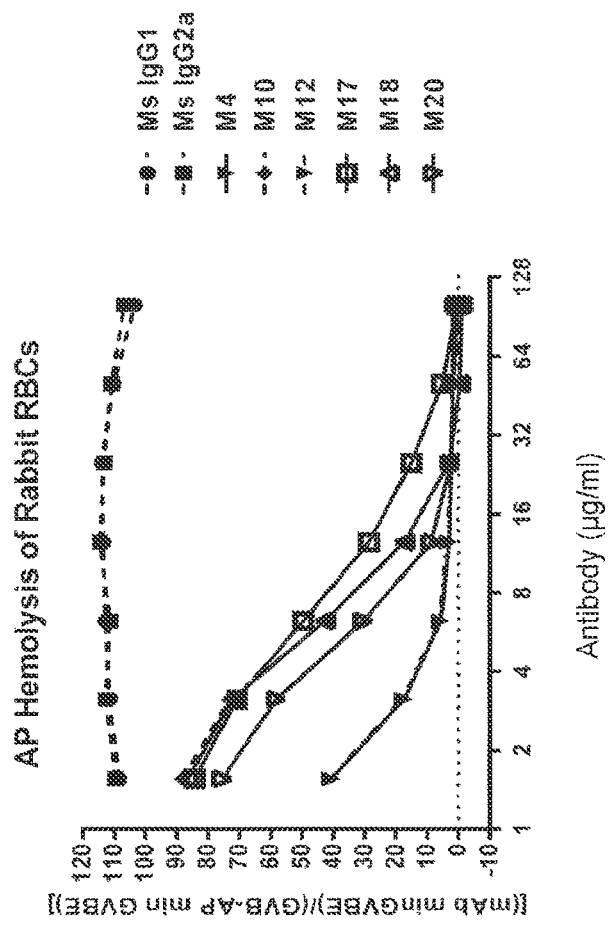
FIG. 7 depicts inhibition of AP-mediated hemolysis of rabbit red blood cells by anti-factor Bb mAbs.

Inhibition of AP pathway-mediated hemolysis and C3b deposition by factor Bb mAbs was determined using human serum and rabbit erythrocytes in buffer containing EGTA to inhibit the classical pathway. Anti-factor Bb mAbs or mouse isotype controls (2-fold dilutions starting at 100 μg/mL) were incubated with 10% human serum and rabbit red blood cells (RBCs) at 37° C. for one hour. The amount of lysis was determined by measuring the $A_{540nm}$ of the supernatant and subtracting the background absorbance in control wells containing ethylene diamine tetraacetic acid (EDTA). Results are shown in FIG. 7. All factor Bb mAbs were able to inhibit AP-mediated hemolysis, with M4/M12>M20>M10/M18>M17.

Figure 8:
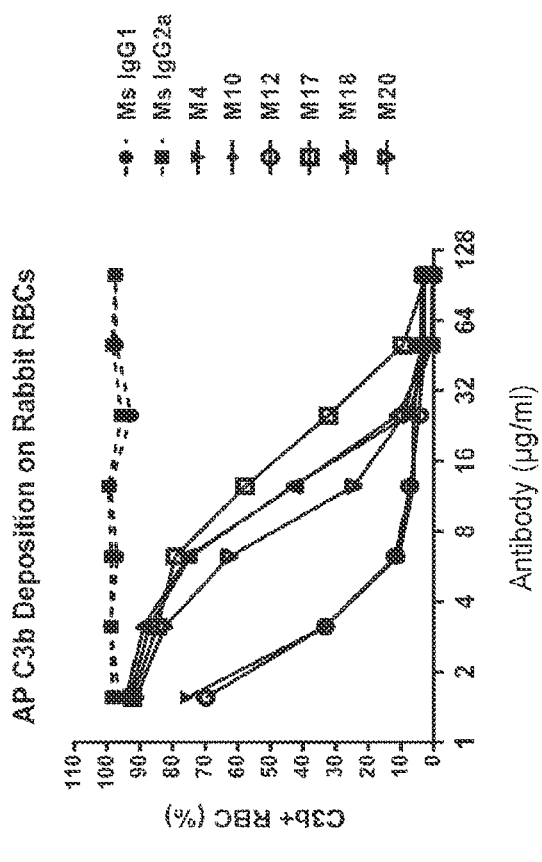
FIG. 8 depicts inhibition of AP-mediated C3b deposition on rabbit red blood cells (RBCs) by anti-factor Bb mAbs.

To assay C3 split product deposition on red blood cells (RBCs), cell pellets were stained with an anti-C3b antibody (6C9; Thermo Scientific), positive cells detected with goat anti-mouse Alexa-647 (Thermo Scientific) and analyzed by flow cytometry. Results are shown in FIG. 8. All factor Bb mAbs were able to inhibit C3 deposition on RBCs, with M4/M12>M20>M10/M18>M17.

The $IC_{50}$ values for inhibition of AP activity by factor Bb mAbs in all three assays were calculated using Prism software and are shown in FIG. 9. $IC_{50}$ values generated in the Wieslab assay were consistently higher than in the hemolysis/C3b deposition assay, perhaps due to variation in serum concentrations used in each assay or endpoint measurement differences. In particular, factor Bb-specific M17 was not very effective in the Wieslab assay compared to the hemolysis assay (17.7-fold difference in $IC_{50}$; other mAbs showed 4.4- to 5.9-fold differences in $IC_{50}$ between the two assays). However, all assays reported the same relative efficacy between anti-factor Bb mAbs, which were inversely related to their specificity for factor Bb.

FIG. 6. Inhibition of AP Activity by anti-factor Bb mAbs.

FIG. 7. Inhibition of AP pathway-mediated hemolysis by anti-factor Bb mAbs.

FIG. 8. Inhibition of AP pathway-mediated C3b deposition by anti-Factor Bb mAbs.

FIG. 9. Comparison of the effects of Factor Bb mAbs on AP activity using three different assays. Non-linear curve fits and $IC_{50s}$ were calculated using Prism software.

Example 5: Inhibition of Cynomolgus Monkey AP by Anti-Factor Bb mAbs

Figure 10:
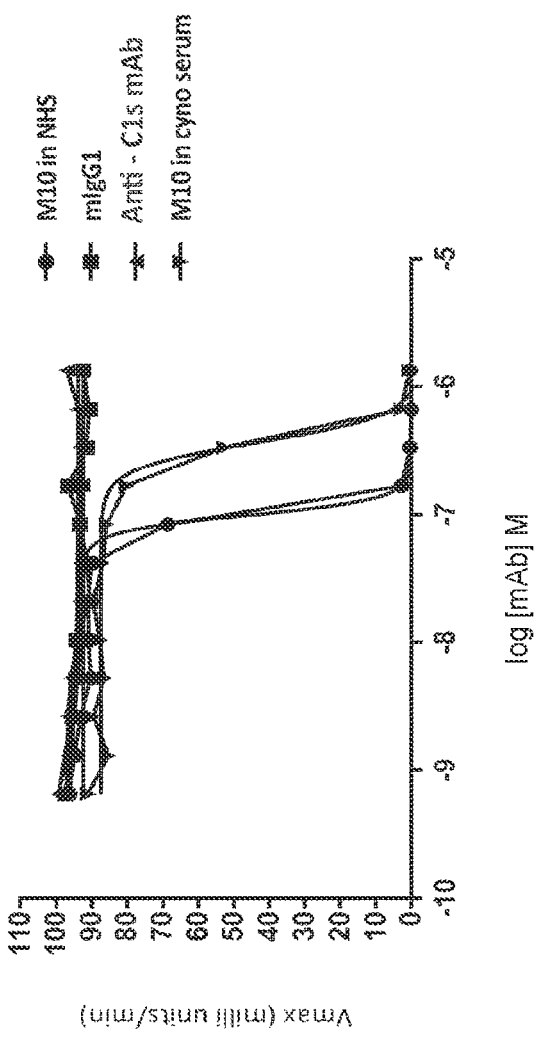
FIG. 10 depicts inhibition of cynomolgus monkey complement AP activity and human complement AP activity (Wieslab ELISA kit) by an anti-factor Bb mAb.

Inhibition of complement alternative pathway activity (AP) by anti-factor Bb mAb M10 was measured using the Complement System Alternative Pathway WIESLAB® kit. Normal human serum or cynomolgus ("cyno") monkey serum (Innovative Research; 5.5%) was incubated with 2-fold serial dilutions of M10 or mouse isotype controls starting at 100 g/mL. $V_{max}$ was determined for each concentration and the results are shown in FIG. 10. The $IC_{50}$ for M10 in this experiment was 9.79E-8 and 3.67E-7 M for human and cyno serum, respectively.

Figure 11:
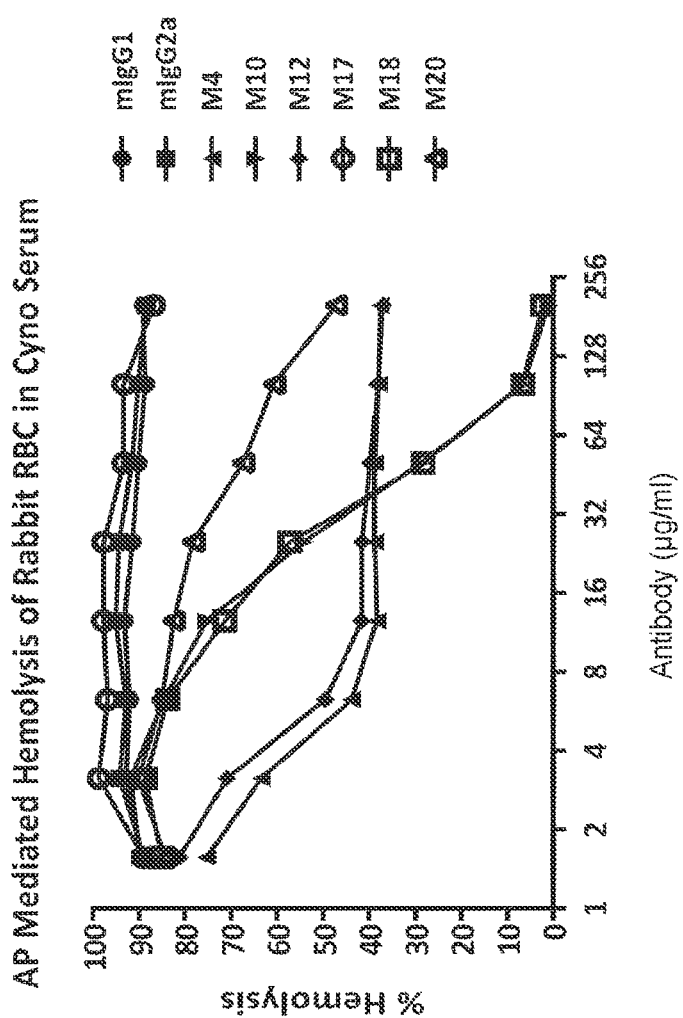
FIG. 11 depicts inhibition of cynomolgus monkey AP-mediated hemolysis of rabbit red blood cells by anti-factor Bb mAbs.

Inhibition of AP pathway mediated hemolysis by anti-Factor Bb mAbs was measured using cynomolgus serum and rabbit erythrocytes in buffer containing EGTA to inhibit the classical pathway. Anti-factor Bb mAbs or mouse isotype controls (2-fold dilutions starting at 100 µg/mL) were incubated with 5% cynomolgus monkey serum and rabbit RBCs at 37° C. for one hour. The amount of lysis was determined by measuring the $A_{540nm}$ of the supernatant and subtracting the background absorbance in control wells containing EDTA. Results are shown in FIG. 11. M17 does not inhibit cyno serum mediated hemolysis of rabbit red blood cells. $IC_{50}$ values for cyno serum were as follows: 2.497E-8 (M4), 2.202E-7 (M10), 2.824E-8 (M12), 2.319E-7 (M18) and 7.524E-7 M (M20).

FIG. 10. Inhibition of Wieslab AP Activity in human or monkey serum by anti-Factor Bb mAbs.

FIG. 11. Inhibition of cyno AP pathway mediated hemolysis of rabbit RBCs by anti-factor Bb mAbs.

Example 6: Sequencing of Anti-Factor Bb mAbs

Amino acid sequencing of the VH and VL regions of the factor Bb mAbs was conducted using techniques known to those skilled in the art (LakePharma). Specifically, cell pellets were prepared from the hybridoma cell lines and RNA was extracted. V-regions were amplified by reverse transcription-polymerase chain reaction (RT-PCR) using degenerate primer pools for murine antibody signal sequences together with constant region primers for IgMVH, IgGVH, IgxVL and IgXVL. The polymerase chain reaction (PCR) products obtained from each of the successful amplifications were purified and cloned into a 'TA' cloning vector system from which sequences were obtained. The deduced amino acid sequences of the VH and VL regions, as well as the CDRs, of the factor Bb mAbs are provided in FIGS. 12A-12F. M10 and M18 VL and VH are identical in sequence, and M4 and M12 VH and VL are identical in sequence.

Example 7: Further Characterization of Anti-Bb mAbs

Figure 14:
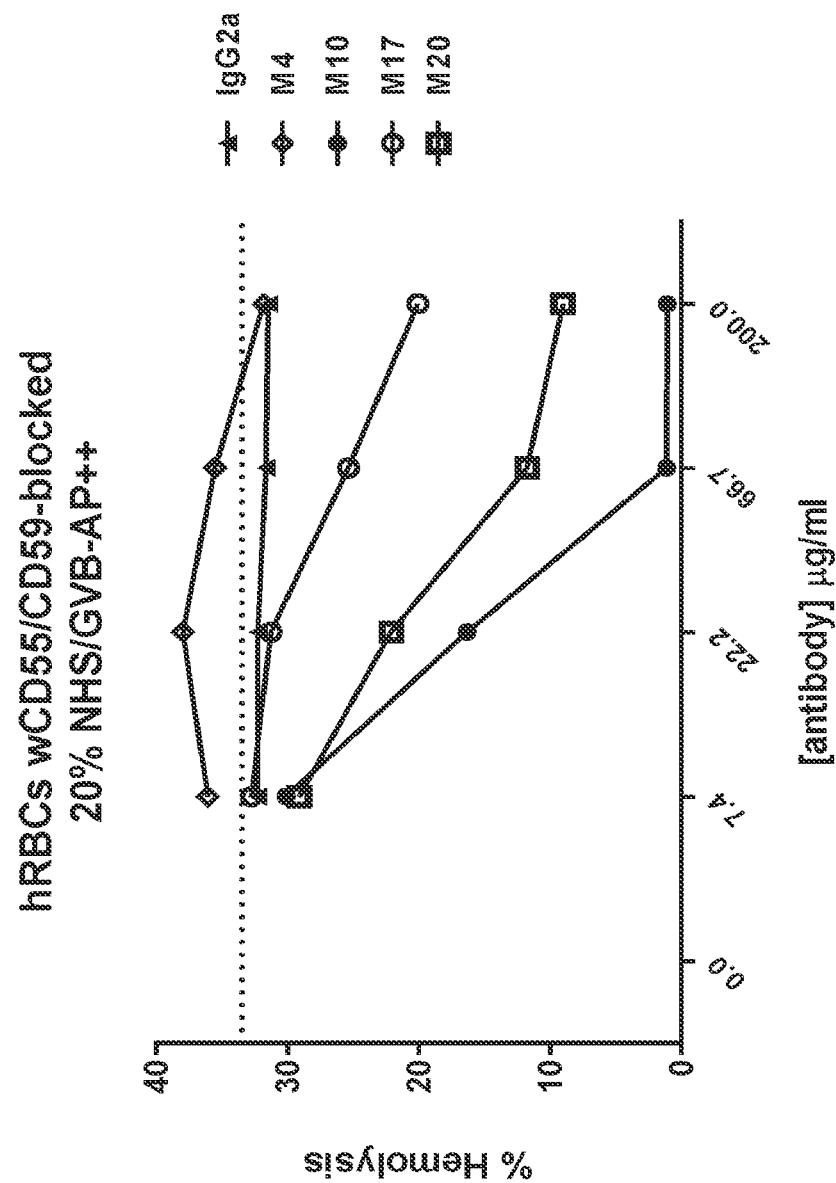
FIG. 14 depicts inhibition of AP pathway-mediated hemolysis by Factor Bb antibodies of the present disclosure on human RBCs pre-treated with CD55/CD59 antibodies.

Inhibition of AP Pathway-Mediated Hemolysis by Factor Bb Antibodies on Human RBCs Pre-Treated with CD55/CD59 Antibodies (FIG. 14)

Patients with Paroxysmal Nocturnal Hemoglobinuria (PNH) suffer from complement mediated lysis of their red blood cells (RBCs) due to the lack of complement regulators (CD55 and CD59) on the cell surface. Pre-treatment with neutralizing antibodies to CD55 and CD59 renders healthy RBCs susceptible to complement mediated lysis.

Normal human erythrocytes pre-treated with anti-CD55 and CD59 antibodies were incubated with 20% normal human serum containing varying concentrations of Factor Bb antibodies M4. M10, M17 and M20 as well as mouse IgG2a (isotype control). The reaction buffer contained 10 mM Mg EGTA to block the classical and lectin complement pathways. After 120 minutes at 37° C., the cells were centrifuged. The amount of lysis was determined by measuring the $A_{540nm}$ of the supernatant and subtracting the background absorbance in control wells containing EDTA. The results are shown in FIG. 14. Complete inhibition of hemolysis was only obtained with the M10 antibody.

Production of Anti-Factor Bb Chimeric Antibodies

Utilizing the DNA sequences from example 6, the variable domains for hybridoma clones M4 and M10 were synthesized (DNA 2.0) along with additional flanking sequences needed for cloning. The variable domains were cloned into expression vectors that generated a chimeric antibody composed of mouse variable regions and human IgG4 constant/Fc regions. The constructs were transfected into HEK293 cells and purified from culture supernatants using Protein A Sepharose. The chimeric antibody containing the variable region of M10 is referred to as "chimeric M10." The chimeric antibody containing the variable region of M4 is referred to as "chimeric M4."

Figure 15:
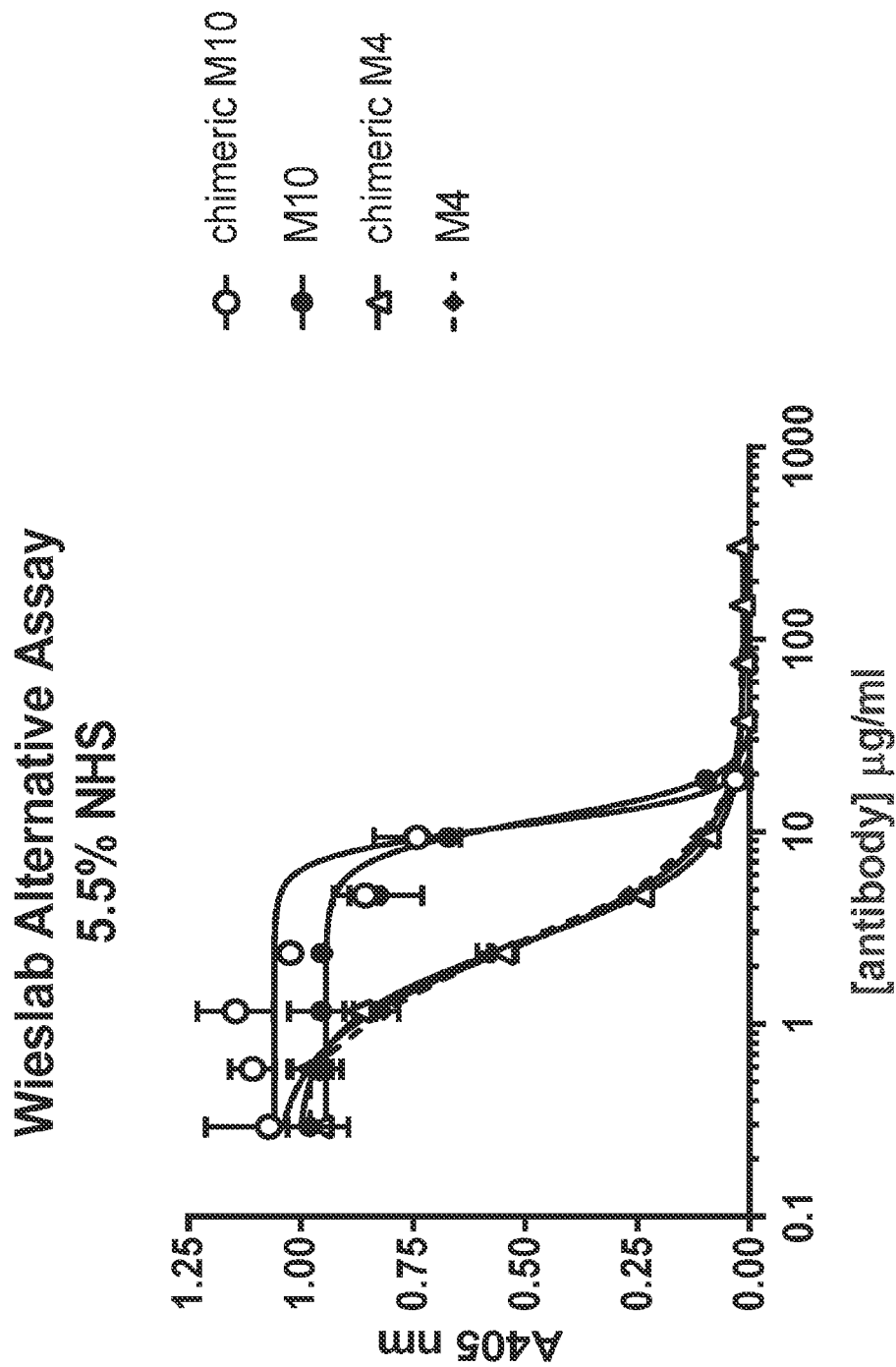
FIG. 15 depicts inhibition of Complement Alternative Pathway (AP) by Factor Bb chimeric antibodies chimeric M10 and chimeric M4.

Inhibition of Complement Alternative Pathway (AP) by Factor Bb Chimeric Antibodies (FIG. 15)

Inhibition of complement AP activity by Factor Bb chimeric antibodies chimeric M10 and chimeric M4 was measured using the Complement System Alternative Pathway WIESLAB® kit. 11% normal human serum (NHS; Complement Technologies) was incubated with 2-fold serial dilution of the chimeric antibodies or their parental monoclonal mouse antibodies, starting at 300 µg/ml. At the end of the assay, the A405 was measured. The data are shown in FIG. 15. The A405 was proportional to the amount of terminal membrane attack complex (MAC) deposited on the plate. The A405 was plotted versus antibody concentration. The chimeric antibodies were found to have similar potencies in the Wieslab Alternative Pathway assay when compared to their corresponding parental monoclonal mouse antibodies.

Figure 16:
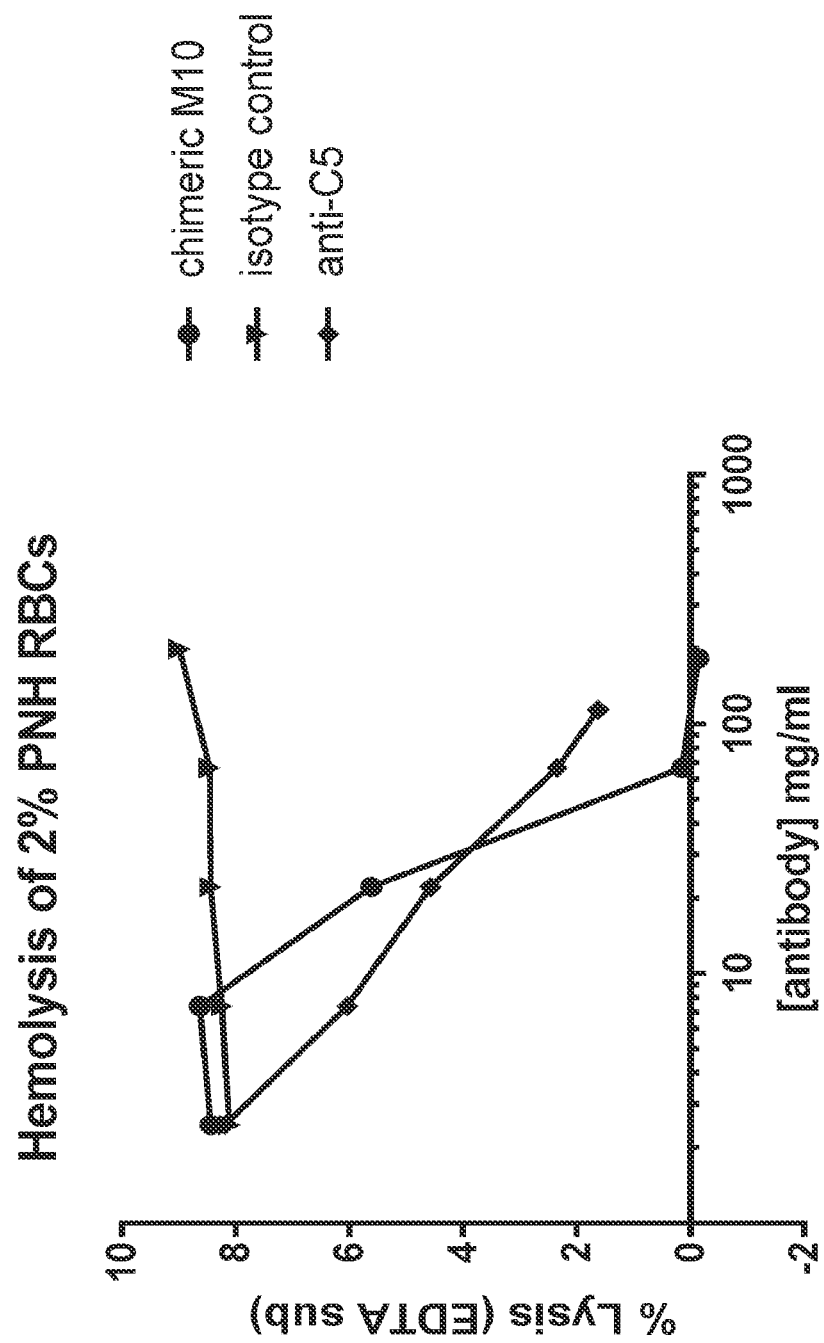
FIG. 16 depicts inhibition of AP pathway-mediated hemolysis by anti-Factor Bb chimeric antibody chimeric M10 on RBCs from a Patient with Paroxysmal Nocturnal Hemoglobinuria (PNH).

Inhibition of AP Pathway-Mediated Hemolysis by Factor Bb Chimeric Antibody on RBCs from a Patient with Paroxysmal Nocturnal Hemoglobinuria (PNH) (FIG. 16)

Human erythrocytes from a PNH patient were incubated with 20% O+ human serum containing varying concentrations of chimeric M10 (human/mouse chimeric of M10), anti-human C5 antibody, or human IgG4 (isotype control). The reaction buffer contained 10 mM Mg EGTA to block the classical and lectin complement pathways. After 180 minutes at 37° C., the cells were centrifuged. The amount of lysis was determined by measuring the $A_{540nm}$ of the supernatant and subtracting the background absorbance in control wells containing EDTA. The results are shown in FIG. 16. Complete inhibition of hemolysis was obtained only with the chimeric M10 antibody.

Figure 17:
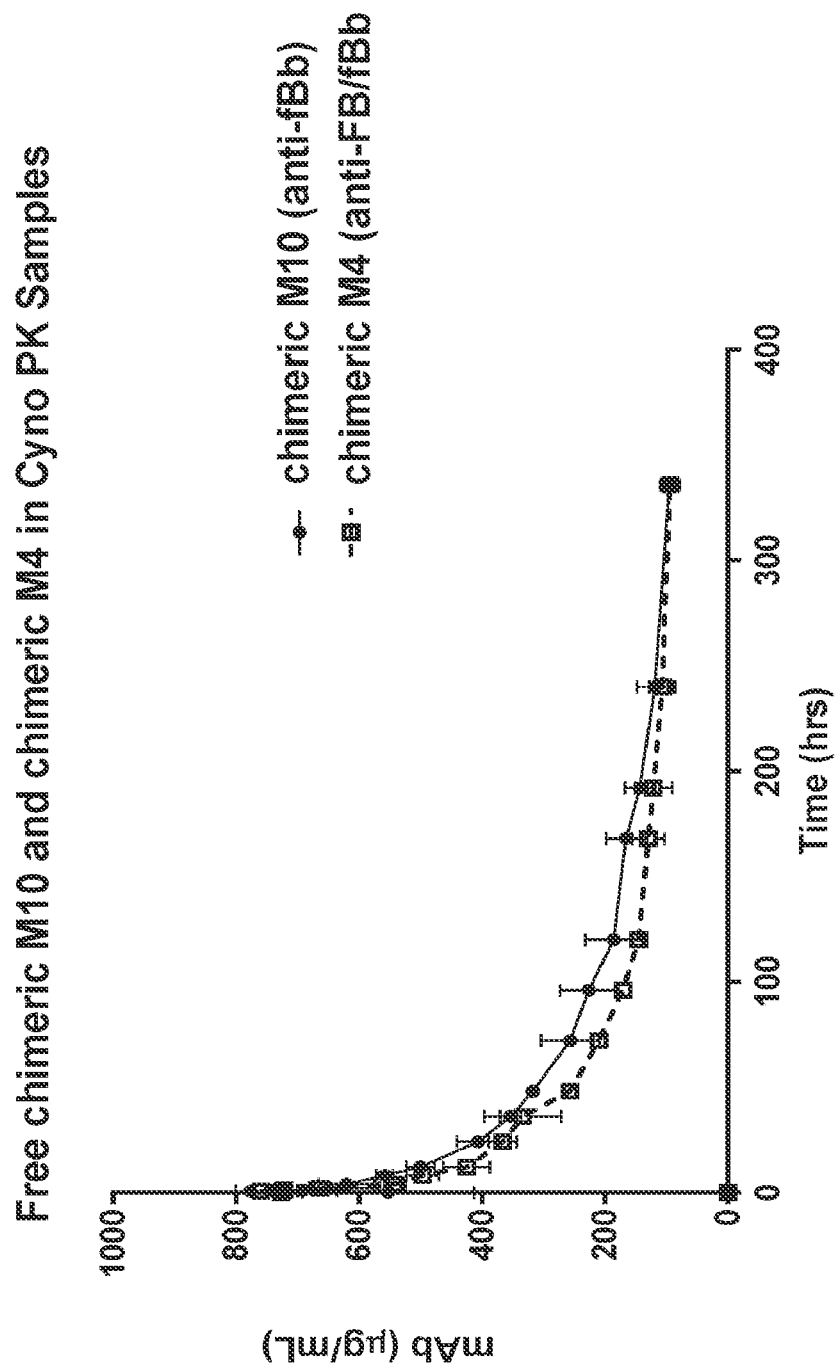
FIG. 17 depicts pharmacokinetics (PK) of anti-Factor Bb chimeric antibodies chimeric M10 and chimeric M4 in cynomolgus monkeys.

Pharmacokinetics of Factor Bb Chimeric Antibodies in Cynomolgus Monkeys (FIG. 17)

To determine the pharmacokinetic properties of the Factor Bb antibodies in cynomolgus monkeys, chimeric M10 and chimeric M4 were each intravenously injected into 3 monkeys at 30 mg/kg. At various times post injection, plasma samples were taken for analysis. Free chimeric M10 or chimeric M4 in diluted plasma samples were captured with Factor Bb (fBb) protein on a high-binding enzyme immunoassay (EIA) microtiter plate. Captured antibody was detected with a goat anti-human IgG secondary antibody conjugated with horseradish peroxidase (HRP) enzyme. The microtiter plates were washed to remove any unbound reactants and tetramethylbenzidine (TMB) substrate was then reacted with the immobilized HRP to yield a chromogenic product. The absorbance of this chromogenic product at wavelength of 450 nm was directly proportional to the concentration of chimeric M10 or chimeric M4 in the sample. Data from the ELISA were analyzed using the XY plotting function and 4-Parameter Logistic (4PL) linear regression function in GraphPad Prism software to determine the amount of free chimeric M10 or chimeric M4 present at each time point after dosing. The data are shown in FIG. 17.

Figure 18:
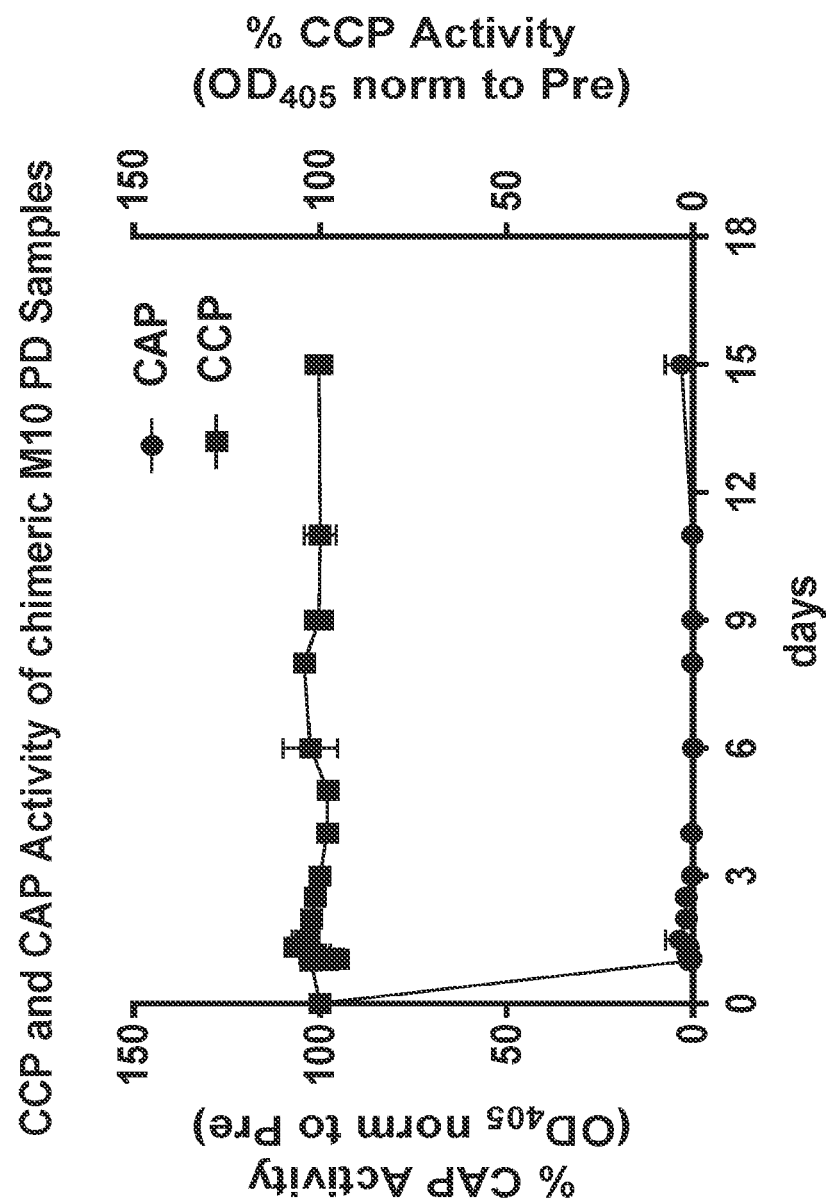
FIG. 18 depicts pharmacodynamics (PD) of anti-Factor Bb chimeric antibody M10 in cynomolgus monkeys.
Figure 19:
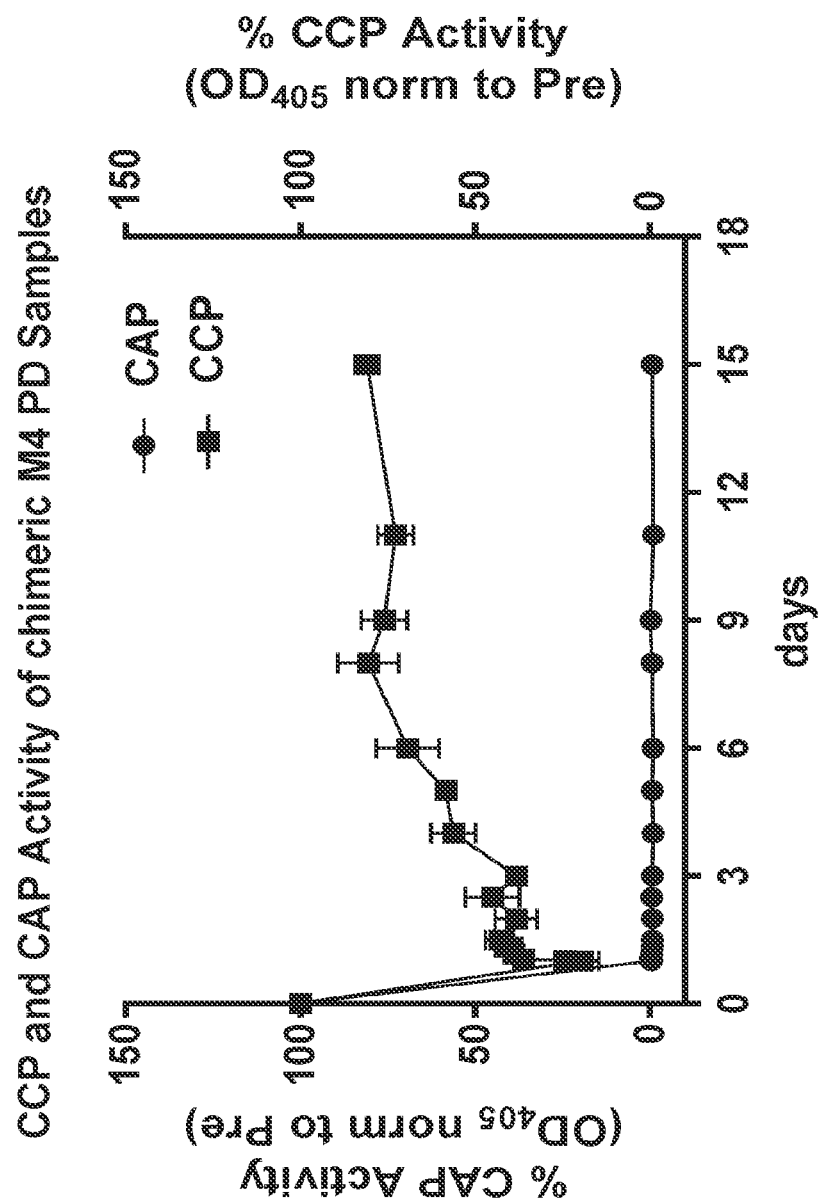
FIG. 19 depicts pharmacodynamics of anti-Factor Bb chimeric antibody M4 in cynomolgus monkeys.

Pharmacodynamics of Factor Bb Chimeric Antibodies in Cynomolgus Monkeys (FIG. 18 and FIG. 19)

To determine the pharmacodynamic properties of the Factor Bb antibodies in cynomolgus monkeys, chimeric M10 and chimeric M4 were each intravenously injected into 3 monkeys at 30 mg/kg. At various times post injection, serum samples were taken for analysis. The complement alternative pathway (CAP) and classical pathway (CCP) activities of the serum samples were determined using the Complement System Alternative Pathway and Classical Pathway WIESLAB® Kits, respectively, following the manufacturer's suggested instructions. Serum concentration of 5.5% and 0.99% were used in the alternative and classical pathway assays, respectively. The graphs provided in FIG. 18 and FIG. 19 are normalized to the activity of the serum prior to antibody injection. As shown in FIG. 18, chimeric M10 inhibits CAP activity, but not CCP activity. As shown in FIG. 19, chimeric M4 inhibits CAP activity, and inhibits CCP activity to a lesser extent than the inhibition of CAP activity.

Figure 20:
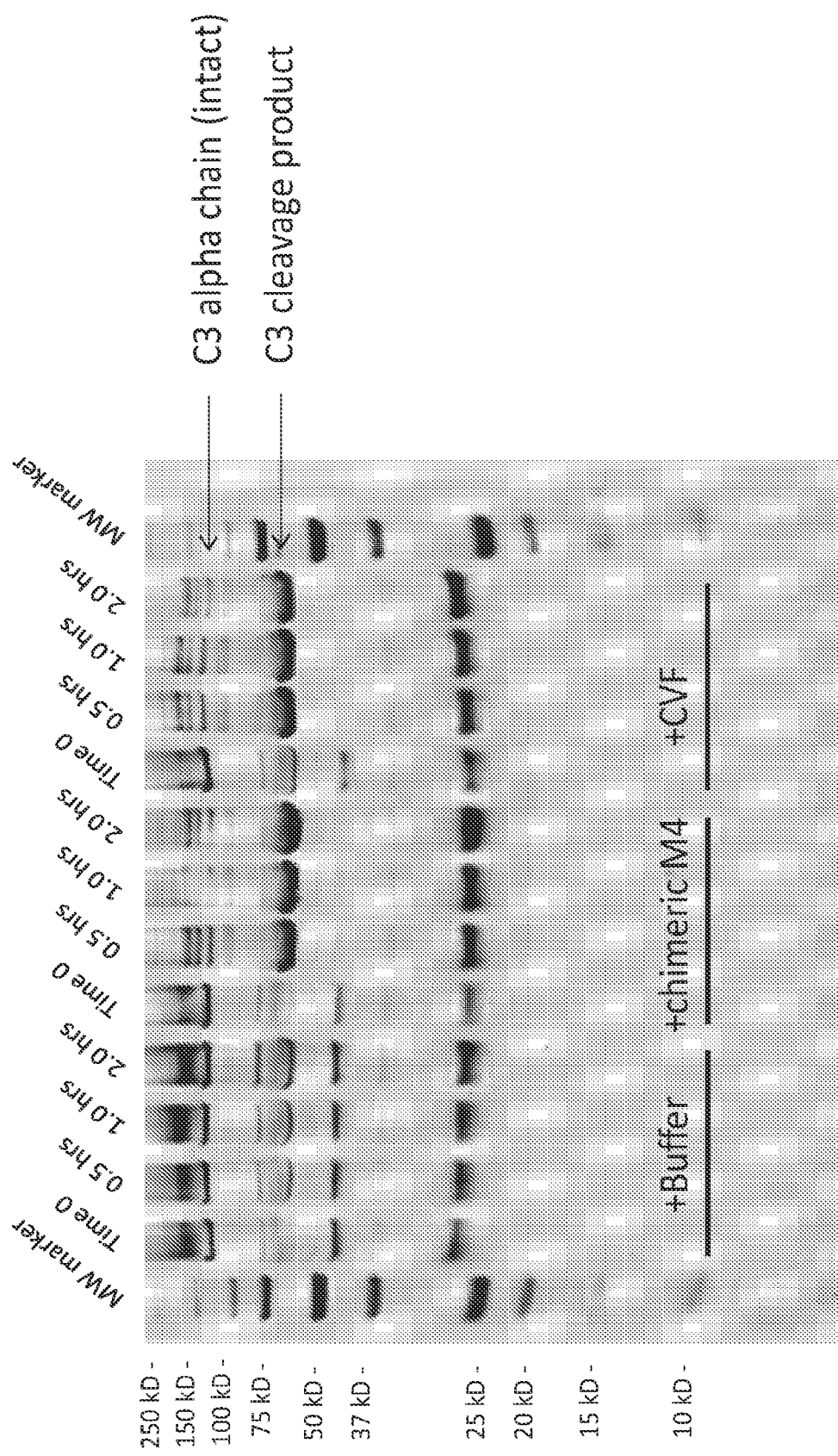
FIG. 20 depicts chimeric anti-factor Bb chimeric M4-induced C3 degradation in in human serum in vitro.

Chimeric M4 Induces C3 Degradation in Human Serum In Vitro (FIG. 20)

Chimeric M4 was added to normal human serum at a concentration of 0.1 mg/ml and incubated at 37° C. At various time points, a sample was taken for Western blot analysis with a rabbit anti-human C3 polyclonal antibody. As a negative control, buffer was added to serum. As a positive control, cobra venom factor (CVF), a protein known to induce C3 degradation, was added to normal human serum. As shown in FIG. 20, similar to cobra venom factor, chimeric M4 induced C3 degradation in a time dependent manner.

Chimeric M4 Induces C3 Degradation in Cynomolgus Monkeys In Vivo (FIG. 21)

Cynomolgus monkey serum samples from the 30 mg/kg injection of chimeric M10 and chimeric M4 were assayed for C3 levels using a sandwich ELISA. Briefly, purified goat-anti human C3 antibody was coated onto high binding ELISA plates. After blocking, the plates were incubated with plasma samples taken from the various time points after injection of chimeric M10 and chimeric M4 into monkeys. After washing, the plates were then incubated with biotinylated rabbit anti-human C3a antibody. After an additional wash, the plates were incubated with Streptavidin-horse radish peroxidase (HRP). The microtiter plates were washed to remove any unbound reactants and tetramethylbenzidine (TMB) substrate was then reacted with the immobilized HRP to yield a chromogenic product. The absorbance of this chromogenic product at wavelength of 450 nm is directly proportional to the concentration of C3 in the sample. As shown in FIG. 21 (upper panel), no changes in C3 levels were observed upon injection of chimeric M10. As shown in FIG. 21 (lower panel), rapid loss of C3 was observed upon injection of chimeric M4.

Figure 22:
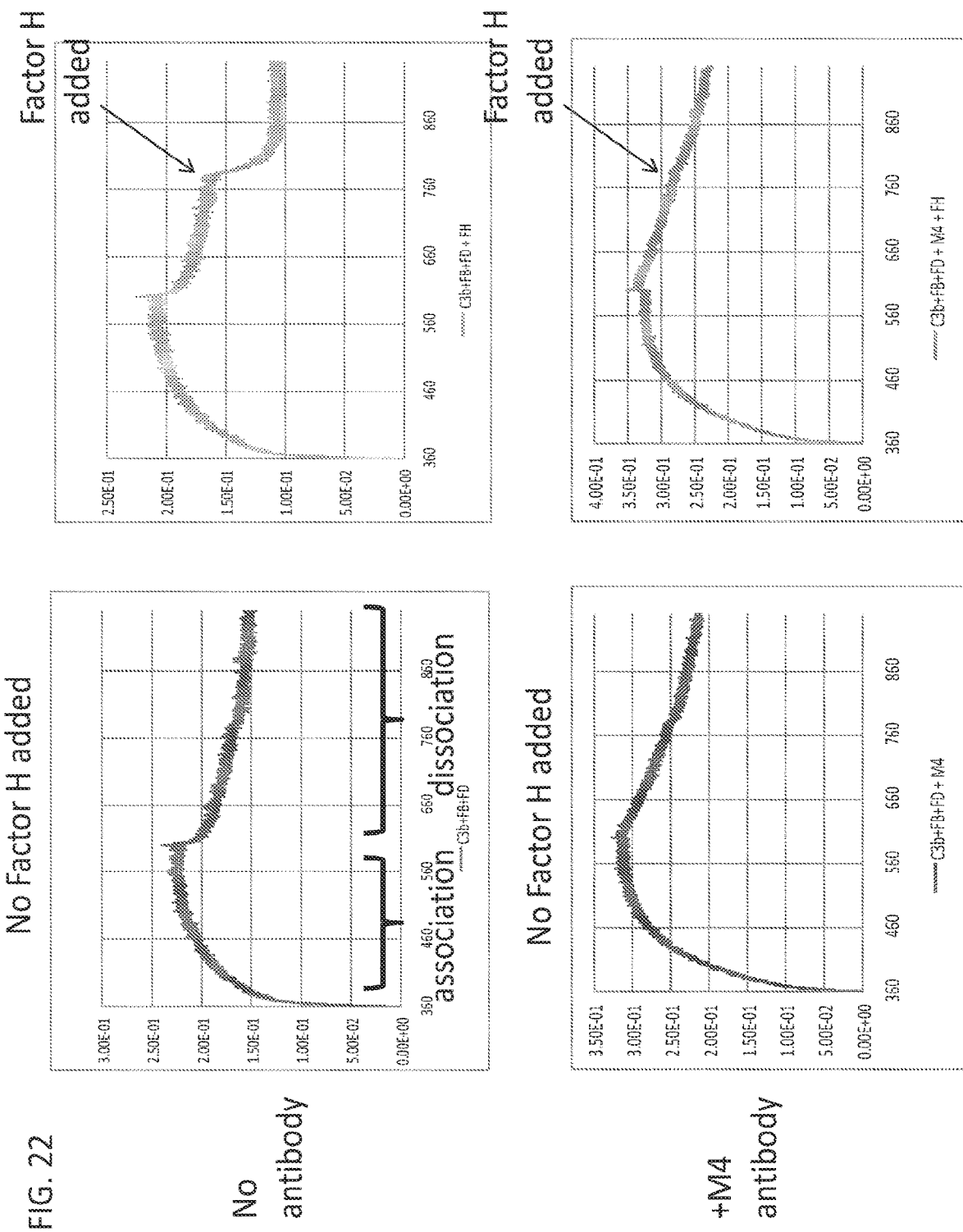
FIG. 22 depicts anti-factor Bb antibody M4 blockage of the Decay Accelerating Factor (DAF) activity of factor H.

Factor B/Bb Antibody M4 Blocks the Decay Accelerating Factor (DAF) Activity of Factor H (FIG. 22)

Using the Octet System (Pall ForteBio), the effect of the Factor B/Bb antibody M4 on the dissociation rate of the C3 Convertase by Factor H (FH) was examined. Briefly, biotinylated properdin was prepared and bound to Octet probes coated with Streptavidin. Afterwards, the bound properdin probes were incubated in C3 convertase containing solution that was prepared by mixing C3b, Factor B (FB), and Factor D (FD). As the C3 convertase binds the properdin probe, the association was measured. Then the probe was transferred to a solution containing only buffer to measure the dissociation of the C3 convertase from the properdin bound probe. As shown in FIG. 22, when Factor H was added during the dissociation step, rapid dissociation of the C3 convertase from the properdin probe could be measured (top right). As shown in FIG. 22, when the C3 convertase was prepared in the presence of M4, the rapid dissociation of the C3 convertase by Factor H was not observed.

Figure 23:
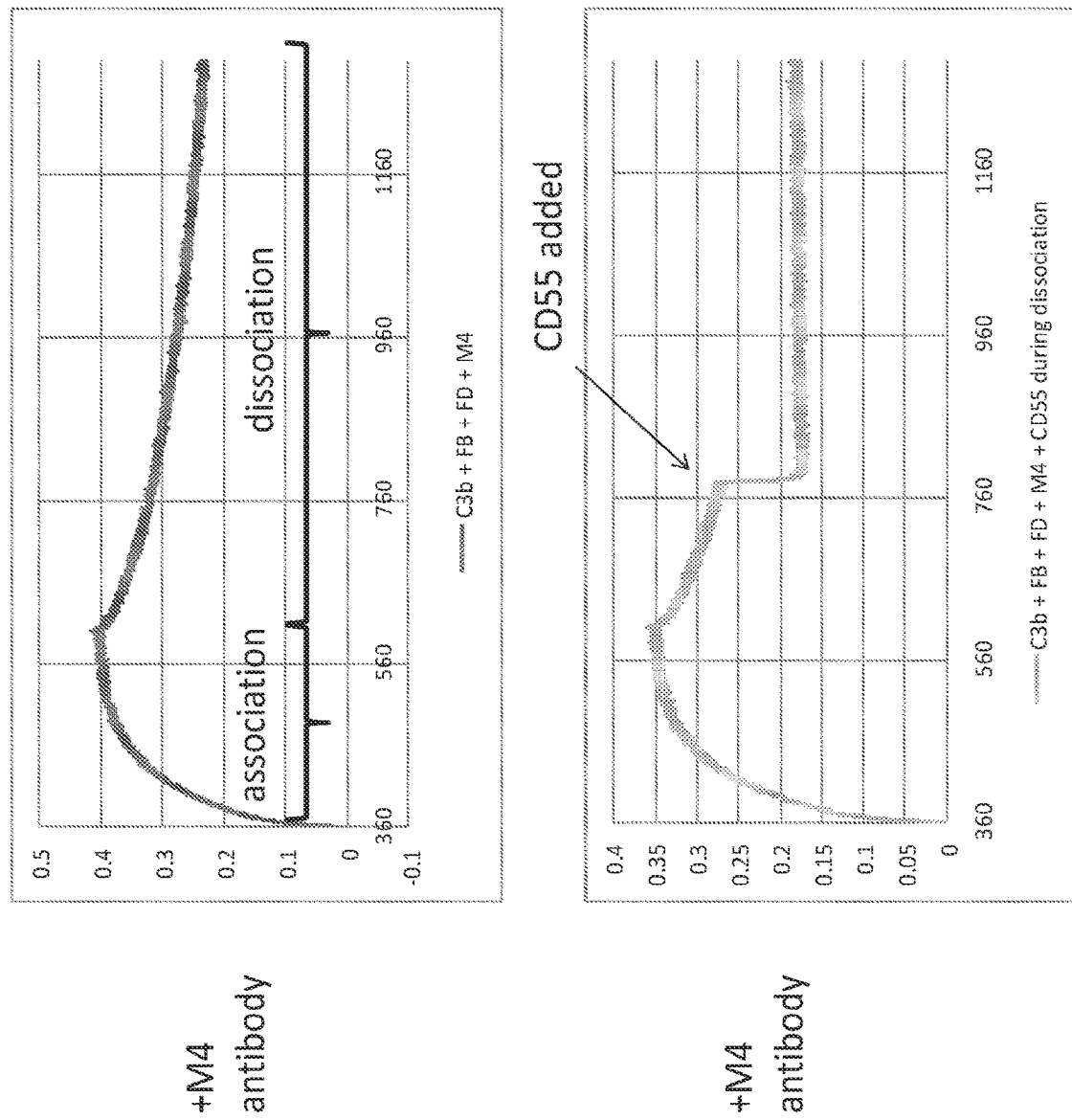
FIG. 23 depicts the effect of anti-factor Bb M4 on DAF activity of CD55.

Factor B/Bb Antibody M4 does not Block the DAF Activity of CD55 (FIG. 23)

Using the Octet System (Pall ForteBio), examined the effect of the Factor B/Bb antibody M4 on the dissociation rate of the C3 Convertase by CD55 was examined. Briefly, biotinylated properdin was prepared and bound to Octet probes coated with Streptavidin. Then the bound properdin probes were incubated in C3 convertase (with bound Factor B/Bb antibody M4) containing solution that was prepared by mixing C3b, Factor B, Factor B/Bb antibody M4 and Factor D. As the C3 convertase (with bound antibody) binds the properdin probe, the association was measured. Then the probe was transferred to a solution containing only buffer to measure the dissociation of the C3 convertase (with bound antibody) from the properdin bound probe. As shown in FIG. 23, when CD55 was added during the dissociation step, rapid dissociation of the C3 convertase (with bound antibody) from the properdin probe could be measured (bottom). The data indicate that the binding of the Factor B/Bb antibody to the C3 convertase does not block the ability of CD55 to dissociate the C3 convertase complex.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

<160> NUMBER OF SEQ ID NOS: 98

<210> SEQ ID NO 1
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 1

Gln Asp Val Gly Thr Ala
1               5

<210> SEQ ID NO 2
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 2

Trp Ala Ser
1

<210> SEQ ID NO 3
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 3

His Gln His Ser Ser Asn Pro Leu Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 4

Gly Phe Thr Phe Ser Asn Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 5

Ile Ser Asn Arg Gly Ser Tyr Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 6

Ala Arg Glu Arg Pro Met Asp Tyr
1               5

<210> SEQ ID NO 7
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 7

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Val Tyr Phe Cys His Gln His Ser Ser Asn Pro Leu
                85                  90                  95

Thr Phe Gly Ala Gly Thr Lys Leu Glu Leu Lys
            100                 105
```

<210> SEQ ID NO 8
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 8

```
Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Asn Arg Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Glu Arg Pro Met Asp Tyr Trp Gly Gln Gly Thr Ser Val Thr
            100                 105                 110

Val Ser Ser
        115
```

<210> SEQ ID NO 9
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 9

```
Lys Ser Leu Leu His Ser Asn Gly Ile Thr Tyr
1               5                   10
```

```
<210> SEQ ID NO 10
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 10

Arg Met Ser
1

<210> SEQ ID NO 11
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 11

Ala Gln Met Leu Glu Arg Pro Trp Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 12

Gly Tyr Ser Phe Thr Asp Tyr Leu
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 13

Ile Asn Pro Tyr Asn Gly Asp Ala
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 14

Ala Arg Leu Glu Asn Asp Tyr Gly Phe Thr Tyr
1               5                   10

<210> SEQ ID NO 15
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 15

Asp Ile Val Met Thr Gln Ala Ala Phe Ser Asn Pro Val Thr Leu Gly
1               5                   10                  15

Thr Ser Ala Ser Ile Ser Cys Ser Ser Ser Lys Ser Leu Leu His Ser
```

20                  25                  30

Asn Gly Ile Thr Tyr Leu Tyr Trp Tyr Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Leu Glu Arg Pro Trp Thr Phe Gly Gly Gly Thr Lys Leu Glu Ile Lys
            100                 105                 110

<210> SEQ ID NO 16
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 16

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Asp Tyr
                20                  25                  30

Leu Met Asn Trp Val Lys Gln Ser His Gly Lys Ser Leu Glu Trp Ile
            35                  40                  45

Gly Arg Ile Asn Pro Tyr Asn Gly Asp Ala Phe Tyr Asn Gln Arg Phe
        50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Leu Tyr Tyr Cys
                85                  90                  95

Ala Arg Leu Glu Asn Asp Tyr Gly Phe Thr Tyr Trp Gly Gln Gly Thr
            100                 105                 110

Leu Val Thr Val Ser Ala
        115

<210> SEQ ID NO 17
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 17

Gln Gly Ile Asn Asn Tyr
1               5

<210> SEQ ID NO 18
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 18

Tyr Thr Ser
1

<210> SEQ ID NO 19

```
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 19

Gln Gln His Ser Lys Leu Pro Trp Thr
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 20

Gly Phe Ser Leu Ser Thr Phe Gly Leu Gly
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 21

Ile Trp Trp Asn Asp Asp Lys
1               5

<210> SEQ ID NO 22
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 22

Val Gln Ile Pro Tyr Gly Ser Arg Asn Gly Phe Asp Tyr
1               5                   10

<210> SEQ ID NO 23
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 23

Thr His Tyr Arg Ala Ser Ser Gly Ile Asn Ala Glu Tyr Met Gly Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Val Ala Thr Tyr Tyr Cys Gln Gln His Ser Lys Leu Pro Trp
                85                  90                  95

Thr Phe Gly Gly Gly Thr Lys Leu Glu Ile Lys
```

<210> SEQ ID NO 24
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 24

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Leu Gly Val Gly Trp Ile Arg Gln Pro Ser Gly Lys Gly Leu Glu
        35                  40                  45

Trp Leu Ala Ser Ile Trp Trp Asn Asp Asp Lys Tyr Tyr Asn Ser Asp
    50                  55                  60

Leu Lys Arg Arg Pro Thr Ile Ser Arg Asp Thr Ser Asn Ser Gln Val
65                  70                  75                  80

Phe Leu Lys Ile Ser Ser Val Asp Thr Ala Asp Thr Ala Thr Tyr Phe
                85                  90                  95

Cys Val Gln Ile Pro Tyr Gly Ser Arg Asn Gly Phe Asp Tyr Trp Gly
            100                 105                 110

Gln Gly Thr Ser Leu Thr Val Ser Ser
        115                 120

<210> SEQ ID NO 25
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 25

Gln Asp Val Gly Ser Ala
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 26

Gln Gln Tyr Ser Ser Tyr Pro Tyr Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 27

Gly Phe Thr Phe Ser Asn Phe Ala
1               5

<210> SEQ ID NO 28
<211> LENGTH: 8
<212> TYPE: PRT

<213> ORGANISM: Artificial Sequence
<220> FEATURE:
<223> OTHER INFORMATION: Synthetic Sequence

<400> SEQUENCE: 28

Ile Ser Asn Gly Gly Gly Tyr Thr
1               5

<210> SEQ ID NO 29
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 29

Ala Arg Ile Tyr Tyr Gly Ser Ser Tyr Glu Asp Trp Phe Ala Tyr
1               5                   10                  15

<210> SEQ ID NO 30
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 30

Asp Ile Val Met Thr Pro Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly His Ser Pro Lys Leu Leu Ile
        35                  40                  45

Phe Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Arg Leu Glu Ile Lys
            100                 105

<210> SEQ ID NO 31
<211> LENGTH: 122
<212> TYPE: PRT
<213> ORGANISM: Artificial Sequence
<220> FEATURE:
<223> OTHER INFORMATION: Synthetic Sequence

<400> SEQUENCE: 31

Glu Val Gln Leu Val Glu Ser Gly Gly Val Leu Val Lys Pro Gly Gly
1               5                   10                  15

Ser Leu Lys Leu Ser Cys Ala Ala Ser Gly Phe Thr Phe Ser Asn Phe
            20                  25                  30

Ala Met Ser Trp Val Arg Gln Thr Pro Ala Lys Arg Leu Glu Trp Val
        35                  40                  45

Ala Thr Ile Ser Asn Gly Gly Gly Tyr Thr Tyr Tyr Pro Asp Ser Val
    50                  55                  60

Gln Gly Arg Phe Thr Ile Ser Arg Asp Asn Ala Asn Asn Thr Leu Tyr
65                  70                  75                  80

Leu Gln Met Ser Ser Leu Arg Ser Glu Asp Thr Ala Leu Tyr Tyr Cys

```
                    85                  90                  95
Ala Arg Ile Tyr Tyr Gly Ser Ser Tyr Glu Asp Trp Phe Ala Tyr Trp
                100                 105                 110

Gly Gln Gly Thr Leu Val Thr Val Ser Ala
        115                 120
```

<210> SEQ ID NO 32
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 32

Ala Ala Ala Ala
1

<210> SEQ ID NO 33
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 33

Ala Ala Ala Ala
1

<210> SEQ ID NO 34
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 34

Ala Ala Ala Ala
1

<210> SEQ ID NO 35
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 35

Ala Ala Ala Ala
1

<210> SEQ ID NO 36
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 36

Ala Ala Ala Ala
1

<210> SEQ ID NO 37
<211> LENGTH: 4
<212> TYPE: PRT
<213> ORGANISM: Artificial Sequence
<220> FEATURE:

```
<223> OTHER INFORMATION: Synthetic Sequence

<400> SEQUENCE: 37

Ala Ala Ala Ala
1

<210> SEQ ID NO 38
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 38

Ala Ala Ala Ala
1

<210> SEQ ID NO 39
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 39

Ala Ala Ala Ala
1

<210> SEQ ID NO 40
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 40

Ala Ala Ala Ala
1

<210> SEQ ID NO 41
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 41

Ala Ala Ala Ala
1

<210> SEQ ID NO 42
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 42

Ala Ala Ala Ala
1

<210> SEQ ID NO 43
<211> LENGTH: 4
<212> TYPE: PRT
<213> ORGANISM: Artificial Sequence
<220> FEATURE:
<223> OTHER INFORMATION: Synthetic Sequence
```

```
<400> SEQUENCE: 43

Ala Ala Ala Ala
1

<210> SEQ ID NO 44
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 44

Ala Ala Ala Ala
1

<210> SEQ ID NO 45
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 45

Ala Ala Ala Ala
1

<210> SEQ ID NO 46
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 46

Ala Ala Ala Ala
1

<210> SEQ ID NO 47
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 47

Ala Ala Ala Ala
1

<210> SEQ ID NO 48
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 48

Ala Ala Ala Ala
1

<210> SEQ ID NO 49
<211> LENGTH: 764
<212> TYPE: PRT
<213> ORGANISM: Homo sapiens

<400> SEQUENCE: 49
```

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
        275                 280                 285

Ala Lys Lys Cys Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
```

```
                420             425             430
Leu Val Asn Gln Val Asn Ile Asn Ala Leu Ala Ser Lys Lys Asp Asn
            435                 440                 445

Glu Gln His Val Phe Lys Val Lys Asp Met Glu Asn Leu Glu Asp Val
        450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
        530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
        610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
        690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
        755                 760

<210> SEQ ID NO 50
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser
```

```
                        20                  25

<210> SEQ ID NO 51
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 51

Trp Val Arg Gln Ala Pro Gly Lys Gly Leu Glu Trp Val
1               5                   10

<210> SEQ ID NO 52
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 52

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 53
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 53

Trp Gly Gln Gly Thr Leu Val Thr Val Ser Ser
1               5                   10

<210> SEQ ID NO 54
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 54

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 55
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 56
<211> LENGTH: 13
```

```
<212> TYPE: PRT
<213> ORGANISM: Artificial Sequence
<220> FEATURE:
<223> OTHER INFORMATION: Synthetic Sequence

<400> SEQUENCE: 56

Trp Val Arg Gln Ala Pro Gly Gln Gly Leu Glu Trp Met
1               5                   10

<210> SEQ ID NO 57
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 57

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 58
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 58

Trp Gly Gln Gly Thr Leu Val Thr Val Ser Ser
1               5                   10

<210> SEQ ID NO 59
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 59

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 60
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 60

Trp Ile Arg Gln Pro Pro Gly Lys Gly Leu Glu Trp Ile
1               5                   10

<210> SEQ ID NO 61
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 61

Arg Val Thr Ile Ser Val Asp Thr Ser Lys Asn Gln Phe Ser Leu Lys
1               5                   10                  15
```

```
                1               5                   10                  15
Leu Ser Ser Val Thr Ala Ala Asp Thr Ala Val Tyr Tyr Cys
            20                  25                  30
```

<210> SEQ ID NO 62
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 62

```
Trp Gly Gln Gly Thr Leu Val Thr Val Ser Ser
1               5                   10
```

<210> SEQ ID NO 63
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 63

```
Asp Ile Gln Met Thr Gln Ser Pro Ser Ser Leu Ser Ala Ser Val Gly
1               5                   10                  15
Asp Arg Val Thr Ile Thr Cys
            20
```

<210> SEQ ID NO 64
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 64

```
Trp Tyr Gln Gln Lys Pro Gly Lys Ala Pro Lys Leu Leu Ile Tyr
1               5                   10                  15
```

<210> SEQ ID NO 65
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 65

```
Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30
```

<210> SEQ ID NO 66
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 66

```
Phe Gly Gln Gly Thr Lys Val Glu Ile Lys
1               5                   10
```

<210> SEQ ID NO 67
<211> LENGTH: 23

```
<212> TYPE: PRT
<213> ORGANISM: Artificial Sequence
<220> FEATURE:
<223> OTHER INFORMATION: Synthetic Sequence

<400> SEQUENCE: 67

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 68
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 68

Trp Tyr Leu Gln Lys Pro Gly Gln Ser Pro Gln Leu Leu Ile Tyr
1               5                   10                  15

<210> SEQ ID NO 69
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 69

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 70
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 70

Phe Gly Gln Gly Thr Lys Val Glu Ile Lys
1               5                   10

<210> SEQ ID NO 71
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 71

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 72
<211> LENGTH: 15
<212> TYPE: PRT
<213> ORGANISM: Artificial Sequence
<220> FEATURE:
<223> OTHER INFORMATION: Synthetic Sequence
```

```
<400> SEQUENCE: 72

Trp Tyr Gln Gln Lys Pro Gly Gln Pro Pro Lys Leu Leu Ile Tyr
1               5                   10                  15

<210> SEQ ID NO 73
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 73

Gly Val Pro Asp Arg Phe Ser Gly Ser Gly Thr Asp Phe Thr
1               5                   10                  15

Leu Thr Ile Ser Ser Leu Gln Ala Glu Asp Phe Ala Val Tyr Tyr Cys
                20                  25                  30

<210> SEQ ID NO 74
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 74

Phe Gly Gln Gly Thr Lys Val Glu Ile Lys
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(5)
<223> OTHER INFORMATION: This stretch of residues may be repeated

<400> SEQUENCE: 75

Gly Ser Gly Gly Ser
1               5

<210> SEQ ID NO 76
<211> LENGTH: 4
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(4)
<223> OTHER INFORMATION: This stretch of residues may be repeated.

<400> SEQUENCE: 76

Gly Gly Gly Ser
1

<210> SEQ ID NO 77
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 77

Gly Gly Ser Gly
```

```
<210> SEQ ID NO 78
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 78

Gly Gly Ser Gly Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 79

Gly Ser Gly Ser Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 80

Gly Ser Gly Gly Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 81

Gly Gly Gly Ser Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 82

Gly Ser Ser Ser Gly
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 83

Tyr Pro Tyr Asp Val Pro Asp Tyr Ala
1               5
```

```
<210> SEQ ID NO 84
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 84

Asp Tyr Lys Asp Asp Asp Asp Lys
1               5

<210> SEQ ID NO 85
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 85

Glu Gln Lys Leu Ile Ser Glu Glu Asp Leu
1               5                   10

<210> SEQ ID NO 86
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 86

His His His His His
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 87

His His His His His His
1               5

<210> SEQ ID NO 88
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 88

Glu Gln Lys Leu Ile Ser Glu Glu Asp Leu
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 89

Trp Ser His Pro Gln Phe Glu Lys
1               5
```

<210> SEQ ID NO 90
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 90

Tyr Pro Tyr Asp Val Pro Asp Tyr Ala
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 91

Arg Tyr Ile Arg Ser
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 92

Phe His His Thr
1

<210> SEQ ID NO 93
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 93

Trp Glu Ala Ala Ala Arg Glu Ala Cys Cys Arg Glu Cys Cys Ala Arg
1               5                   10                  15

Ala

<210> SEQ ID NO 94
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 94

Thr Phe Phe Tyr Gly Gly Ser Arg Gly Lys Arg Asn Asn Phe Lys Thr
1               5                   10                  15

Glu Glu Tyr

<210> SEQ ID NO 95
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 95

```
Cys Thr Phe Phe Tyr Gly Gly Ser Arg Gly Lys Arg Asn Asn Phe Lys
1               5                   10                  15

Thr Glu Glu Tyr
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 96

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 97
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 97

Thr Phe Val Tyr Gly Gly Cys Arg Ala Lys Arg Asn Asn Phe Lys Ser
1               5                   10                  15

<210> SEQ ID NO 98
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 98

Thr Phe Phe Tyr Gly Gly Cys Arg Gly Lys Arg Asn Asn Phe Lys Thr
1               5                   10                  15

Glu Glu Tyr
```

What is claimed is:

1. A humanized antibody that binds specifically to complement factor Bb, wherein the antibody comprises light chain complementarity determining regions (CDRs) of an antibody light chain variable (VL) region comprising amino acid sequence SEQ ID NO:30 and heavy chain CDRs of an antibody heavy chain variable (VH) region comprising amino acid sequence SEQ ID NO:31.

2. The humanized antibody of claim 1, wherein the antibody comprises a humanized light chain framework region and a humanized heavy chain framework region.

3. The humanized antibody of claim 1, wherein the antibody is selected from the group consisting of an Ig monomer, a Fab fragment, a F(ab')2 fragment, a scFv, a scAb, a Fv, and a bispecific antibody.

4. A pharmaceutical composition comprising the humanized antibody of claim 1.

5. A container comprising the pharmaceutical composition of claim 4.

6. A method of inhibiting C3b/Bb-mediated cleavage of C3 in an individual, the method comprising administering to the individual an effective amount of a humanized antibody that binds specifically to complement factor Bb, wherein the antibody comprises light chain complementarity determining regions (CDRs) of an antibody light chain variable (VL) region comprising amino acid sequence SEQ ID NO:30 and heavy chain CDRs of an antibody heavy chain variable (VH) region comprising amino acid sequence SEQ ID NO:31.

7. A method of treating an individual having paroxysmal nocturnal hemoglobinuria (PNH), the method comprising administering to the individual an effective amount of the humanized antibody of claim 1.

8. A method of treating an individual having atypical hemolytic uremic syndrome (aHUS), the method comprising administering to the individual an effective amount of the humanized antibody of claim 1.

9. An antibody comprising a light chain variable region that comprises amino acid sequence SEQ ID NO:30 and a heavy chain variable region that comprises amino acid sequence SEQ ID NO:31.

10. A nucleic acid encoding a humanized antibody that specifically binds Factor Bb, wherein the antibody comprises light chain complementarity determining regions (CDRs) of an antibody light chain variable (VL) region comprising amino acid sequence SEQ ID NO:30 and heavy chain CDRs of an antibody heavy chain variable (VH) region comprising amino acid sequence SEQ ID NO:31.

11. The nucleic acid of claim 10, wherein the antibody comprises a humanized light chain framework region and a humanized heavy chain framework region.

12. The nucleic acid of claim 10, wherein the antibody is selected from the group consisting of an Ig monomer, a Fab fragment, a F(ab')2 fragment, a scFv, a scAb, and a Fv.

13. A vector comprising the nucleic acid of claim 11.

14. An isolated host cell comprising the vector of claim 13.

15. The isolated host cell of claim 14, wherein the cell is a mammalian cell, an insect host cell, a yeast cell, or a prokaryotic cell.

16. The isolated host cell of claim 15, wherein the cell is a mammalian cell selected from HeLa cells, CHO cells, 293 cells, Vero cells, NIH 3T3 cells, Huh-7 cells, BHK cells, PC12 cells, COS cells, COS-7 cells, RAT1 cells, mouse L cells, HEK cells, and HLHepG2 cells.

17. A method of producing a humanized antibody that specifically binds Factor Bb, comprising culturing the host cell of claim 16, so that the antibody is produced.

18. The method of claim 17, further comprising recovering the antibody.

19. A nucleic acid encoding a polypeptide comprising the light chain complementarity determining regions (CDRs) of an antibody light chain variable (VL) region comprising amino acid sequence SEQ ID NO:30.

20. A nucleic acid encoding a polypeptide comprising the heavy chain complementarity determining regions (CDRs) of an antibody heavy chain variable (VH) region comprising amino acid sequence SEQ ID NO:31.

\* \* \* \* \*